United States Patent
Vu et al.

(10) Patent No.: US 10,251,845 B2
(45) Date of Patent: Apr. 9, 2019

(54) FATTY ACID CYSTEAMINE CONJUGATES AND THEIR USE AS ACTIVATORS OF AUTOPHAGY

(71) Applicant: Catabasis Pharmaceuticals, Inc., Cambridge, MA (US)

(72) Inventors: Chi B. Vu, Boston, MA (US); Michael R. Jirousek, Chardon, OH (US)

(73) Assignee: Catabasis Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 15/529,316

(22) PCT Filed: Nov. 25, 2015

(86) PCT No.: PCT/US2015/062620
§ 371 (c)(1),
(2) Date: May 24, 2017

(87) PCT Pub. No.: WO2016/086103
PCT Pub. Date: Jun. 2, 2016

(65) Prior Publication Data
US 2017/0258741 A1    Sep. 14, 2017

Related U.S. Application Data

(60) Provisional application No. 62/084,754, filed on Nov. 26, 2014.

(51) Int. Cl.
| | |
|---|---|
| *A61K 31/4406* | (2006.01) |
| *C07D 213/82* | (2006.01) |
| *A61K 31/105* | (2006.01) |
| *A61K 31/095* | (2006.01) |
| *A61K 31/121* | (2006.01) |
| *A61K 31/195* | (2006.01) |
| *A61K 45/06* | (2006.01) |
| *C07C 323/23* | (2006.01) |
| *A61K 47/54* | (2017.01) |

(52) U.S. Cl.
CPC .......... *A61K 31/105* (2013.01); *A61K 31/095* (2013.01); *A61K 31/121* (2013.01); *A61K 31/195* (2013.01); *A61K 31/4406* (2013.01); *A61K 45/06* (2013.01); *A61K 47/54* (2017.08); *C07C 323/23* (2013.01); *C07D 213/82* (2013.01)

(58) Field of Classification Search
None
See application file for complete search history.

(56) References Cited

U.S. PATENT DOCUMENTS

| | | | |
|---|---|---|---|
| 8,173,831 B2 | 5/2012 | Milne et al. | |
| 8,445,707 B1 | 5/2013 | Kandula | |
| 8,729,293 B2 | 5/2014 | Milne et al. | |
| 8,735,378 B2 | 5/2014 | Milne et al. | |
| 8,735,379 B2 | 5/2014 | Milne et al. | |
| 8,765,963 B2 | 7/2014 | Milne et al. | |
| 8,765,964 B2 | 7/2014 | Milne et al. | |
| 8,940,903 B2 | 1/2015 | Milne et al. | |
| 8,946,451 B2 | 2/2015 | Milne et al. | |
| 8,969,354 B2 | 3/2015 | Milne et al. | |
| 9,029,548 B2 | 5/2015 | Milne et al. | |
| 9,084,826 B2 | 7/2015 | Milne et al. | |
| 9,085,527 B2 | 7/2015 | Vu et al. | |
| 9,139,516 B2 | 9/2015 | Milne et al. | |
| 9,150,504 B2 | 10/2015 | Milne et al. | |
| 9,216,224 B2 | 12/2015 | Milne et al. | |
| 9,238,077 B2 | 1/2016 | Milne et al. | |
| 9,272,984 B2 | 3/2016 | Milne et al. | |

(Continued)

FOREIGN PATENT DOCUMENTS

| | | |
|---|---|---|
| WO | WO-2012/115695 A1 | 8/2012 |
| WO | WO-2012/154554 A1 | 11/2012 |

(Continued)

OTHER PUBLICATIONS

Arunachalam et al., (2000) "Enzymatic reduction of disulfide bonds in lysosomes: characterization of a gamma-interferon-inducible lysosomal thiol reductase (GILT)," PNAS, 97:745-750.
Bjorkoy et al., (2009) "Monitoring Autophagic Degradation of p62/SQSTM1," Methods Enzymol., 452:181-197.
Derichs, (2013) "Targeting a genetic defect: cystic fibrosis transmembrane conductance regulator modulators in cystic fibrosis," Eur. Resp. Rev., 22:58-65.
International Search Report for International Patent Application No. PCT/US2015/062620 prepared by the Australian Patent Office dated Feb. 24, 2016 (7 pages).
Junkins et al,. (2013) "Autophagy enhances bacterial clearance during *P. aeuroginosa* lung infection," PLOS One, 8:e72263.
Levine and Kroemer, (2008) "Autophagy in the pathogenesis of disease," Cell, 132:27-42.

(Continued)

*Primary Examiner* — Zinna Northington Davis
(74) *Attorney, Agent, or Firm* — Goodwin Procter LLP

(57) ABSTRACT

The invention relates to (i) 6-membered heteroaryl substituted fatty acid cystamine conjugates, compositions thereof, methods of treating diseases involving dysregulation of autophagy, such as cystic fibrosis, idiopathic pulmonary fibrosis (IPF), a neurodegenerative disease, inflammatory disease, liver disease, muscle disease, infection and immune disease with this compound, or (ii) a method of treating idiopathic pulmonary fibrosis, mitochondrial diseases, Leigh Syndrome, Diabetes Mellitus and Deafness (DAD), Leber's hereditary optic neuropathy, Neuropathy-ataxia-retinis pigmentosa and ptosis (NARP), myoneurogenic gastrointestinal encephalopathy (MNGIE), myoclonic epilepsy with ragged red fibers (MERRF), or mitochondrial myopathy-encephalomy-opathy-lactic acidosis stroke like symptoms (MELAS), comprising administering to a patient the fatty acid cysteamine conjugate, (4Z, 7Z. 10Z, 13Z, 16Z, 19Z)—N-(2-mercaptoethyl) docosa-4,7,10,13,16,19-hexaenamide or (5Z, 8Z, 11Z, 14Z, 17Z)—N-(2-mercaptoethyl) icosa-5,8,11,14,17-pentaenamide.

24 Claims, 15 Drawing Sheets

(56) References Cited

U.S. PATENT DOCUMENTS

| | | | |
|---|---|---|---|
| 9,278,136 | B2 | 3/2016 | Milne et al. |
| 9,289,503 | B2 | 3/2016 | Milne et al. |
| 9,458,094 | B2 | 10/2016 | Milne et al. |
| 9,486,534 | B2 | 11/2016 | Milne et al. |
| 9,708,245 | B2 | 7/2017 | Vu et al. |
| RE46,605 | E | 11/2017 | Milne et al. |
| RE46,608 | E | 11/2017 | Milne et al. |
| 2011/0053990 | A1 | 3/2011 | Milne et al. |
| 2011/0082120 | A1 | 4/2011 | Milne et al. |
| 2011/0082156 | A1 | 4/2011 | Milne et al. |
| 2011/0082202 | A1 | 4/2011 | Milne et al. |
| 2011/0082210 | A1 | 4/2011 | Milne et al. |
| 2011/0212958 | A1 | 9/2011 | Milne et al. |
| 2011/0213028 | A1 | 9/2011 | Milne et al. |
| 2012/0252810 | A1 | 10/2012 | Vu et al. |
| 2013/0045939 | A1 | 2/2013 | Vu et al. |
| 2013/0059801 | A1 | 3/2013 | Milne et al. |
| 2013/0190327 | A1 | 7/2013 | Milne et al. |
| 2013/0244966 | A1 | 9/2013 | Milne et al. |
| 2014/0093513 | A1 | 4/2014 | Milne et al. |
| 2014/0288025 | A1 | 9/2014 | Milne et al. |
| 2014/0315786 | A1 | 10/2014 | Jirousek et al. |
| 2015/0344430 | A1 | 12/2015 | Milne et al. |
| 2015/0352094 | A1 | 12/2015 | Bemis et al. |
| 2016/0015819 | A1 | 1/2016 | Milne et al. |
| 2016/0106712 | A1 | 4/2016 | Milne et al. |
| 2016/0129122 | A1 | 5/2016 | Milne et al. |
| 2016/0287712 | A1 | 10/2016 | Jirousek et al. |
| 2016/0340294 | A1 | 11/2016 | Milne et al. |
| 2016/0346397 | A1 | 12/2016 | Milne et al. |
| 2017/0073305 | A1 | 3/2017 | Milne et al. |
| 2017/0144972 | A1 | 5/2017 | Milne et al. |
| 2017/0246193 | A1 | 8/2017 | Milne et al. |
| 2017/0342046 | A1 | 11/2017 | Vu |
| 2018/0028674 | A1 | 2/2018 | Milne et al. |

FOREIGN PATENT DOCUMENTS

| | | |
|---|---|---|
| WO | WO-2012/154564 A1 | 11/2012 |
| WO | WO-2012/161798 A1 | 11/2012 |
| WO | WO-2013/033602 A2 | 3/2013 |
| WO | WO-2014/107730 A2 | 7/2014 |
| WO | WO-2014/204856 A1 | 12/2014 |
| WO | WO-2016/086136 A1 | 6/2016 |

OTHER PUBLICATIONS

Luciani et al., (2010) "Defective CFTR induces aggresome formation and lung inflammation in cystic fibrosis through ROS-mediated autophagy inhibition," Nat. Cell Biol., 12:863-875.

Luciani et al., (2011), "Cystic Fibrosis: a Disorder with Defective Autophagy," *Autophagy*, 7(1):104-106.

Luciani et al., (2012) "Targeting autophagy as a novel strategy for facilitating the therapeutic action of potentiators on ΔF508 cystic fibrosis transmembrane conductance regulator," Autophagy, 8:1657-1672.

MacDonald et al., (2007) "Cystic fibrosis transmembrane regulator protein mutations: 'class' opportunity for novel drug innovation," Paediatric Drugs, 9:1-10.

Man et al., (1984) "Gastric mucosal histamine, histamine formation capacity (HFC) and plasma gastrin after cysteamine administration," Brit. J. Exp. Pathology, 65:759-765.

Nichols et al., (2008) "Anti-inflammatory therapies for cystic fibrosis-related lung disease," Clinic Rev. Allerg. Immunol., 35:135-153.

Ren et al., (2013) "VX-809 corrects folding defects in cystic fibrosis transmembrane conductance regulator protein through action on membrane-spanning domain 1," Mol. Biol. Cell, 24:3016-3024.

Rommens et al. (1989) "Identification of the cystic fibrosis gene: chromosome walking and jumping," Science, 245:1059-1065.

Rowntree and Harris (2003) "The Phenotypic Consequences of CFTR Mutations," Ann. Hum. Genet., 67:471-485.

Selman et al., (2000) "TIMP-1, -2, -3, and -4 in idiopathic pulmonary fibrosis. A prevailing nondegradative lung microenvironment?," Am. J. Phys. Lung Cell Mol. Physiol., 279:L562-L574.

Tanida et al., (2008) "LC3 and Autophagy," Methods Mol. Biol., 445:77-88.

Van Goor et al., (2009) "Rescue of CF airway epithelial cell function in vitro by a CFTR potentiator, VX-770," PNAS, 106:18825-18830.

Van Goor et al., (2011) "Correction of the F508del-CFTR protein processing defect in vitro by the investigational drug VX-809," PNAS, 108:18843-18848.

Written Opinion of the International Searching Authority for International Patent Application No. PCT/US2015/062620 prepared by the Australian Patent Office dated Feb. 24, 2016 (6 pages).

Zielenski (2000) "Genotype and phenotype in cystic fibrosis," Respiration, 67:117-133.

FATTY ACID CYSTEAMINE CONJUGATES AND THEIR USE AS ACTIVATORS OF AUTOPHAGY

This application is a U.S. National Stage Application filed under 35 U.S.C. § 371 of International Patent Application No. PCT/US2015/062620, filed Nov. 25, 2015, which claims the benefit of and priority to U.S. Provisional Patent Application No. 62/084,754, filed Nov. 26, 2014, the entire disclosures of each of which are incorporated by reference herein in their entireties.

CROSS-REFERENCE TO RELATED APPLICATIONS

This application claims the benefit of and priority to U.S. Provisional Patent Application No. 62/084,754, filed Nov. 26, 2014, the entire disclosure of which is incorporated by reference herein in its entirety.

FIELD OF THE INVENTION

The invention relates to fatty acid cysteamine conjugates, compositions comprising a fatty acid cysteamine conjugate, and methods for using such conjugates and compositions to treat disease, such as a disease caused by dysregulation of autophagy.

BACKGROUND

Autophagy is an evolutionarily conserved lysosomal degradation pathway to essentially self-digest some cellular components (see, Levine and Kroemer (2008) CELL, 132, p. 27-42). This self-digestion process helps cells remove extraneous or damaged organelles, defective or mis-folded proteins, and even invading microorganisms. It has been speculated that autophagy is down-regulated in a number of diseases, for example, cystic fibrosis (Luciani et al. (2011) AUTOPHAGY, 7, p. 104-106).

Cystic fibrosis (CF) has been described as one of the most common, life-shortening autosomal recessive hereditary diseases in the Caucasian population. It is an orphan disease that affects approximately 30,000 children and adults in the U.S. (70,000 worldwide); and about 1,000 new cases are diagnosed each year. The disease is characterized by mutations in the cystic fibrosis transmembrane conductance regulator (CFTR), which results in either loss or impaired ability to transport chloride ions by various secretory and absorptive epithelial cells in the lung, pancreas, liver, and intestine (see, for example, Derichs (2013) EUR. RESP. REV, 22, p. 58-65). The resulting decrease in anion transport and imbalance in fluid homeostasis produce thick and viscous mucus in the lungs, which can obstruct airways, causing chronic inflammation and infection. This leads to a progressive decline in lung function and a limited life expectancy in patients with the more severe form of the disease.

The CFTR is a cAMP-activated ATP-gated ion channel composed of approximately 1,480 amino acids. The protein consists of 5 domains: two transmembrane domains, each containing 6 spans of alpha helices. Each transmembrane domain is connected to a nucleotide binding domain (NBD). The first NBD is connected to the second transmembrane domain by a regulatory "R" domain. The gene encoding CFTR was reported in year 1989 (see, Rommens et al. (1989) SCIENCE, 245, p. 1059-1065). Since then, over 1900 sequence variations in the CFTR gene have been identified, the majority of which fall into one of the following 6 classes: Class I mutations result from non-sense and frame shift mutations, which reduce the quantity of the CFTR; Class II mutations have folding defects which result in premature degradation; Class III mutations result in limited channel gating; Class IV mutations have conductance defects; Class V mutations have a transcriptional defect that results in a reduced quantity of the CFTR being produced; Class VI mutations have a high turnover of the CFTR at the channel surface (see, for example, Rowntree and Harris (2003) ANN. HUM. GENET., 67, p. 471-485; Zielenski (2000) RESPIRATION, 67, p. 117-133; and MacDonald et al. (2007) PAEDIATRIC DRUGS, 9, p. 1-10).

To manifest the debilitating CF disease, an individual inherits two defective CFTR alleles, one from each parent. Of the over 1900 sequence variations in the CFTR that have been identified, the following 4 mutations have a worldwide prevalence of around 1-3% each: G551D, W1282X, G542X and N1303K. The most prevalent CFTR mutation, with an allelic frequency of about 90% worldwide, is the ΔF508 mutation (a Class II mutation, deletion of a phenylalanine which causes protein mis-folding and premature degradation). The ΔF508 deletion mutation can be manifested in either homozygous or heterozygous form.

Research on therapeutic interventions has identified several anti-inflammatory and anti-infective therapies useful in controlling certain debilitating symptoms of CF (see, for example, Nichols et al. (2008) CLINIC REV. ALLERG. IMMUNOL., 35, p. 135-153). More recently, disease-modifying therapies have been introduced to address the defective CFTR. CFTR "potentiators" were designed to increase the open probability of CFTR channels that are available at the membrane but have gating (Class III) and conductance (Class IV) mutations. Ivacaftor (VX-770) is a CFTR potentiator that received FDA approval for the treatment of CF patients with gating mutations that included G551D, G178R, S549N, S549R, G551S, G124E, S1251N, S1255P, and G1349D (see, for example, Van Goor et al. (2009) PNAS, 106, p. 18825-18830). However, patients with these gating mutations represent only a small percentage of CF patients worldwide.

In addition to CFTR potentiators, clinical developments have been reported evaluating the potential of a CFTR "corrector" to increase the amount of CFTR that can be delivered to the cell membrane. VX-809 (Lumacaftor) is a CFTR corrector that has recently been approved by the FDA, when used in combination with Ivacaftor, in CF patients with homozygous ΔF508 mutation (see, for example, Van Goor et al. (2011) PNAS, 108, p. 18843-18848; and Ren et al. (2013) MOL. BIOL. CELL, 24, p. 3016-3024).

Despite the efforts made to date, there is still an ongoing need for additional compositions and methods for treating disorders associated with dysregulation of autophagy, for example, CF, and in particular certain forms of CF associated with mutations that are difficult to treat using existing therapies.

SUMMARY

The invention provides methods and compositions for activating autophagy and treating various medical diseases associated with dysregulation of autophagy, in particular, disorders where the level of autophagy is reduced relative to subjects without the disorder. The invention is based, in part, upon the discovery that fatty acid cysteamine conjugates are useful in activating autophagy, and the fatty acid cysteamine conjugates can be used to treat a variety of human diseases, such as CF. Fatty acid cysteamine conjugates described herein have therapeutic effects that cannot be achieved by administering cysteamine or a fatty acid separately or a combination of individual components. The covalent linkage of cysteamine and a fatty acid, for example, an omega-3 fatty acid, allows the simultaneous delivery of both components to an intracellular location, whereupon the individual components are released by cleavage (e.g., enzymatic cleavage) at the location and at the same time.

One benefit of the invention is that administration of the fatty acid cysteamine conjugate results in a greater level of autophagy activation than can be achieved by administering the components individually. Furthermore, administration of the fatty acid cysteamine conjugates can cause a synergistic decrease in inflammation at a much lower concentration than cysteamine administered alone, or in combination with the unconjugated fatty acid. Thus, the fatty acid cysteamine conjugate provides multiple benefits that cannot be achieved by separate administration of individual components (separately or co-administered) that are conjugated to produce the fatty acid cysteamine conjugate.

Exemplary fatty acid cysteamine conjugates are described herein using generic and specific chemical formulae. For example, the invention provides a family of fatty acid cysteamine conjugates embraced by Formula I:

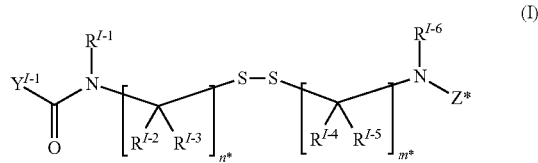

(I)

or a pharmaceutically acceptable salt or solvate thereof, wherein the variables are as defined in the detailed description below.

Similarly, the invention provides a family of fatty acid cysteamine conjugates embraced by Formula IA:

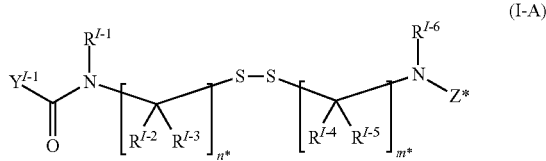

(I-A)

or a pharmaceutically acceptable salt or solvate thereof, wherein the variables are as defined in the detailed description below.

Similarly, the invention provides a family of fatty acid cysteamine conjugates embraced by Formula IB:

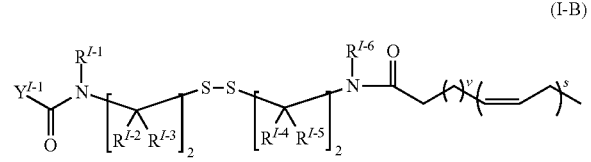

(I-B)

or a pharmaceutically acceptable salt or solvate thereof, wherein the variables are as defined in the detailed description below.

Similarly, the invention provides a family of fatty acid cysteamine conjugates embraced by Formula III:

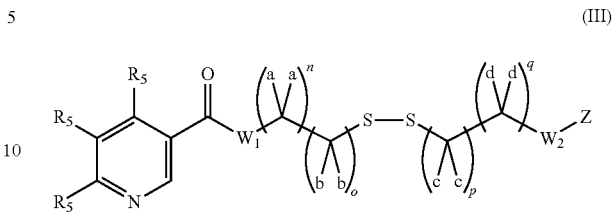

(III)

or a pharmaceutically acceptable salt or solvate thereof, wherein the variables are as defined in the detailed description below.

Similarly, the invention provides a family of fatty acid cysteamine conjugates embraced by Formula IV:

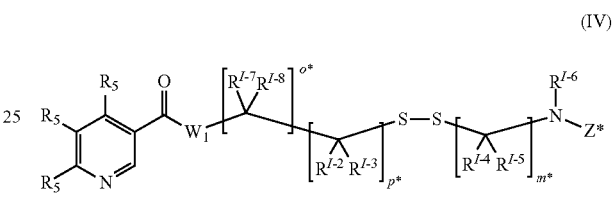

(IV)

or a pharmaceutically acceptable salt or solvate thereof, wherein the variables are as defined in the detailed description below.

Additional generic formulae and specific fatty acid cysteamine conjugates are described in the detailed description and examples.

Another aspect of the invention provides a method of treating a disease described herein, such as CF, idiopathic pulmonary fibrosis (IPF), a neurodegenerative disease, inflammatory disease, liver disease, muscle disease, infection, mitochondria disease or immune disease. The method comprises administering to a subject in need thereof a therapeutically effective amount of a fatty acid cysteamine conjugate described herein, such as a compound of Formula I, to treat the disease. Exemplary neurodegenerative diseases include Huntington's disease, Parkinson's disease, Alzheimer's disease, and transmissible spongiform encephalopathies. In certain embodiments, the disease to be treated is CF. In certain embodiments, the disease to be treated is IPF.

Another aspect of the invention provides a method of activating autophagy in a subject. The method comprises administering to a subject in need thereof an effective amount of a fatty acid cysteamine conjugate described herein, such as a compound of Formula I, Formula I-A, Formula I-B, Formula II, Formula III, or Formula IV, to activate autophagy in the subject. In certain embodiments, the subject suffers from CF, a neurodegenerative disease, or inflammatory disease.

Pharmaceutical compositions that comprise a fatty acid cysteamine conjugate (for example, the conjugate of Formula I, Formula I-A, Formula I-B, Formula II, Formula III, Formula IV) and a pharmaceutically acceptable carrier are provided. The compositions are useful for treating a disease by activating autophagy.

Various aspects and embodiments of the invention are described in more detail below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise.

DETAILED DESCRIPTION

Figure 1A:
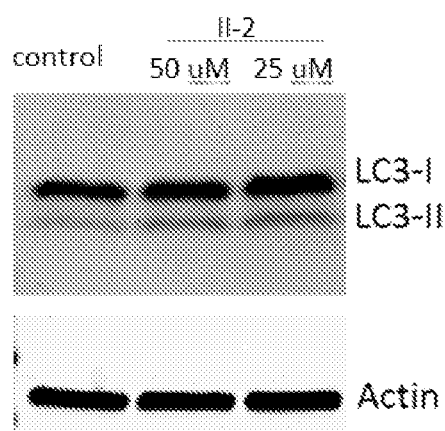
FIG. 1A is an Immunoblot of Huh-7 cells when treated with compound II-2.

The invention provides methods and compositions for activating autophagy and treating various medical diseases, in particular diseases associated with autophagy dysregulation. The invention is based, in part, upon the discovery that fatty acid cysteamine conjugates are useful in activating autophagy, and can be used treat or prevent a variety of human diseases, for example, CF. Fatty acid cysteamine conjugates described herein have therapeutic effects that cannot be achieved by administering cysteamine or a fatty acid separately or as a combination of individual components. The covalent linkage of cysteamine and an omega-3 fatty acid allows the simultaneous delivery of both components to a location, whereupon the individual components are released by cleavage (e.g., enzymatic cleavage) at the location and at the same time. A benefit of the invention is that administration of the fatty acid cysteamine conjugate results in a greater level of autophagy activation than can be achieved by administering the components individually. Furthermore, administration of the fatty acid cysteamine conjugates can cause a synergistic decrease in inflammation at a much lower concentration than cysteamine administered alone, or in combination with the unconjugated fatty acid. As a result, the fatty acid cysteamine conjugate provides multiple benefits that cannot be achieved by separate administration of individual components (either separately or co-administered) that are conjugated to produce the fatty acid cysteamine conjugate. The fatty acid cysteamine conjugates and therapeutic methods described herein are contemplated to have particular advantages in treating CF.

CF is an orphan disease that affects some 30,000 patients in the United States. It is a debilitating disease that is associated with a genetic mutation that leads a defective CFTR, an ion channel that transports chloride ions across epithelial cell membranes. Patients with CF have been shown to have a defective and decreased level of autophagy, an evolutionarily conserved lysosomal degradation pathway that facilitates cells to remove extraneous or damaged organelles, defective or mis-folded proteins and even invading microorganisms. Activating autophagy has been shown to be potentially useful in restoring function to a defective CFTR.

It is contemplated that the activation of autophagy is also useful for the treatment of a variety of diseases other than CF, for example, diseases associated with reduced autophagy in cells, tissues, organelles, organs. Such diseases include, for example, idiopathic pulmonary fibrosis (IPF), pulmonary hypertension (PH), neurodegenerative diseases, liver diseases, muscle diseases, cardiac diseases, metabolic diseases, infection, immunity and inflammatory diseases. Pulmonary hypertension includes pulmonary arterial hypertension (WHO group I, idiopathic, heritable and drug/toxin-induced PH), pulmonary hypertension due to systolic or diastolic dysfunction, valvular heart disease (WHO group II) and pulmonary hypertension of other classifications that include those from WHO group III-V. Liver diseases include non-alcoholic fatty liver disease (NAFLD), non-alcoholic steatohepatitis (NASH), NASH cirrhosis and hepatocellular carcinoma (HCC). An example of a metabolic disease that can be treated with a fatty acid cysteamine conjugate includes type 2 diabetes, which is commonly observed among CF patients. Neurodegenerative diseases include Huntington's disease, Parkinson's disease, Alzheimer's disease, and transmissible spongiform encephalopathies. Autophagy restoration therapy could also be useful for diseases such as Vici syndrome, sarcopenia and muscular dystrophy. There are multiple forms of muscular dystrophy and these include Duchenne muscular dystrophy, which is most common. Other forms of muscular dystrophy include Becker, limb-girdle, congenital, facioscapulohumeral, myotonic, oculopharyngeal, distal and Emery-Dreifuss muscular dystrophy. Other diseases that have defective autophagy include age-related macular degeneration, Danon disease, X-linked myopathy, infantile autophagic vacuolar myopathy, adult onset vacuolar myopathy, Pompe disease, sporadic inclusion body myositis, limb girdle muscular dystrophy type 2B, and Miyoshi myopathy. Fatty acid cysteamine conjugates may also useful for the treatment of mitochondrial diseases such as Leigh Syndrome, Diabetes Mellitus and Deafness (DAD), Leber's hereditary optic neuropathy, Neuropathy-ataxia-retinis pigmentosa and ptosis (NARP), myoneurogenic gastrointestinal encephalopathy (MNGIE), myoclonic epilepsy with ragged red fibers (MERRF), and mitochondrial myopathy-encephalomyopathy-lactic acidosis-stroke like symptoms (MELAS). Since cysteamine is being released intracellularly, the compounds of the invention may also be used to treat the lysosomal disorder nephropathic cystinosis.

Unless otherwise indicated, the practice of the present invention employs conventional techniques of organic chemistry, cell biology, biochemistry, pharmacology, formulation and drug delivery. Various aspects of the invention are set forth below in sections for clarity; however, it is understood that aspects of the invention described in one particular section are not to be limited to any particular section.

I. Definitions

To facilitate an understanding of the present invention, a number of terms and phrases are defined below.

The articles "a" and "an" are used in this disclosure to refer to one or more than one (i.e., to at least one) of the grammatical object of the article, unless the context is inappropriate. By way of example, "an element" means one element or more than one element.

The term "and/or" is used in this disclosure to mean either "and" or "or" unless indicated otherwise.

The term "alkyl" as used herein refers to a saturated straight or branched hydrocarbon, such as a straight or branched group of 1-12, 1-10, or 1-6 carbon atoms, referred to herein as $C_1$-$C_{12}$alkyl, $C_1$-$C_{10}$alkyl, and $C_1$-$C_6$alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

The term "$C_1$-$C_3$ alkyl" refers to a straight or branched chain saturated hydrocarbon containing 1-3 carbon atoms. Examples of a $C_1$-$C_3$ alkyl group include, but are not limited to, methyl, ethyl, propyl and isopropyl. The term "$C_1$-$C_4$ alkyl" refers to a straight or branched chain saturated hydrocarbon containing 1-4 carbon atoms. Examples of a $C_1$-$C_4$ alkyl group include, but are not limited to, methyl, ethyl, propyl, butyl, isopropyl, isobutyl, sec-butyl and tert-butyl. The term "$C_1$-$C_5$ alkyl" refers to a straight or branched chain saturated hydrocarbon containing 1-5 carbon atoms. Examples of a $C_1$-$C_5$ alkyl group include, but are not limited to, methyl, ethyl, propyl, butyl, pentyl, isopropyl, isobutyl, sec-butyl and tert-butyl, isopentyl and neopentyl. The term "$C_1$-$C_6$ alkyl" refers to a straight or branched chain saturated hydrocarbon containing 1-6 carbon atoms. Examples of a $C_1$-$C_6$ alkyl group include, but are not limited to, methyl, ethyl, propyl, butyl, pentyl, hexyl, isopropyl, isobutyl, sec-butyl, tert-butyl, isopentyl, and neopentyl.

The term "cycloalkyl" refers to a cyclic, saturated hydrocarbon, such as one containing 3-6 carbon atoms. The cycloalkyl may contain 3-12, 3-8, 4-8, or 4-6 ring carbon atoms, referred to herein, e.g., as "$C_{4-8}$cycloalkyl". Examples of a cycloalkyl group include, but are not limited to, cyclopropyl, cyclobutyl, cyclopentyl and cyclohexyl. Unless specified otherwise, it is understood that any of the substitutable hydrogens on a cycloalkyl can be substituted with halogen, $C_1$-$C_3$ alkyl, hydroxyl, alkoxy and cyano groups. In certain embodiments, the cycloalkyl is not substituted.

Unless indicated otherwise, the term "aryl" refers to carbocyclic, aromatic hydrocarbon group having 1 to 2 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment, such substituents include, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. In certain other embodiments, the aromatic ring is not substituted, i.e., it is unsubstituted. In certain embodiments, the aryl group is a 6-10 membered ring structure. In certain embodiments, the aryl group is a 6-10 membered carbocyclic ring structure.

The term "aralkyl" refers to an alkyl group substituted with an aryl group.

The terms "heterocyclyl" and "heterocyclic group" are art-recognized and refer to saturated, partially unsaturated, or aromatic 3- to 10-membered ring structures, alternatively 3- to 7-membered rings, whose ring structures include one to four heteroatoms, such as nitrogen, oxygen, and sulfur. The number of ring atoms in the heterocyclyl group can be specified using $C_x$-$C_x$ nomenclature where x is an integer specifying the number of ring atoms. For example, a $C_3$-$C_7$heterocyclyl group refers to a saturated or partially unsaturated 3- to 7-membered ring structure containing one to four heteroatoms, such as nitrogen, oxygen, and sulfur. The designation "$C_3$-$C_7$" indicates that the heterocyclic ring contains a total of from 3 to 7 ring atoms, inclusive of any heteroatoms that occupy a ring atom position. One example of a $C_3$heterocyclyl is aziridinyl. Heterocycles may also be mono-, bi-, or other multi-cyclic ring systems. A heterocycle may be fused to one or more aryl, partially unsaturated, or saturated rings. Heterocyclyl groups include, for example, biotinyl, chromenyl, dihydrofuryl, dihydroindolyl, dihydropyranyl, dihydrothienyl, dithiazolyl, homopiperidinyl, imidazolidinyl, isoquinolyl, isothiazolidinyl, isooxazolidinyl, morpholinyl, oxolanyl, oxazolidinyl, phenoxanthenyl, piperazinyl, piperidinyl, pyranyl, pyrazolidinyl, pyrazolinyl, pyridyl, pyrimidinyl, pyrrolidinyl, pyrrolidin-2-onyl, pyrrolinyl, tetrahydrofuryl, tetrahydroisoquinolyl, tetrahydropyranyl, tetrahydroquinolyl, thiazolidinyl, thiolanyl, thiomorpholinyl, thiopyranyl, xanthenyl, lactones, lactams such as azetidinones and pyrrolidinones, sultams, sultones, and the like. Unless specified otherwise, the heterocyclic ring is optionally substituted at one or more positions with substituents such as alkanoyl, alkoxy, alkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, oxo, phosphate, phosphonato, phosphinato, sulfate, sulfide, sulfonamido, sulfonyl and thiocarbonyl. In certain embodiments, the heterocyclyl group is not substituted, i.e., it is unsubstituted.

The term "heteroaryl" is art-recognized and refers to aromatic groups that include at least one ring heteroatom. In certain instances, a heteroaryl group contains 1, 2, 3, or 4 ring heteroatoms. Representative examples of heteroaryl groups include pyrrolyl, furanyl, thiophenyl, imidazolyl, oxazolyl, thiazolyl, triazolyl, pyrazolyl, pyridinyl, pyrazinyl, pyridazinyl and pyrimidinyl, and the like. Unless specified otherwise, the heteroaryl ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. The term "heteroaryl" also includes polycyclic ring systems having two or more rings in which two or more carbons are common to two adjoining rings (the rings are "fused rings") wherein at least one of the rings is heteroaromatic, e.g., the other cyclic rings may be cycloalkyls, cycloalkenyls, cycloalkynyls, and/or aryls. In certain embodiments, the heteroaryl ring is substituted at one or more ring positions with halogen, alkyl, hydroxyl, or alkoxyl. In certain other embodiments, the heteroaryl ring is not substituted, i.e., it is unsubstituted. In certain embodiments, the heteroaryl group is a 5- to 10-membered ring structure, alternatively a 5- to 6-membered ring structure, whose ring structure includes 1, 2, 3, or 4 heteroatoms, such as nitrogen, oxygen, and sulfur.

The term "alkenyl" as used herein refers to an unsaturated straight or branched hydrocarbon having at least one carbon-carbon double bond, such as a straight or branched group of 2-12, 2-10, or 2-6 carbon atoms, referred to herein as $C_2$-$C_{12}$alkenyl, $C_2$-$C_{10}$alkenyl, and $C_2$-$C_6$alkenyl, respectively. Exemplary alkenyl groups include vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl, and the like.

The term "alkynyl" as used herein refers to an unsaturated straight or branched hydrocarbon having at least one carbon-carbon triple bond, such as a straight or branched group of 2-12, 2-10, or 2-6 carbon atoms, referred to herein as $C_2$-$C_{12}$alkynyl, $C_2$-$C_{10}$alkynyl, and $C_2$-$C_6$alkynyl, respectively. Exemplary alkynyl groups include ethynyl, prop-1-yn-1-yl, and but-1-yn-1-yl.

The terms "amine" and "amino" are art-recognized and refer to both unsubstituted and substituted amines, e.g., a moiety represented by the general formula $N(R^{50})(R^{51})$, wherein $R^{50}$ and $R^{51}$ each independently represent hydrogen, alkyl, cycloalkyl, heterocyclyl, alkenyl, aryl, aralkyl, or —(CH$_2$)$_m$—R$^{61}$; or $R^{50}$ and $R^{51}$, taken together with the N atom to which they are attached complete a heterocycle having from 4 to 8 atoms in the ring structure; $R^{61}$ represents an aryl, a cycloalkyl, a cycloalkenyl, a heterocycle or a polycycle; and m is zero or an integer in the range of 1 to 8. In certain embodiments, $R^{50}$ and $R^{51}$ each independently represent hydrogen, alkyl, alkenyl, or —(CH$_2$)$_m$—R$^{61}$.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O— alkenyl, —O-alkynyl, —O—(CH$_2$)$_m$—R$_{61}$, where m and R$_{61}$ are described above.

The term "carbamate" as used herein refers to a radical of the form —R$_g$OC(O)N(R$_h$)—, —R$_g$OC(O)N(R$_h$)R$_i$—, or —OC(O)NR$_h$R$_i$, wherein R$_g$, R$_h$ and R$_i$ are each independently alkoxy, aryloxy, alkyl, alkenyl, alkynyl, amide, amino, aryl, arylalkyl, carboxy, cyano, cycloalkyl, ester, ether, formyl, halogen, haloalkyl, heteroaryl, heterocyclyl, hydroxyl, ketone, nitro, sulfide, sulfonyl, or sulfonamide. Exemplary carbamates include arylcarbamates and heteroaryl carbamates, e.g., wherein at least one of R$_g$, R$_h$ and R$_i$ are independently aryl or heteroaryl, such as phenyl and pyridinyl.

The symbol "⁓" indicates a point of attachment.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present invention encompasses various stereoisomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly. It is understood that graphical depictions of chemical structures, e.g., generic chemical structures, encompass all stereoisomeric forms of the specified compounds, unless indicated otherwise.

Individual stereoisomers of compounds of the present invention can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, or (3) direct separation of the mixture of optical enantiomers on chiral chromatographic columns. Stereoisomeric mixtures can also be resolved into their component stereoisomers by well-known methods, such as chiral-phase gas chromatography, chiral-phase high performance liquid chromatography, crystallizing the compound as a chiral salt complex, or crystallizing the compound in a chiral solvent. Further, stereoisomers can be obtained from stereomerically-pure intermediates, reagents, and catalysts by well-known asymmetric synthetic methods.

Geometric isomers can also exist in the compounds of the present invention. The symbol ═══ denotes a bond that may be a single, double or triple bond as described herein. The present invention encompasses the various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers.

Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring are designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

The invention also embraces isotopically labeled compounds of the invention which are identical to those recited herein, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively.

Certain isotopically-labeled disclosed compounds (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in, for example, the Examples herein, by substituting an isotopically labeled reagent for a non-isotopically labeled reagent.

The terms "fatty acid cysteamine derivatives" and "fatty acid cysteamine conjugates" include any and all possible isomers, stereoisomers, enantiomers, diastereomers, tautomers, pharmaceutically acceptable salts, hydrates, and solvates of the fatty acid cysteamine derivatives and fatty acid cysteamine conjugates described herein.

The term "any side chain of a naturally occurring amino acid" refers to a side chain of any one of the following amino acids: Isoleucine, Alanine, Leucine, Asparagine, Lysine, Aspartate, Methionine, Cysteine, Phenylalanine, Glutamate, Threonine, Glutamine, Tryptophan, Glycine, Valine, Proline, Arginine, Serine, Histidine, and Tyrosine.

The term "fatty acid" as used herein means an omega-3 fatty acid and fatty acids that are metabolized in vivo to omega-3 fatty acids. Non-limiting examples of fatty acids are all-cis-7,10,13-hexadecatrienoic acid, α-linolenic acid (ALA or all-cis-9,12,15-octadecatrienoic acid), stearidonic acid (STD or all-cis-6,9,12,15-octadecatetraenoic acid), eicosatrienoic acid (ETE or all-cis-11,14,17-eicosatrienoic acid), eicosatetraenoic acid (ETA or all-cis-8,11,14,17-eicosatetraenoic acid), eicosapentaenoic acid (EPA or all-cis-5,8,11,14,17-eicosapentaenoic acid), docosapentaenoic acid (DPA, clupanodonic acid or all-cis-7,10,13,16,19-docosapentaenoic acid), docosahexaenoic acid (DHA or all-cis-4,7,10,13,16,19-docosahexaenoic acid), tetracosapentaenoic acid (all-cis-9,12,15,18,21-docosahexaenoic acid), or tetracosahexaenoic acid (nisinic acid or all-cis-6,9,12,15,18,21-tetracosenoic acid).

The term, "cysteamine" refers to a molecule having a formula

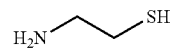

(also known as 2-aminoethane-1-thiol), which can be derived from a cystamine. A cystamine is the disulfide form of a thiol containing compound cysteamine, also known as 2-aminoethane-1-thiol. When the disulfide form cystamine is taken up inside cells, it is reduced to the thiol compound cysteamine by the action of thiol reductase (see, Arunachalam et al. (2000) PNAS, 97, p. 745-750). The thiol compound cysteamine is considered to be the active component of cystamine in cells. Non-limiting examples of cystamine molecules that can deliver the active thiol compound cysteamine inside cells are listed in Scheme A below.

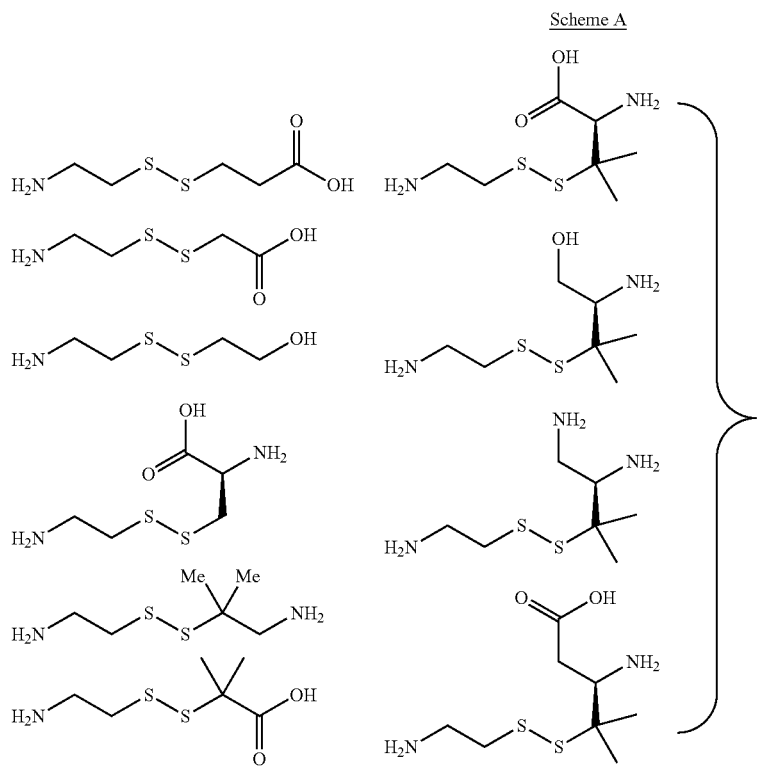
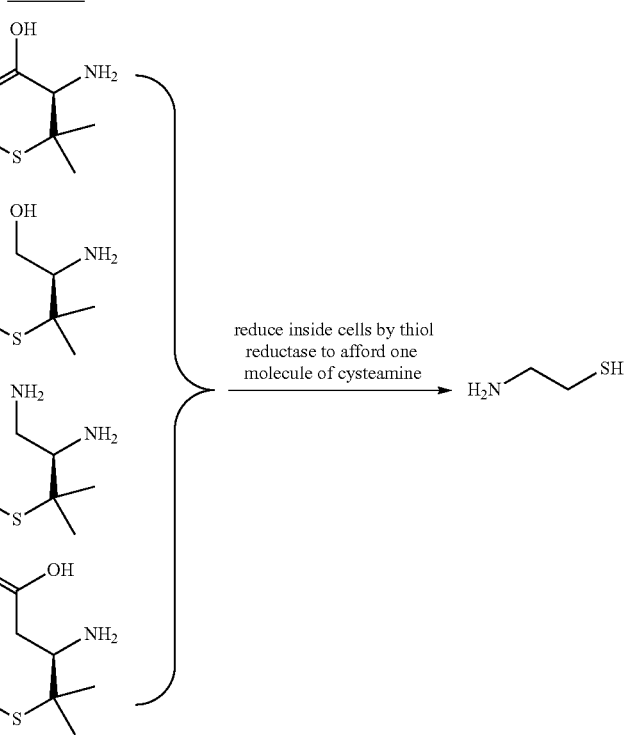

Scheme A

The term "cystic fibrosis" or "CF" refers to disorders, diseases and syndromes involving a defective CFTR. There are over 1900 mutations that may lead to CF. These mutations are further divided into 6 different classes (Class I-VI). CF can refer to any of the possible mutations that could be present in any of the 6 different classes.

As used herein, the terms "subject" and "patient" refer to the organism to be treated by the methods of the present invention. Such organisms preferably are mammals (e.g human, mouse, rat, guinea pig, dog, cat, horse, cow, pig, or non-human primate, such as a monkey, chimpanzee, baboon, rhesus, and the like), and more preferably humans.

As used herein, the term "effective amount" refers to the amount of a compound (e.g., a compound of the present invention) sufficient to effect a beneficial or desired result to a subject. An effective amount can be administered in one or more administrations, applications or dosages and is not intended to be limited to a particular formulation or administration route.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see Martin, Remington's Pharmaceutical Sciences, 15th Ed., Mack Publ. Co., Easton, Pa. [1975].

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

The term "carrier" refers to excipients and diluents, and means a material, composition or vehicle, such as a liquid or solid filler, diluent, excipient, solvent or encapsulating material, involved in administering a pharmaceutical agent to a subject or carrying or transporting a pharmaceutical agent from one organ, or portion of the body of a subject, to another organ, or portion of the body.

As used herein, the terms "treat" or "treating" includes any effect, e.g., lessening, reducing, modulating, ameliorating or eliminating, that results in the improvement of a condition, disease, disorder, and the like, or ameliorating a symptom thereof. Treating can be curing, improving, or at least partially ameliorating the disorder. In certain embodiments, treating is curing the disease.

The term "disorder" refers to, and is used interchangeably with, the terms disease, condition, or illness.

The term "prodrug" refers to a compound which is convertible in vivo by metabolic means (e.g., by hydrolysis) to a fatty acid cysteamine conjugate.

The following abbreviations are used herein and have the indicated definitions: Boc and BOC are tert-butoxycarbonyl, $Boc_2O$ is di-tert-butyl dicarbonate, BSA is bovine serum albumin, CDI is 1,1'-carbonyldiimidazole, DCC is N,N'-dicyclohexylcarbodiimide, DIEA is N,N-diisopropylethylamine, DMAP is 4-dimethylaminopyridine, DMEM is Dulbecco's Modified Eagle Medium, DMF is N,N-dimethylformamide, DOSS is sodium dioctyl sulfosuccinate, EDC and EDCI are 1-ethyl-3-(3-dimethylaminopropyl)carbodiimide hydrochloride, ELISA is enzyme-linked immunosorbent assay, EtOAc is ethyl acetate, FBS is fetal bovine serum, hr is hour, HATU is 2-(7-aza-1H-benzotriazole-1-yl)-1,1,3,3-tetramethyluronium hexafluorophosphate, HIV is human immunodeficiency virus, HPMC is hydroxypropyl methylcellulose, oxone is potassium peroxymonosulfate, Pd/C is palladium on carbon, TFA is trifluoroacetic acid, TGPS is tocopherol propylene glycol succinate, and THF is tetrahydrofuran.

Unless defined otherwise, all technical and scientific terms used herein have the same meaning as commonly understood by one of ordinary skill in the art to which this invention belongs.

Throughout the description, where compositions and kits are described as having, including, or comprising specific components, or where processes and methods are described as having, including, or comprising specific steps, it is contemplated that, additionally, there are compositions and kits of the present invention that consist essentially of, or consist of, the recited components, and that there are processes and methods according to the present invention that consist essentially of, or consist of, the recited processing steps.

As a general matter, compositions specifying a percentage are by weight unless otherwise specified. Further, if a variable is not accompanied by a definition, then the previous definition of the variable controls.

II. Fatty Acid Cysteamine Conjugates

Exemplary fatty acid cysteamine conjugates for use in the therapeutic applications and pharmaceutical compositions are described below.

Formula I

One aspect of the invention provides a compound of Formula I represented by:

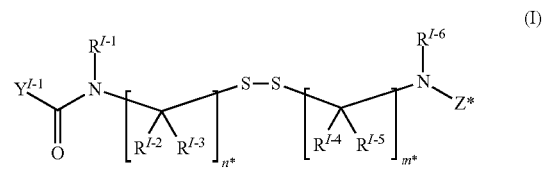

or a pharmaceutically acceptable salt or solvate thereof;
wherein:
$R^{I-1}$, $R^{I-2}$, $R^{I-3}$, $R^{I-4}$, $R^{I-5}$, and $R^{I-6}$ each represent independently for each occurrence hydrogen or $C_1$-$C_3$ alkyl;
$Y^{I-1}$ a 6-membered heteroaryl optionally substituted with 1, 2, or 3 substituents independently selected from the group consisting of alkyl, hydroxyl, alkoxyl, halogen, and acyl;
n* and m* are independently 1, 2, or 3;
Z* is

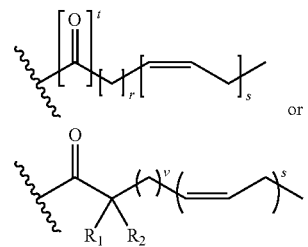

wherein:
$R_1$ and $R_2$ independently are hydrogen, $C_1$-$C_4$ alkyl, or halogen;
r is 2, 3, or 7;
s is 3, 5, or 6;
t is 0 or 1; and
v is 1, 2, or 6.

Definitions of the variables in Formula I above encompass multiple chemical groups. The application contemplates embodiments where, for example, i) the definition of a variable is a single chemical group selected from those chemical groups set forth above, ii) the definition is a collection of two or more of the chemical groups selected from those set forth above, and iii) the compound is defined by a combination of variables in which the variables are defined by (i) or (ii).

In certain embodiments, the compound is a compound of Formula I or a pharmaceutically acceptable salt thereof.

In certain embodiments, $R^{I-1}$, $R^{I-2}$, $R^{I-3}$, $R^{I-4}$, $R^{I-5}$, and $R^{I-6}$ each represent independently for each occurrence hydrogen or methyl. In certain embodiments, $R^{I-1}$, $R^{I-2}$, $R^{I-3}$, $R^{I-4}$, $R^{I-5}$, and $R^{I-6}$ are hydrogen.

In certain embodiments, $R^{I-2}$ and $R^{I-3}$ are each independently $C_1$-$C_3$ alkyl, for example, methyl. In certain embodiments, $R^{I-4}$ and $R^{I-5}$ are each independently $C_1$-$C_3$ alkyl, for example, methyl.

In certain embodiments, n* is 2. In certain embodiments, m* is 2. In certain embodiments, n* is 2, and m* is 2. In certain embodiments, n* and m* are independently 2 or 3.

In certain embodiments, both $R^{I-2}$ and $R^{I-3}$ bonded to the same carbon atom are each $C_1$-$C_3$ alkyl, for example, methyl. In certain embodiments, n* is 2, and at least one pair of $R^{I-2}$ and $R^{I-3}$ bonded to the same carbon atom are each $C_1$-$C_3$ alkyl, for example, methyl.

In certain embodiments, both $R^{I-4}$ and $R^{I-5}$ bonded to the same carbon atom are each $C_1$-$C_3$ alkyl, for example, methyl. In certain embodiments, m* is 2, and at least one pair of $R^{I-4}$ and $R^{I-5}$ bonded to the same carbon atom are each $C_1$-$C_3$ alkyl, for example, methyl.

In certain embodiments, $Y^{I-1}$ is a 6-membered heteroaryl optionally substituted with 1, 2, or 3 substituents independently selected from the group consisting of alkyl, hydroxyl, and alkoxyl. In certain embodiments, $Y^{I-1}$ is pyridinyl or pyrimidinyl, each of which is optionally substituted with 1, 2, or 3 substituents independently selected from the group consisting of alkyl, hydroxyl, and alkoxyl. In certain embodiments, Y is pyridinyl optionally substituted with 1, 2, or 3 substituents independently selected from the group consisting of alkyl, hydroxyl, and alkoxyl. In certain embodiments, $Y^{I-1}$ is pyridinyl. In certain embodiments, $Y^{I-1}$ is

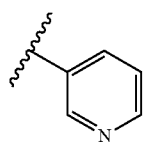 [SMILES: *c1cccnc1]

optionally substituted with 1, 2, or 3 substituents independently selected from the group consisting of alkyl, hydroxyl, and alkoxyl. In certain embodiments, $Y^{I-1}$ is

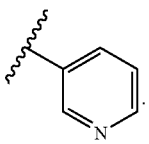

In certain embodiments, Z* is

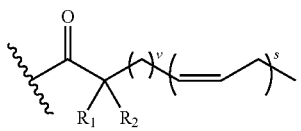

wherein $R_1$ and $R_2$ are hydrogen or methyl. In certain embodiments, $R_1$ and $R_2$ are hydrogen. In certain embodiments, Z* is one of the following:

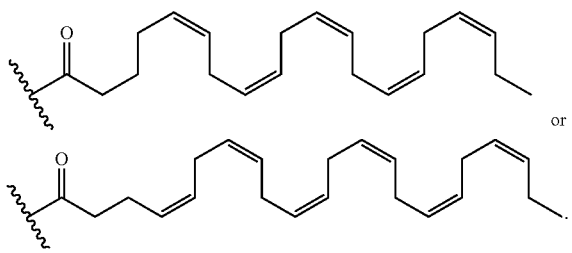

The description above describes multiple embodiments relating to compounds of Formula I. The patent application specifically contemplates all combinations of the embodiments.

Formula I-A

One aspect of the invention provides a compound of Formula I-A represented by:

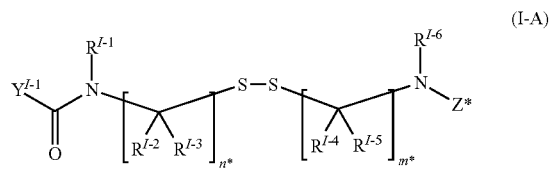

or a pharmaceutically acceptable salt or solvate thereof;
wherein:
$R^{I-1}$, $R^{I-2}$, $R^{I-3}$, $R^{I-4}$, $R^{I-5}$, and $R^{I-6}$ each represent independently for each occurrence hydrogen or $C_1$-$C_3$ alkyl;
$Y^{I-1}$ a 6-membered heteroaryl optionally substituted with 1, 2, or 3 substituents independently selected from the group consisting of alkyl, hydroxyl, alkoxyl, halogen, and acyl;
n* and m* are independently 2 or 3;
Z* is

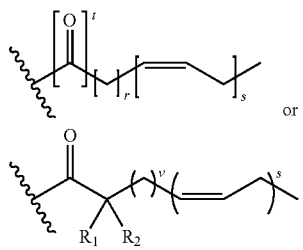

wherein:
$R_1$ and $R_2$ independently are hydrogen, $C_1$-$C_4$ alkyl, or halogen;
r is 2, 3, or 7;
s is 3, 5, or 6;
t is 0 or 1; and
v is 1, 2, or 6;
provided that when Z is

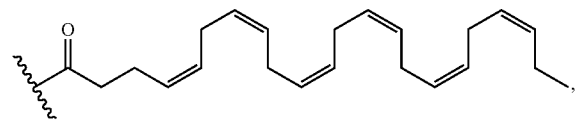 [SMILES: *C(=O)CC/C=C\C/C=C\C/C=C\C/C=C\C/C=C\C/C=C\CC]

then at least one of $R^{I-1}$, $R^{I-2}$, $R^{I-3}$, $R^{I-4}$, $R^{I-5}$, or $R^{I-6}$ is $C_1$-$C_3$ alkyl, at least one of n* or m* is 1 or 3, or $Y^{I-1}$ is other than 3-pyridinyl.

Definitions of the variables in Formula I-A above encompass multiple chemical groups. The application contemplates embodiments where, for example, i) the definition of a variable is a single chemical group selected from those chemical groups set forth above, ii) the definition is a collection of two or more of the chemical groups selected from those set forth above, and iii) the compound is defined by a combination of variables in which the variables are defined by (i) or (ii).

In certain embodiments, the compound is a compound of Formula I-A or a pharmaceutically acceptable salt thereof.

In certain embodiments, $R^{I-1}$, $R^{I-2}$, $R^{I-3}$, $R^{I-4}$, $R^{I-5}$, and $R^{I-6}$ each represent independently for each occurrence hydrogen or methyl. In certain embodiments, $R^{I-1}$, $R^{I-2}$, $R^{I-3}$, $R^{I-4}$, $R^{I-5}$, and $R^{I-6}$ are hydrogen.

In certain embodiments, $R^{I-2}$ and $R^{I-3}$ are each independently $C_1$-$C_3$ alkyl, for example, methyl. In certain embodiments, $R^{I-4}$ and $R^{I-5}$ are each independently $C_1$-$C_3$ alkyl, for example, methyl.

In certain embodiments, n* is 2. In certain embodiments, m* is 2. In certain embodiments, n* is 2, and m* is 2.

In certain embodiments, both $R^{I-2}$ and $R^{I-3}$ bonded to the same carbon atom are each $C_1$-$C_3$ alkyl, for example, methyl. In certain embodiments, n* is 2, and at least one pair of $R^{I-2}$ and $R^{I-3}$ bonded to the same carbon atom are each $C_1$-$C_3$ alkyl, for example, methyl.

In certain embodiments, both $R^{I-4}$ and $R^{I-5}$ bonded to the same carbon atom are each $C_1$-$C_3$ alkyl, for example, methyl. In certain embodiments, m* is 2, and at least one pair of $R^{I-4}$ and $R^{I-5}$ bonded to the same carbon atom are each $C_1$-$C_3$ alkyl, for example, methyl.

In certain embodiments, $Y^{I-1}$ is a 6-membered heteroaryl optionally substituted with 1, 2, or 3 substituents independently selected from the group consisting of alkyl, hydroxyl, and alkoxyl. In certain embodiments, $Y^{I-1}$ is pyridinyl or pyrimidinyl, each of which is optionally substituted with 1, 2, or 3 substituents independently selected from the group consisting of alkyl, hydroxyl, and alkoxyl. In certain embodiments, $Y^{I-1}$ is pyridinyl optionally substituted with 1, 2, or 3 substituents independently selected from the group consisting of alkyl, hydroxyl, and alkoxyl. In certain embodiments, $Y^{I-1}$ is pyridinyl. In certain embodiments, $Y^{I-1}$ is

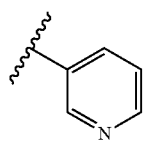 [SMILES: *c1cccnc1]

optionally substituted with 1, 2, or 3 substituents independently selected from the group consisting of alkyl, hydroxyl, and alkoxyl. In certain embodiments, $Y^{I-1}$ is

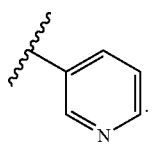

In certain embodiments, Z* is

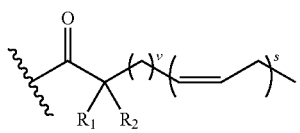

wherein $R_1$ and $R_2$ are hydrogen or methyl. In certain embodiments, $R_1$ and $R_2$ are hydrogen. In certain embodiments, Z* is one of the following:

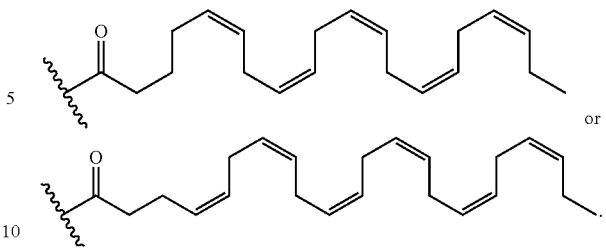

The description above describes multiple embodiments relating to compounds of Formula I-A. The patent application specifically contemplates all combinations of the foregoing embodiments.

Formula I-B

Another aspect of the invention provides a compound of Formula I-B represented by:

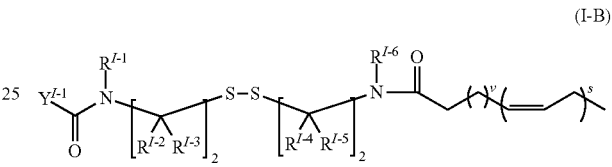

(I-B)

or a pharmaceutically acceptable salt thereof; wherein:
$R^{I-1}$, $R^{I-2}$, $R^{I-3}$, $R^{I-4}$, $R^{I-5}$, and $R^{I-6}$ each represent independently for each occurrence hydrogen or $C_1$-$C_3$ alkyl;

$Y^{I-1}$ is a 6-membered heteroaryl optionally substituted with 1, 2, or 3 substituents independently selected from the group consisting of alkyl, hydroxyl, alkoxyl, halogen, and acyl;

s is 3, 5, or 6; and v is 1 or 2.

Definitions of the variables in Formula I-B above encompass multiple chemical groups. The application contemplates embodiments where, for example, i) the definition of a variable is a single chemical group selected from those chemical groups set forth above, ii) the definition is a collection of two or more of the chemical groups selected from those set forth above, and iii) the compound is defined by a combination of variables in which the variables are defined by (i) or (ii). In certain embodiments, the compound is a compound of Formula I-B or a pharmaceutically acceptable salt thereof.

In certain embodiments, $R^{I-1}$, $R^{I-2}$, $R^{I-3}$, $R^{I-4}$, $R^{I-5}$, and $R^{I-6}$ each represent independently for each occurrence hydrogen or methyl. In certain embodiments, $R^{I-1}$, $R^{I-2}$, $R^{I-3}$, $R^{I-4}$, $R^{I-5}$, and $R^{I-6}$ are hydrogen.

In certain embodiments, both $R^{I-2}$ and $R^{I-3}$ bonded to the same carbon atom are each $C_1$-$C_3$ alkyl, for example, methyl. In certain embodiments, n* is 2, and at least one pair of $R^{I-2}$ and $R^{I-3}$ bonded to the same carbon atom are each $C_1$-$C_3$ alkyl, for example, methyl.

In certain embodiments, both $R^{I-4}$ and $R^{I-5}$ bonded to the same carbon atom are each $C_1$-$C_3$ alkyl, for example, methyl. In certain embodiments, m* is 2, and at least one pair of $R^{I-4}$ and $R^{I-5}$ bonded to the same carbon atom are each $C_1$-$C_3$ alkyl, for example, methyl.

In certain embodiments, $Y^{I-1}$ is a 6-membered heteroaryl optionally substituted with 1, 2, or 3 substituents independently selected from the group consisting of alkyl, hydroxyl, and alkoxyl. In certain embodiments, $Y^{I-1}$ is pyridinyl or pyrimidinyl, each of which is optionally substituted with 1, 2, or 3 substituents independently selected from the group consisting of alkyl, hydroxyl, and alkoxyl. In certain embodiments, $Y^{I-1}$ is pyridinyl optionally substituted with 1, 2, or 3 substituents independently selected from the group consisting of alkyl, hydroxyl, and alkoxyl. In certain embodiments, $Y^{I-1}$ is pyridinyl. In certain embodiments, $Y^{I-1}$ is

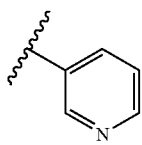 [SMILES: *c1cccnc1]

optionally substituted with 1, 2, or 3 substituents independently selected from the group consisting of alkyl, hydroxyl, and alkoxyl. In certain embodiments, $Y^{I-1}$ is

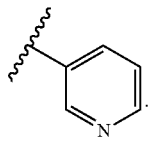

The description above describes multiple embodiments relating to compounds of Formula I-B. The patent application specifically contemplates all combinations of the foregoing embodiments.

Additional Fatty Acid Cysteamine Conjugates

Another aspect of the invention provides a molecular conjugate comprising cysteamine covalently linked via a linker to a fatty, wherein the fatty acid is selected from the group consisting of omega-3 fatty acids and fatty acids that are metabolized in vivo to omega-3 fatty acids. The conjugate is capable of intracellular hydrolysis to produce free cysteamine and free fatty acid.

In certain embodiments, the fatty acid is selected from the group consisting of all-cis-7,10,13-hexadecatrienoic acid, α-linolenic acid, stearidonic acid, eicosatrienoic acid, eicosatetraenoic acid, eicosapentaenoic acid (EPA), docosapentaenoic acid, docosahexaenoic acid (DHA), tetracosapentaenoic acid and tetracosahexaenoic acid. In other embodiments, the fatty acid is selected from eicosapentaenoic acid and docosahexaenoic acid. In other embodiments, the fatty acid is selected from eicosapentaenoic acid and docosahexaenoic acid. In some embodiments, the fatty acid is eicosapentaenoic acid (EPA). In other embodiments, the fatty acid is docosahexaenoic acid (DHA). In some embodiments, the hydrolysis is enzymatic.

Formula II

Another aspect of the invention provides a compound of Formula II:

Formula II or a pharmaceutically acceptable salt or solvate thereof; wherein:
Z is

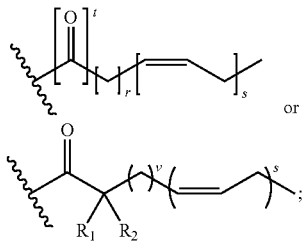

wherein
each t independently is 0 or 1;
each r independently is 2, 3, or 7;
each s independently is 3, 5, or 6;
each v independently is 1, 2, or 6;
$R_1$ and $R_2$ independently are selected from the group consisting of —H, -D, —$C_1$-$C_4$ alkyl, -halogen, —OH, —C(O)$C_1$-$C_4$ alkyl, —O-aryl, —O-benzyl, —OC(O)$C_1$-$C_4$ alkyl, —$C_2$-$C_3$ alkenyl, —$C_2$-$C_3$ alkynyl, —C(O)$C_1$-$C_4$ alkyl, —NH$_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, and —S(O)$_2$$C_1$-$C_3$ alkyl;
$R_3$ and $R_4$ independently are H or

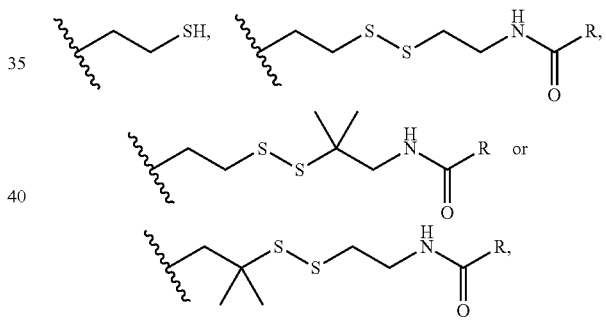

provided that at least one of $R_3$ and $R_4$ is

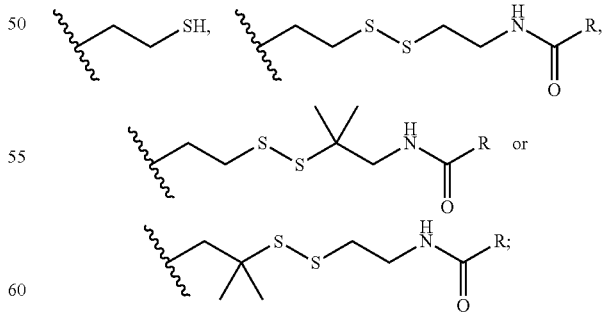

each R independently is heteroaryl optionally substituted with one, two, three, four or five groups selected from OH, CN, halogen, —CO$_2$R$_6$, —CONHR$_6$, —CONR$_6$R$_6$, —S(O)$_2$NR$_6$R$_6$, —NR$_6$R$_6$, —NR$_6$COR$_6$, or —(OCH$_2$CH$_2$)$_m$—OCH$_3$;

each $R_6$ independently is —H, $C_1$-$C_3$ alkyl, or straight or branched $C_1$-$C_4$ alkyl optionally substituted with OH or halogen; and m is 1 or 2.

It is also understood in Formula II that a methyl substituent can be substituted with a $C_1$-$C_6$ alkyl.

In certain embodiments, Z is

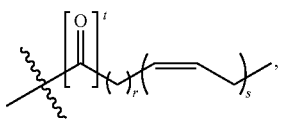

wherein r is 2, and s is 6.

In certain embodiments, Z is

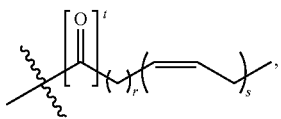

wherein r is 3, and s is 5.

In certain embodiments, Z is

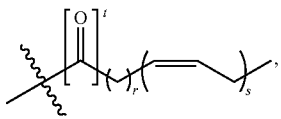

wherein r is 7, and s is 3.

In certain embodiments, Z is

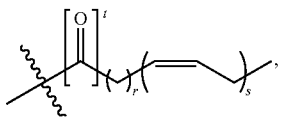

wherein t is 1, and
  r is 3 and s is 5, or
  r is 2 and s is 6, or
  r is 7 and s is 3.

In certain embodiments, Z is

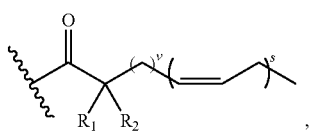

wherein v is 1, and s is 6.

In certain embodiments, Z is

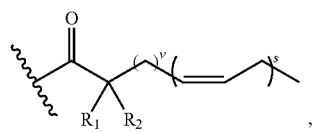

wherein v is 2, and s is 5.

In certain embodiments, Z is

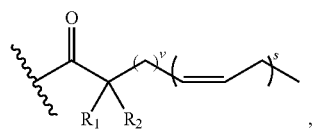

wherein v is 6 and s is 3.

In certain embodiments, Z is defined by one of the above embodiments where $R_1$ and $R_2$ are hydrogen.

Formula III

Another aspect of the invention provides a compound of the Formula III:

Formula III

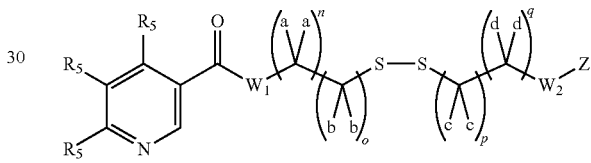

or a pharmaceutically acceptable salt or solvate thereof; wherein $W_1$ and $W_2$ independently is NR;

each R is independently H, —$C_1$-$C_3$ alkyl, phenyl, benzyl, —$CH_2CO_2R_3$, —$CH_2CONR_3R_3$ or straight or branched $C_1$-$C_4$ alkyl optionally substituted with OH or halogen;

$R_5$ independently is selected from the group consisting of —H, -D, —Cl, —F, —CN, —$NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —C(O)H, —C(O)$C_1$-$C_3$ alkyl, —C(O)O$C_1$-$C_3$ alkyl, —C(O)$NH_2$, —C(O)NH($C_1$-$C_3$ alkyl), —C(O)N($C_1$-$C_3$ alkyl)$_2$, —$C_1$-$C_3$ alkyl, —O—$C_1$-$C_3$ alkyl, —S(O)$C_1$-$C_3$ alkyl and —$S(O)_2C_1$-$C_3$ alkyl;

each a, b, c, and d independently is H, -D, —$CH_3$, —$OCH_3$, —$OCH_2CH_3$, —C(O)OR, or benzyl, or two of a, b, c, and d can be taken together, along with the single carbon to which they are bound, to form a cycloalkyl or heterocycle;

each n, o, p, and q is independently 0 or 1;

each Z independently is

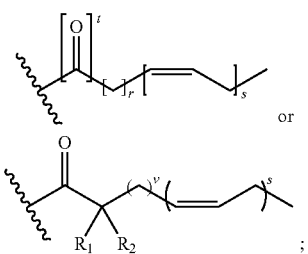

each r independently is 2, 3, or 7;
each s independently is 3, 5, or 6;
each t independently is 0 or 1;
each v independently is 1, 2, or 6;

$R_1$ and $R_2$ independently are each H, D, —$C_1$-$C_4$ alkyl, -halogen, —OH, —C(O)$C_1$-$C_4$ alkyl, —O-aryl, —O-benzyl, —OC(O)$C_1$-$C_4$ alkyl, —$C_2$-$C_3$ alkenyl, —$C_2$-$C_3$ alkynyl, —C(O)$C_1$-$C_4$ alkyl, —$NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl;

each $R_3$ is independently H or $C_1$-$C_6$ alkyl, or two $R_3$ groups, when taken together with the nitrogen to which they are attached, can form a heterocycle; provided that when Z is

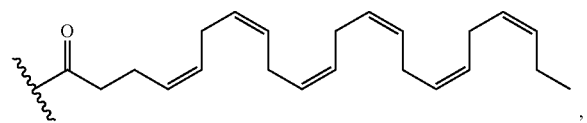 [SMILES: *C(=O)CC/C=C\C/C=C\C/C=C\C/C=C\C/C=C\C/C=C\CC]

then at least one of a, b, c or d is $C_1$-$C_3$ alkyl, at least one of the aggregate of (i) n and o or (ii) p and q is 1 or 3, or the N containing heterocycle is other than 3-pyridinyl.

Formula III-A

Another aspect of the invention provides a compound of the Formula III-A:

Formula III-A

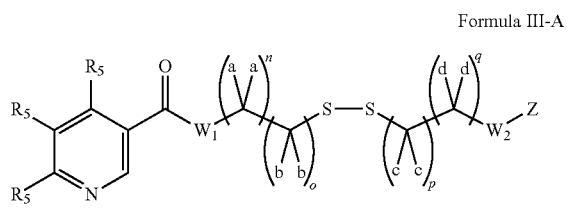

or a pharmaceutically acceptable salt or solvate thereof; wherein $W_1$ and $W_2$ independently is NR;

each R is independently H, —$C_1$-$C_3$ alkyl, phenyl, benzyl, —$CH_2CO_2R_3$, —$CH_2CONR_3R_3$ or straight or branched $C_1$-$C_4$ alkyl optionally substituted with OH or halogen;

$R_5$ independently is selected from the group consisting of —H, -D, —Cl, —F, —CN, —$NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —C(O)H, —C(O)$C_1$-$C_3$ alkyl, —C(O)O$C_1$-$C_3$ alkyl, —C(O)$NH_2$, —C(O)NH($C_1$-$C_3$ alkyl), —C(O)N($C_1$-$C_3$ alkyl)$_2$, —$C_1$-$C_3$ alkyl, —O—$C_1$-$C_3$ alkyl, —S(O)$C_1$-$C_3$ alkyl and —S(O)$_2$$C_1$-$C_3$ alkyl;

each a, b, c, and d independently is H, -D, —$CH_3$, —$OCH_3$, —$OCH_2CH_3$, —C(O)OR, or benzyl, or two of a, b, c, and d can be taken together, along with the single carbon to which they are bound, to form a cycloalkyl or heterocycle;

each n, o, p, and q is independently 0 or 1;
each Z independently is

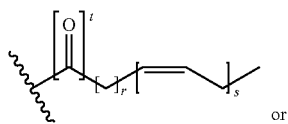 or

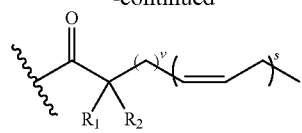;

each r independently is 2, 3, or 7;
each s independently is 3, 5, or 6;
each t independently is 0 or 1;
each v independently is 1, 2, or 6;

$R_1$ and $R_2$ independently are each H, D, —$C_1$-$C_4$ alkyl, -halogen, —OH, —C(O)$C_1$-$C_4$ alkyl, —O-aryl, —O-benzyl, —OC(O)$C_1$-$C_4$ alkyl, —$C_2$-$C_3$ alkenyl, —$C_2$-$C_3$ alkynyl, —C(O)$C_1$-$C_4$ alkyl, —$NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —SH, —S($C_1$-$C_3$ alkyl), —S(O)$C_1$-$C_3$ alkyl, —S(O)$_2$$C_1$-$C_3$ alkyl;

each $R_3$ is independently H or $C_1$-$C_6$ alkyl, or two $R_3$ groups, when taken together with the nitrogen to which they are attached, can form a heterocycle.

Definitions of the variables in Formula III or Formula III-A above encompass multiple chemical groups. The application contemplates embodiments where, for example, i) the definition of a variable is a single chemical group selected from those chemical groups set forth above, ii) the definition is a collection of two or more of the chemical groups selected from those set forth above, and iii) the compound is defined by a combination of variables in which the variables are defined by (i) or (ii). For a compound of each of Formula III and Formula III-A, each of the following embodiments apply equally.

In certain embodiments, at least one $R_5$ is Cl or F. In certain embodiments, each $R_5$ independently is —H.

In certain embodiments, R of $W_1$ is H or $C_1$-$C_4$ alkyl.

In certain embodiment, R of $W_2$ is H or $C_1$-$C_4$ alkyl.

In certain embodiments, a and c are each independently H, $CH_3$, —$OCH_3$, —$OCH_2CH_3$, or C(O)OR.

In certain embodiments n, o, p, and q are each 1. In certain embodiments, two of n, o, p, and q are each 1. In certain embodiments, three of n, o, p, and q are each 1.

In certain embodiments, Z is

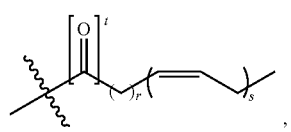, wherein r is 2, and s is 5.

In certain embodiments, Z is

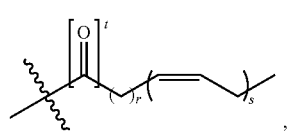, wherein r is 3, and s is 5.

In certain embodiments, Z is

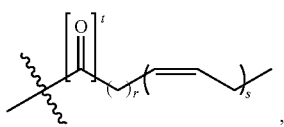

wherein r is 7, and s is 3.

In certain embodiments, Z is

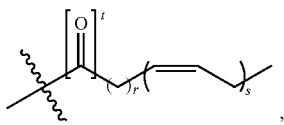

wherein t is 1, and
r is 3 and s is 5, or
r is 2 and s is 6, or
r is 7 and s is 3.

In certain embodiments, Z is

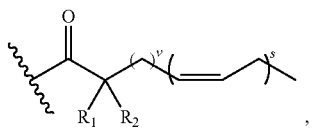

wherein v is 1, and s is 6.

In certain embodiments, Z is

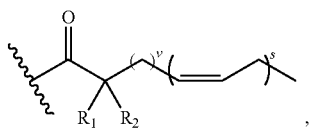

wherein v is 2, and s is 5.

In certain embodiments, Z is

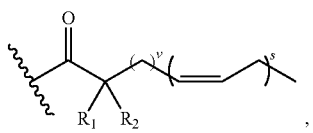

wherein v is 6, and s is 3.

Formula IV

Another aspect of the invention provides a compound of the Formula IV:

or a pharmaceutically acceptable salt or solvate thereof; wherein $W_1$ is NR;

R independently is H, —$C_1$-$C_3$ alkyl, phenyl, benzyl, —$CH_2CO_2R_3$, —$CH_2CONR_3R_3$ or straight or branched $C_1$-$C_4$ alkyl optionally substituted with OH or halogen;

$R^5$ independently is selected from the group consisting of —H, -D, —Cl, —F, —CN, —$NH_2$, —NH($C_1$-$C_3$ alkyl), —N($C_1$-$C_3$ alkyl)$_2$, —NH(C(O)$C_1$-$C_3$ alkyl), —N(C(O)$C_1$-$C_3$ alkyl)$_2$, —C(O)H, —C(O)$C_1$-$C_3$ alkyl, —C(O)O$C_1$-$C_3$ alkyl, —C(O)$NH_2$, —C(O)NH($C_1$-$C_3$ alkyl), —C(O)N($C_1$-$C_3$ alkyl)$_2$, —$C_1$-$C_3$ alkyl, —O—$C_1$-$C_3$ alkyl, —S(O)$C_1$-$C_3$ alkyl and —S(O)$_2$$C_1$-$C_3$ alkyl;

$R^{I-2}$, $R^{I-3}$, $R^{I-4}$, $R^{I-5}$, and $R^{I-6}$ each represent independently for each occurrence hydrogen or $C_1$-$C_3$ alkyl;

Z* is

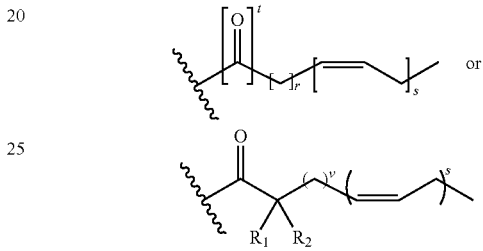

wherein:

$R_1$ and $R_2$ independently are hydrogen, $C_1$-$C_4$ alkyl, or halogen;

r is 2, 3, or 7;
s is 3, 5, or 6;
t is 0 or 1; and
v is 1, 2, or 6;
m* is 2 or 3;
o* is 1 or 2;
p* is 1 or 2;
$R^{I-7}$ and $R^{I-8}$ are each independently H or

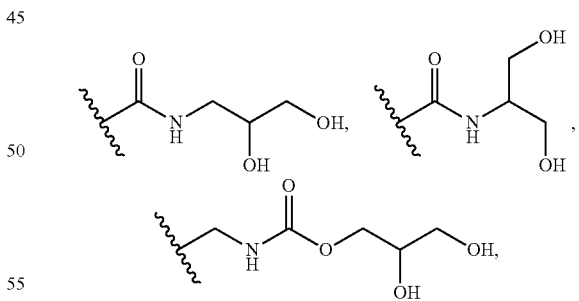

Formula IV

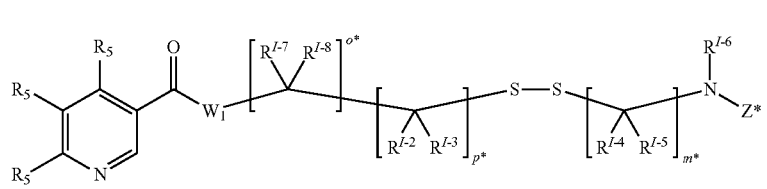

-continued

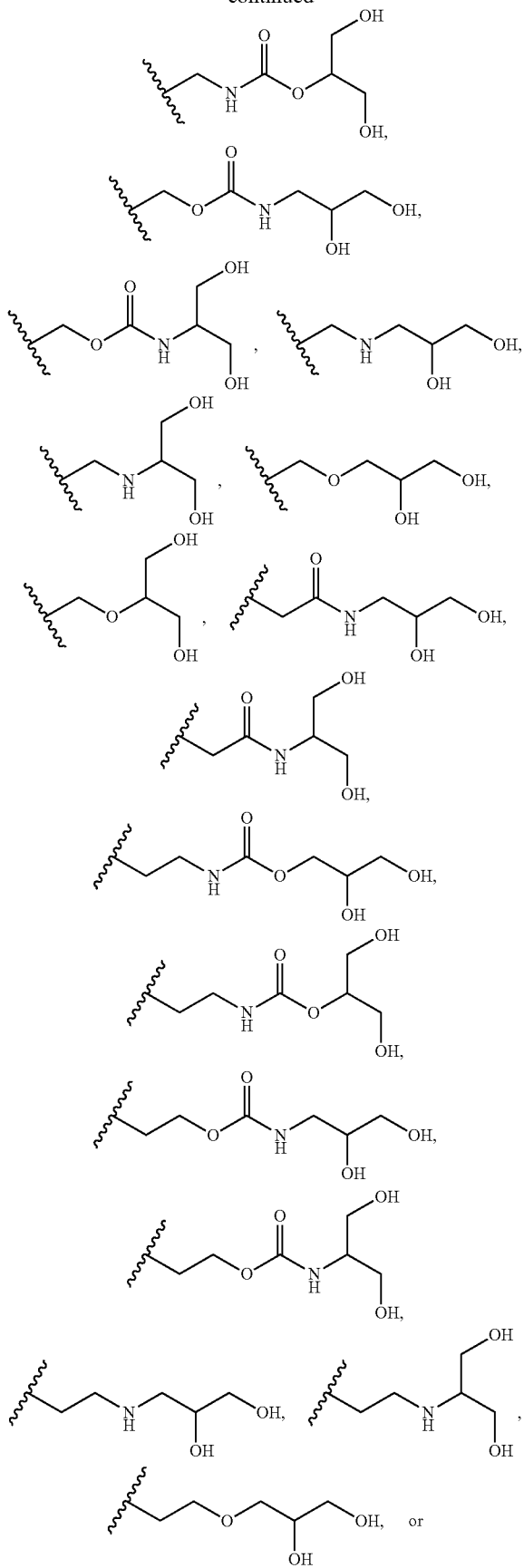

-continued

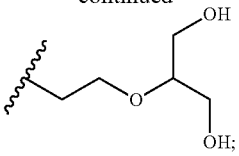

optionally provided that, when Z is

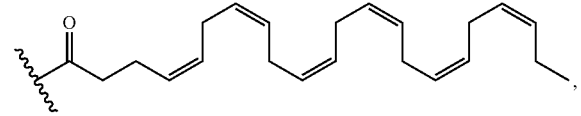 [SMILES: *C(=O)CC/C=C\C/C=C\C/C=C\C/C=C\C/C=C\C/C=C\CC]

then at least one of $R^{I-2}$, $R^{I-3}$, $R^{I-4}$, $R^{I-5}$, or $R^{I-6}$ is $C_1$-$C_3$ alkyl, or $R^{I-7}$ and $R^{I-8}$ is not hydrogen, or at least one of (i) m* or (ii) the aggregate of o* and p*, is 1 or 3, or the N containing heterocycle is other than 3-pyridinyl. In certain circumstances, for example, in connection with the uses contemplated herein, the foregoing proviso is unnecessary.

Definitions of the variables in Formula IV above encompass multiple chemical groups. The application contemplates embodiments where, for example, i) the definition of a variable is a single chemical group selected from those chemical groups set forth above, ii) the definition is a collection of two or more of the chemical groups selected from those set forth above, and iii) the compound is defined by a combination of variables in which the variables are defined by (i) or (ii).

In certain embodiments, at least one $R_5$ is Cl or F. In certain embodiments, each $R_5$ independently is —H.

In certain embodiments, R of $W_1$ is hydrogen or $C_1$-$C_4$ alkyl.

In certain embodiments, $R^{I-2}$, $R^{I-3}$, $R^{I-4}$, $R^{I-5}$, and $R^{I-6}$ each represent independently for each recurrence hydrogen or methyl. In certain embodiments, $R^{I-2}$, $R^{I-3}$, $R^{I-4}$, $R^{I-5}$, and $R^{I-6}$ are hydrogen.

In certain embodiments, m* is 2. In certain embodiments, p* is 2 and o* is 0. In certain embodiments, p* is 1 and o* is 1.

In certain embodiments, both $R^{I-2}$ and $R^{I-3}$ bonded to the same carbon atom are each $C_1$-$C_3$ alkyl, for example, methyl. In certain embodiment, p* is 1 or 2, and at least one pair of $R^{I-2}$ and $R^{I-3}$ bonded to the same carbon atom are each $C_1$-$C_3$ alkyl, for example, methyl.

In certain embodiments, Z is

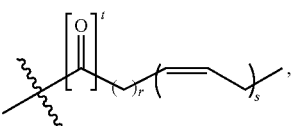

wherein r is 2, and s is 6.

In certain embodiments, Z is

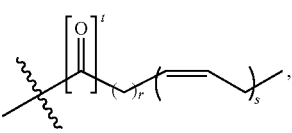

wherein r is 3, and s is 5.
 In certain embodiments, Z is

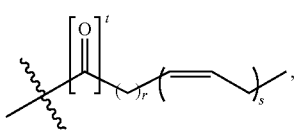

wherein r is 7, and s is 3.
 In certain embodiments, Z is

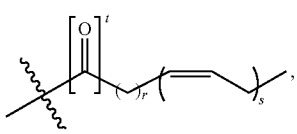

wherein t is 1, and
 r is 3 and s is 5, or
 r is 2 and s is 6, or
 r is 7 and s is 3.
 In certain embodiments, Z is

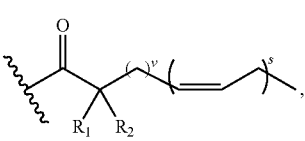

wherein v is 1, and s is 6.
 In certain embodiments, Z is

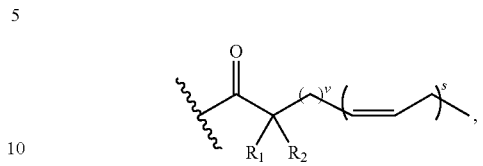

wherein v is 2, and s is 5.
 In certain embodiments, Z is

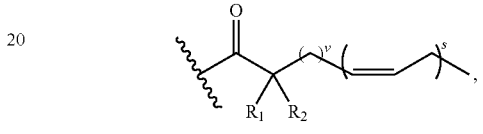

wherein v is 6, and s is 3.

In each of Formula I, IA, IB, II, III, III-A, or IV any one or more of the H atoms may be substituted with a deuterium.

Exemplary Specific Compounds

In certain embodiments, the compound is one of the following or a pharmaceutically acceptable salt thereof:

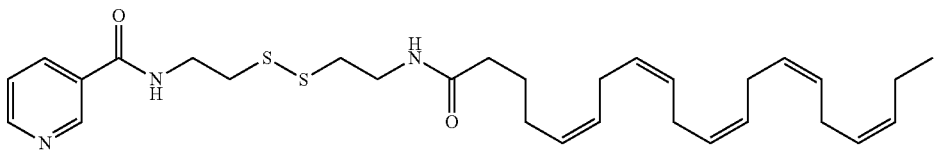 [SMILES: CC/C=C\C/C=C\C/C=C\C/C=C\C/C=C\CCCC(=O)NCCSSCCNC(=O)c1cccnc1]

N-(2-((2-((5Z,8Z,11Z,14Z,17Z)-icosa-5,8,11,14,17-pentaenamido)ethyl)disulfanyl)ethyl)nicotinamide (II-2),

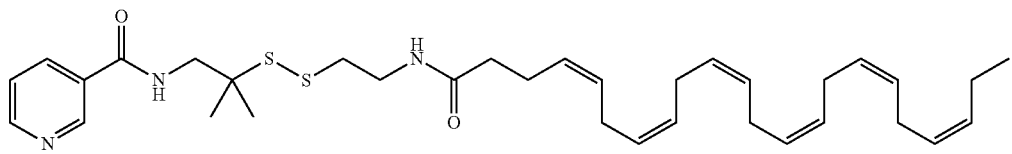 [SMILES: CC/C=C\C/C=C\C/C=C\C/C=C\C/C=C\C/C=C\CCC(=O)NCCSSC(C)(C)CNC(=O)c1cccnc1]

N-(2-((2-((4Z,7Z,10Z,13Z,16Z,19Z)-docosa-4,7,10,13,16,19-hexaenamido)ethyl)disulfanyl)-2-methylpropyl)nicotinamide (II-3),

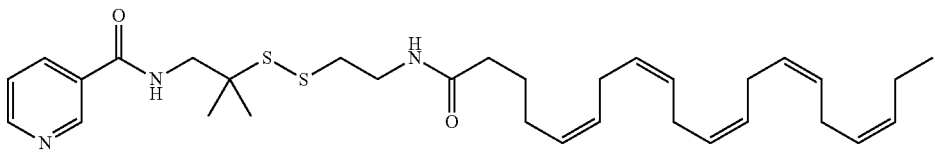 [SMILES: CC/C=C\C/C=C\C/C=C\C/C=C\C/C=C\CCCC(=O)NCCSSC(C)(C)CNC(=O)c1cccnc1]

N-(2-((2-((5Z,8Z,11Z,14Z,17Z)-icosa-5,8,11,14,17-pentae-
namido)ethyl)disulfanyl)-2-methylpropyl)nicotinamide
(II-4),

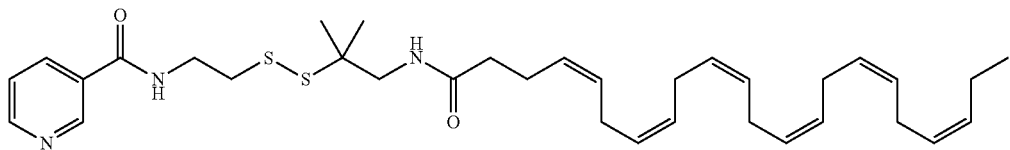 [SMILES: CC/C=C\C/C=C\C/C=C\C/C=C\C/C=C\C/C=C\CCC(=O)NCC(C)(C)SSCCNC(=O)c1cccnc1]

N-(2-((1-((4Z,7Z,10Z,13Z,16Z,19Z)-docosa-4,7,10,13,16,
19-hexaenamido)-2-methylpropan-2-yl)disulfanyl)ethyl)
nicotinamide (II-5),

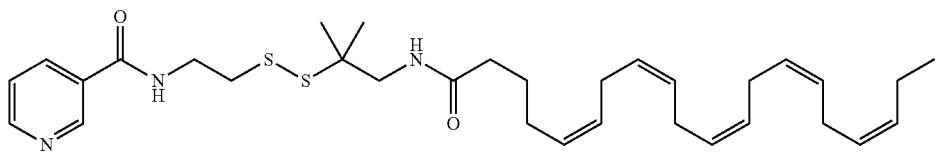 [SMILES: CC/C=C\C/C=C\C/C=C\C/C=C\C/C=C\CCCC(=O)NCC(C)(C)SSCCNC(=O)c1cccnc1]

N-(2-((1-((5Z,8Z,11Z,14Z,17Z)-icosa-5,8,11,14,17-pentae-
namido)-2-methylpropan-2-yl)disulfanyl)ethyl)nicotina-
mide (II-6),

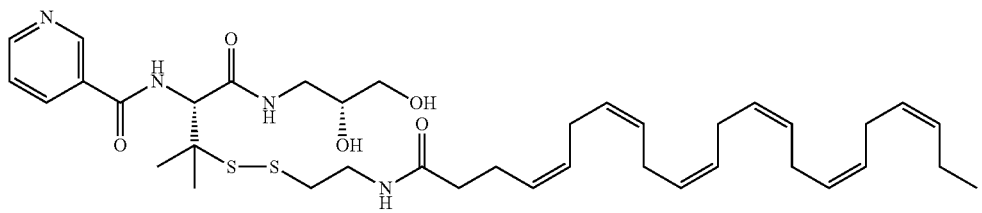 [SMILES: CC/C=C\C/C=C\C/C=C\C/C=C\C/C=C\C/C=C\CCC(=O)NCCSSC(C)(C)[C@H](NC(=O)c1cccnc1)C(=O)NC[C@@H](O)CO]

N—((R)-1-(((R)-2,3-dihydroxypropyl)amino)-3-((2-((4Z,
7Z,10Z,13Z,16Z,19Z)-docosa-4,7,10,13,16,19-hexaena-
mido)ethyl)disulfanyl)-3-methyl-1-oxobutan-2-yl)nicoti-
namide (IV-1),

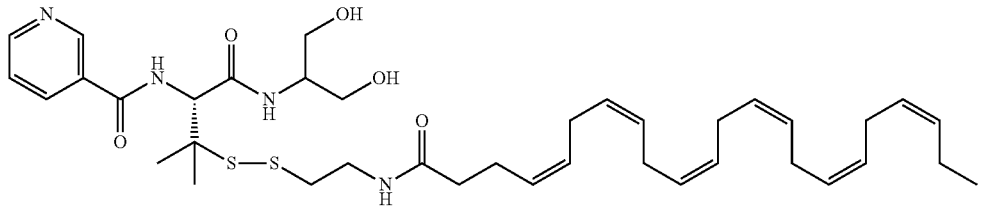 [SMILES: CC/C=C\C/C=C\C/C=C\C/C=C\C/C=C\C/C=C\CCC(=O)NCCSSC(C)(C)[C@H](NC(=O)c1cccnc1)C(=O)NC(CO)CO]

N—((R)-1-((1,3-dihydroxypropan-2-yl)amino)-3-((2-((4Z,
7Z,10Z,13Z,16Z,19Z)-docosa-4,7,10,13,16,19-hexaena-
mido)ethyl)disulfanyl)-3-methyl-1-oxobutan-2-yl)nicoti-
namide (IV-2),

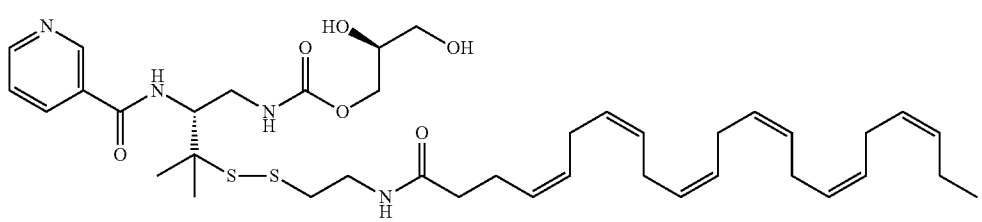 [SMILES: CC/C=C\C/C=C\C/C=C\C/C=C\C/C=C\C/C=C\CCC(=O)NCCSSC(C)(C)[C@@H](CNC(=O)OC[C@@H](O)CO)NC(=O)c1cccnc1]

(S)-2,3-dihydroxypropyl ((R)-3-((2-((4Z,7Z,10Z,13Z,16Z,
19Z)-docosa-4,7,10,13,16,19-hexaenamido)ethyl)disul-
fanyl)-3-methyl-2-(nicotinamido)butyl)carbamate (IV-3),

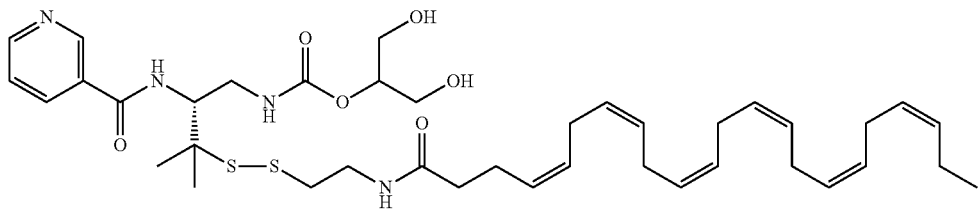 [SMILES: CC/C=C\C/C=C\C/C=C\C/C=C\C/C=C\C/C=C\CCC(=O)NCCSSC(C)(C)[C@@H](CNC(=O)OC(CO)CO)NC(=O)c1cccnc1]

1,3-dihydroxypropan-2-yl ((R)-3-((2-((4Z,7Z,10Z,13Z,16Z,
19Z)-docosa-4,7,10,13,16,19-hexaenamido)ethyl)disul-
fanyl)-3-methyl-2-(nicotinamido)butyl)carbamate (IV-4),

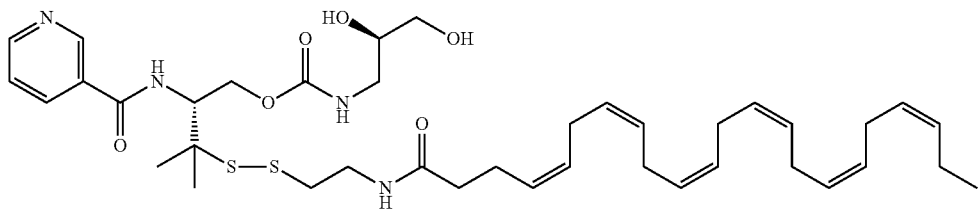 [SMILES: CC/C=C\C/C=C\C/C=C\C/C=C\C/C=C\C/C=C\CCC(=O)NCCSSC(C)(C)[C@@H](COC(=O)NC[C@@H](O)CO)NC(=O)c1cccnc1]

(R)-3-((2-((4Z,7Z,10Z,13Z,16Z,19Z)-docosa-4,7,10,13,16,
19-hexaenamido)ethyl)disulfanyl)-3-methyl-2-(nicotina-
mido)butyl ((R)-2,3-dihydroxypropyl)carbamate (IV-5),

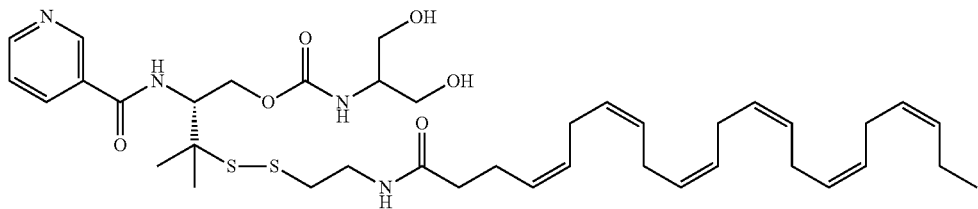 [SMILES: CC/C=C\C/C=C\C/C=C\C/C=C\C/C=C\C/C=C\CCC(=O)NCCSSC(C)(C)[C@@H](COC(=O)NC(CO)CO)NC(=O)c1cccnc1]

(R)-3-((2-((4Z,7Z,10Z,13Z,16Z,19Z)-docosa-4,7,10,13,16,
19-hexaenamido)ethyl)disulfanyl)-3-methyl-2-(nicotina-
mido)butyl (1,3-dihydroxypropan-2-yl)carbamate (IV-6),

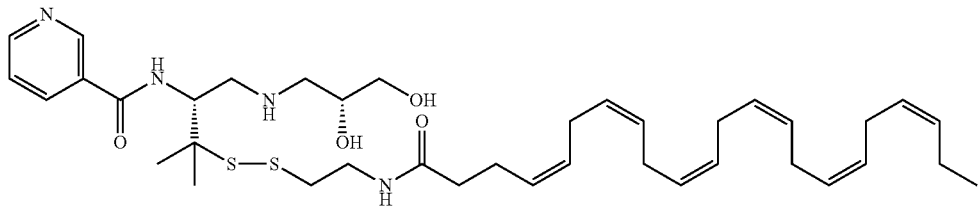

N—((R)-1-(((R)-2,3-dihydroxypropyl)amino)-3-((2-((4Z,
7Z,10Z,13Z,16Z,19Z)-docosa-4,7,10,13,16,19-hexaena-
mido)ethyl)disulfanyl)-3-methylbutan-2-yl)nicotinamide
(IV-7),

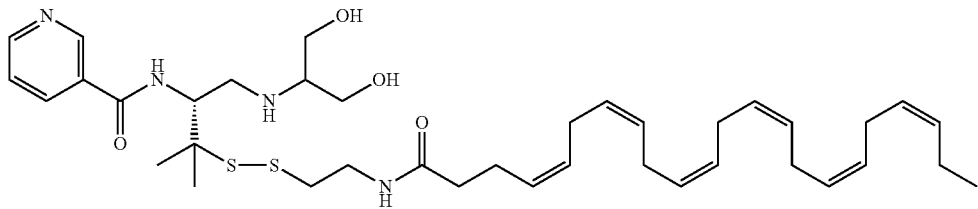 [SMILES: CC/C=C\C/C=C\C/C=C\C/C=C\C/C=C\C/C=C\CCC(=O)NCCSSC(C)(C)[C@@H](CNC(CO)CO)NC(=O)c1cccnc1]

N—((R)-1-((1,3-dihydroxypropan-2-yl)amino)-3-((2-((4Z,7Z,10Z,13Z,16Z,19Z)-docosa-4,7,10,13,16,19-hexaenamido)ethyl)disulfanyl)-3-methylbutan-2-yl)nicotinamide (IV-8),

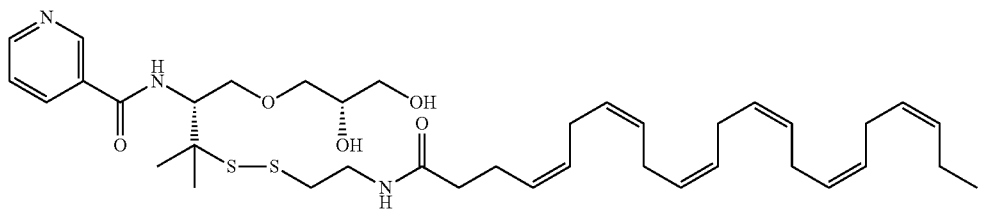 [SMILES: CC/C=C\C/C=C\C/C=C\C/C=C\C/C=C\C/C=C\CCC(=O)NCCSSC(C)(C)[C@@H](COC[C@@H](O)CO)NC(=O)c1cccnc1]

N—((R)-1-((S)-2,3-dihydroxypropoxy)-3-((2-((4Z,7Z,10Z,13Z,16Z,19Z)-docosa-4,7,10,13,16,19-hexaenamido)ethyl)disulfanyl)-3-methylbutan-2-yl)nicotinamide (IV-9),

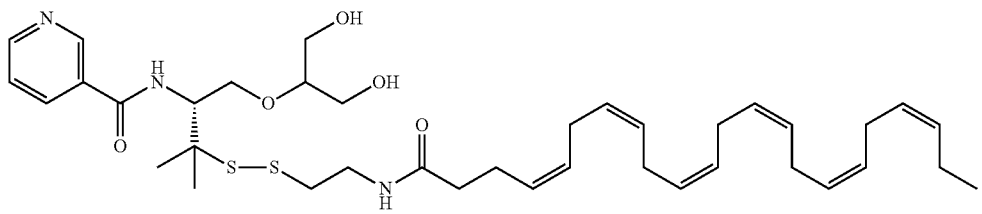 [SMILES: CC/C=C\C/C=C\C/C=C\C/C=C\C/C=C\C/C=C\CCC(=O)NCCSSC(C)(C)[C@@H](COC(CO)CO)NC(=O)c1cccnc1]

N—((R)-1-((1,3-dihydroxypropan-2-yl)oxy)-3-((2-((4Z,7Z,10Z,13Z,16Z,19Z)-docosa-4,7,10,13,16,19-hexaenamido)ethyl)disulfanyl)-3-methylbutan-2-yl)nicotinamide (IV-10),

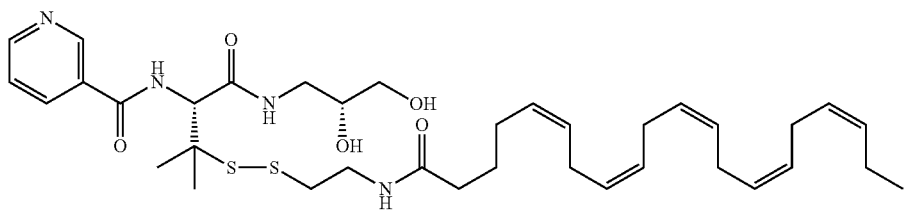 [SMILES: CC/C=C\C/C=C\C/C=C\C/C=C\C/C=C\CCCC(=O)NCCSSC(C)(C)[C@H](NC(=O)c1cccnc1)C(=O)NC[C@@H](O)CO]

N—((R)-1-(((R)-2,3-dihydroxypropyl)amino)-3-((2-((5Z,8Z,11Z,14Z,17Z)-icosa-5,8,11,14,17-pentaenamido)ethyl)disulfanyl)-3-methyl-1-oxobutan-2-yl)nicotinamide (IV-11),

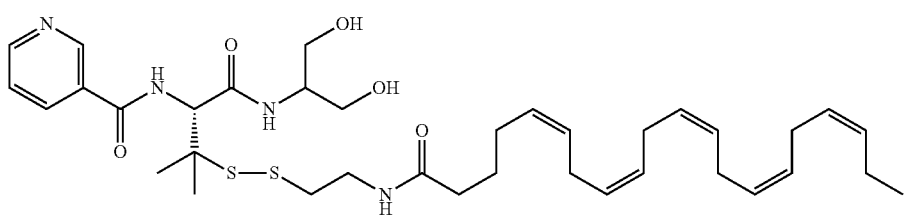 [SMILES: CC/C=C\C/C=C\C/C=C\C/C=C\C/C=C\CCCC(=O)NCCSSC(C)(C)[C@H](NC(=O)c1cccnc1)C(=O)NC(CO)CO]

N—((R)-1-((1,3-dihydroxypropan-2-yl)amino)-3-((2-((5Z,8Z,11Z,14Z,17Z)-icosa-5,8,11,14,17-pentaenamido)ethyl)disulfanyl)-3-methyl-1-oxobutan-2-yl)nicotinamide (IV-12),

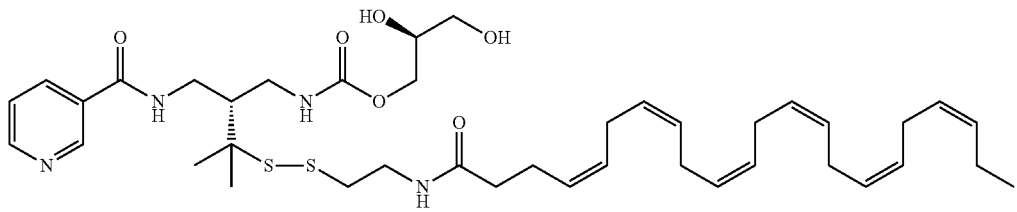 [SMILES: CC/C=C\C/C=C\C/C=C\C/C=C\C/C=C\C/C=C\CCC(=O)NCCSSC(C)(C)[C@@H](CNC(=O)OC[C@@H](O)CO)CNC(=O)c1cccnc1]

(S)-2,3-dihydroxypropyl ((R)-3-((2-((4Z,7Z,10Z,13Z,16Z,19Z)-docosa-4,7,10,13,16,19-hexaenamido)ethyl)disulfanyl)-3-methyl-2-(nicotinamidomethyl)butyl)carbamate (IV-13),

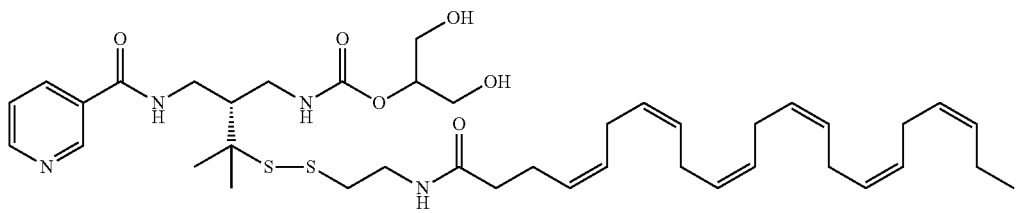 [SMILES: CC/C=C\C/C=C\C/C=C\C/C=C\C/C=C\C/C=C\CCC(=O)NCCSSC(C)(C)[C@@H](CNC(=O)OC(CO)CO)CNC(=O)c1cccnc1]

1,3-dihydroxypropan-2-yl ((R)-3-((2-((4Z,7Z,10Z,13Z,16Z,19Z)-docosa-4,7, 10,13,16,19-hexaenamido)ethyl)disulfanyl)-3-methyl-2-(nicotinamidomethyl)butyl)carbamate (IV-14),

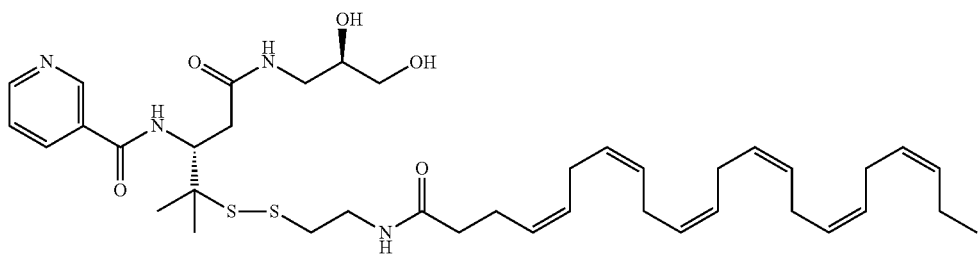 [SMILES: CC/C=C\C/C=C\C/C=C\C/C=C\C/C=C\C/C=C\CCC(=O)NCCSSC(C)(C)[C@@H](CC(=O)NC[C@@H](O)CO)NC(=O)c1cccnc1]

N—((R)-1-(((R)-2,3-dihydroxypropyl)amino)-4-((2-((4Z,7Z,10Z,13 Z,16Z,19Z)-docosa-4,7,10,13,16,19-hexaenamido)ethyl)disulfanyl)-4-methyl-1-oxopentan-3-yl)nicotinamide (IV-15),

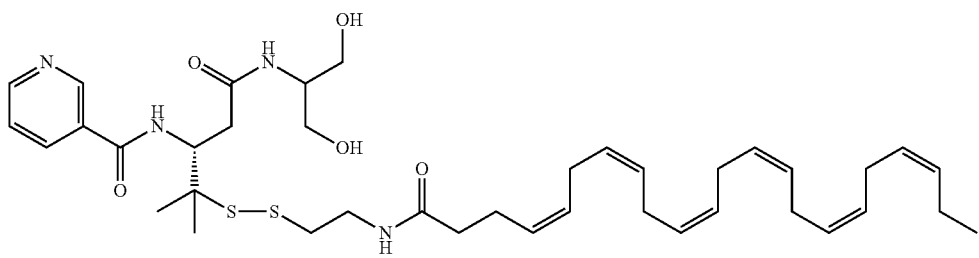 [SMILES: CC/C=C\C/C=C\C/C=C\C/C=C\C/C=C\C/C=C\CCC(=O)NCCSSC(C)(C)[C@@H](CC(=O)NC(CO)CO)NC(=O)c1cccnc1]

N—((R)-1-((1,3-dihydroxypropan-2-yl)amino)-4-((2-((4Z,7Z,10Z,13Z,16Z,19Z)-docosa-4,7,10,13,16,19-hexaenamido)ethyl)disulfanyl)-4-methyl-1-oxopentan-3-yl)nicotinamide (IV-16),

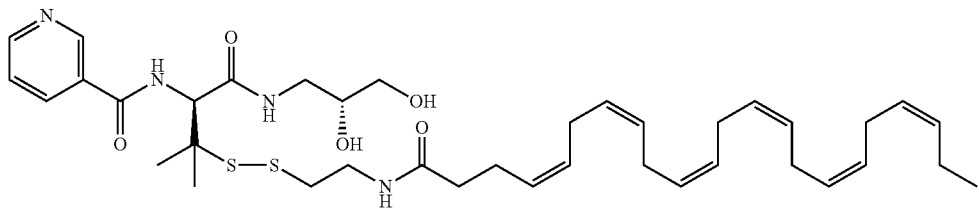 [SMILES: CC/C=C\C/C=C\C/C=C\C/C=C\C/C=C\C/C=C\CCC(=O)NCCSSC(C)(C)[C@@H](NC(=O)c1cccnc1)C(=O)NC[C@@H](O)CO]

N—((S)-1-(((R)-2,3-dihydroxypropyl)amino)-3-((2-((4Z,7Z,10Z,13Z,16Z,19Z)-docosa-4,7,10,13,16,19-hexaenamido)ethyl)disulfanyl)-3-methyl-1-oxobutan-2-yl)nicotinamide (IV-17),

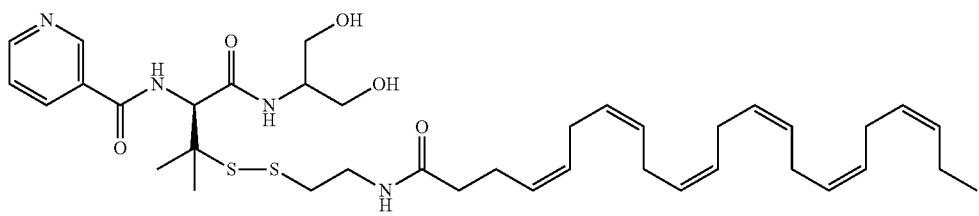 [SMILES: CC/C=C\C/C=C\C/C=C\C/C=C\C/C=C\C/C=C\CCC(=O)NCCSSC(C)(C)[C@@H](NC(=O)c1cccnc1)C(=O)NC(CO)CO]

N—((S)-1-((1,3-dihydroxypropan-2-yl)amino)-3-((2-((4Z,7Z,10Z,13Z,16Z,19Z)-docosa-4,7,10,13,16,19-hexaenamido)ethyl)disulfanyl)-3-methyl-1-oxobutan-2-yl)nicotinamide (IV-18),

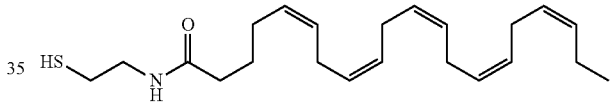

(4Z,7Z,10Z,13Z,16Z,19Z)—N-(2-mercaptoethyl)docosa-4,7,10,13,16,19-hexaenamide (I-1), and (5Z,8Z,11Z,14Z,17Z)—N-(2-mercaptoethyl)icosa-5,8,11,14,17-pentaenamide (I-2).

In certain embodiments, the compound is the following or a pharmaceutically acceptable salt thereof:

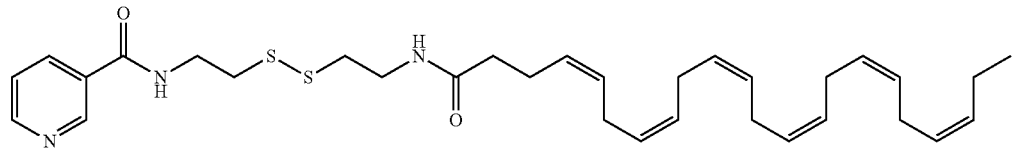 [SMILES: CC/C=C\C/C=C\C/C=C\C/C=C\C/C=C\C/C=C\CCC(=O)NCCSSCCNC(=O)c1cccnc1]

N-(2-((2-((4Z,7Z,10Z,13Z,16Z,19Z)-docosa-4,7,10,13,16,19-hexaenamido)ethyl)disulfanyl)ethyl)nicotinamide (II-1).

In certain embodiments, the compound is the following or a pharmaceutically acceptable salt thereof:

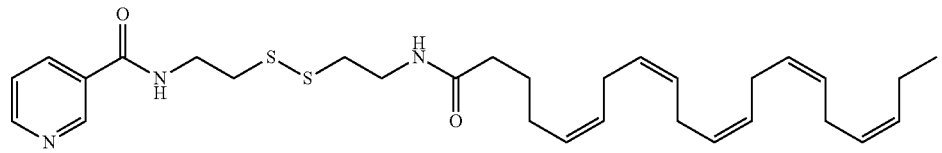 [SMILES: CC/C=C\C/C=C\C/C=C\C/C=C\C/C=C\CCCC(=O)NCCSSCCNC(=O)c1cccnc1]

N-(2-((2-((5Z,8Z,11Z,14Z,17Z)-icosa-5,8,11,14,17-pentaenamido)ethyl)disulfanyl)ethyl)nicotinamide (II-2).

In certain embodiments, the compound is the following or a pharmaceutically acceptable salt thereof:

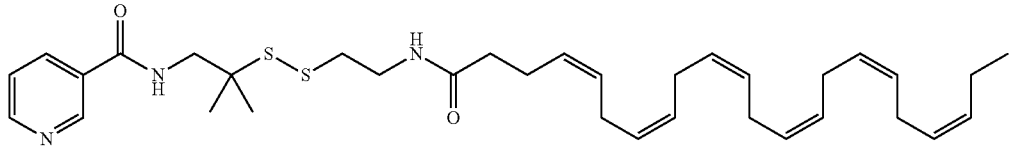 [SMILES: CC/C=C\C/C=C\C/C=C\C/C=C\C/C=C\C/C=C\CCC(=O)NCCSSC(C)(C)CNC(=O)c1cccnc1]

N-(2-((2-((4Z,7Z,10Z,13Z,16Z,19Z)-docosa-4,7,10,13,16,19-hexaenamido)ethyl)disulfanyl)-2-methylpropyl)nicotinamide (II-3).

In certain embodiments, the compound is the following or a pharmaceutically acceptable salt thereof:

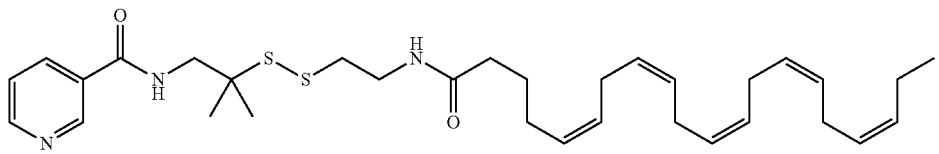 [SMILES: CC/C=C\C/C=C\C/C=C\C/C=C\C/C=C\CCCC(=O)NCCSSC(C)(C)CNC(=O)c1cccnc1]

N-(2-((2-((5Z,8Z,11Z,14Z,17Z)-icosa-5,8,11,14,17-pentaenamido)ethyl)disulfanyl)-2-methylpropyl)nicotinamide (II-4).

In certain embodiments, the compound is the following or a pharmaceutically acceptable salt thereof:

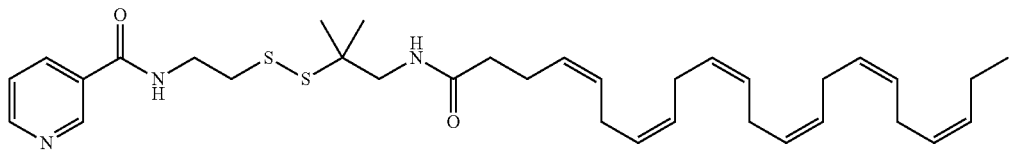 [SMILES: CC/C=C\C/C=C\C/C=C\C/C=C\C/C=C\C/C=C\CCC(=O)NCC(C)(C)SSCCNC(=O)c1cccnc1]

N-(2-((1-((4Z,7Z,10Z,13Z,16Z,19Z)-docosa-4,7,10,13,16,19-hexaenamido)-2-methylpropan-2-yl)disulfanyl)ethyl)nicotinamide (II-5).

In certain embodiments, the compound is the following or a pharmaceutically acceptable salt thereof:

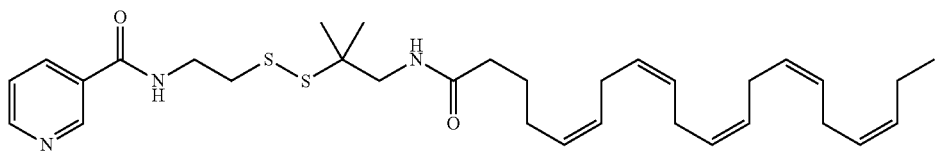 [SMILES: CC/C=C\C/C=C\C/C=C\C/C=C\C/C=C\CCCC(=O)NCC(C)(C)SSCCNC(=O)c1cccnc1]

N-(2-((1-((5Z,8Z,11Z,14Z,17Z)-icosa-5,8,11,14,17-pentaenamido)-2-methylpropan-2-yl)disulfanyl)ethyl)nicotinamide (II-6).

In certain embodiments, the compound is:

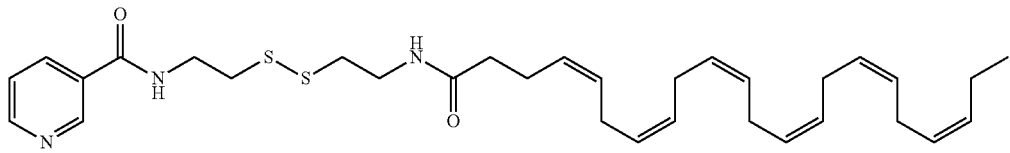 [SMILES: CC/C=C\C/C=C\C/C=C\C/C=C\C/C=C\C/C=C\CCC(=O)NCCSSCCNC(=O)c1cccnc1]

N-(2-((2-((4Z,7Z,10Z,13Z,16Z,19Z)-docosa-4,7,10,13,16,19-hexaenamido)ethyl)disulfanyl)ethyl)nicotinamide (II-1).

In certain embodiments, the compound is:

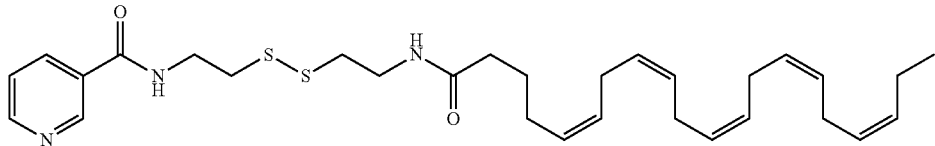 [SMILES: CC/C=C\C/C=C\C/C=C\C/C=C\C/C=C\CCCC(=O)NCCSSCCNC(=O)c1cccnc1]

N-(2-((2-((5Z,8Z,11Z,14Z,17Z)-icosa-5,8,11,14,17-pentaenamido)ethyl)disulfanyl)ethyl)nicotinamide (II-2).

In certain embodiments, the compound is:

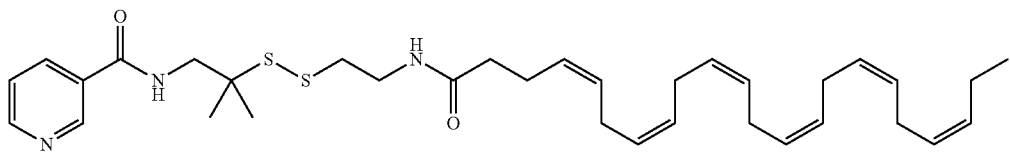 [SMILES: CC/C=C\C/C=C\C/C=C\C/C=C\C/C=C\C/C=C\CCC(=O)NCCSSC(C)(C)CNC(=O)c1cccnc1]

N-(2-((2-((4Z,7Z,10Z,13Z,16Z,19Z)-docosa-4,7,10,13,16,19-hexaenamido)ethyl)disulfanyl)-2-methylpropyl)nicotinamide (II-3).

In certain embodiments, the compound is:

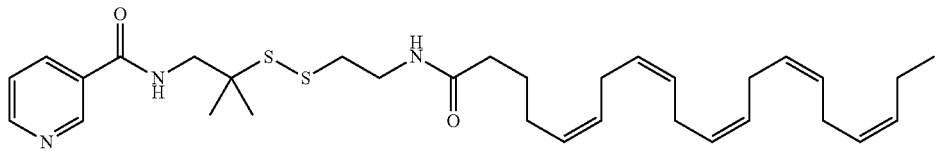 [SMILES: CC/C=C\C/C=C\C/C=C\C/C=C\C/C=C\CCCC(=O)NCCSSC(C)(C)CNC(=O)c1cccnc1]

N-(2-((2-((5Z,8Z,11Z,14Z,17Z)-icosa-5,8,11,14,17-pentaenamido)ethyl)disulfanyl)-2-methylpropyl)nicotinamide (II-4).

In certain embodiments, the compound is:

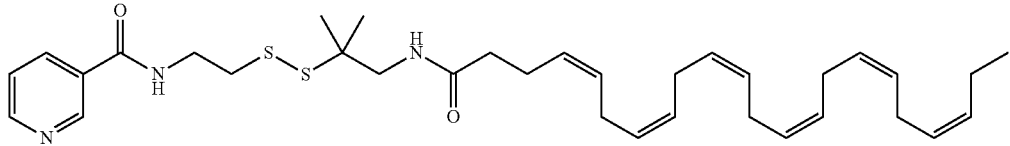 [SMILES: CC/C=C\C/C=C\C/C=C\C/C=C\C/C=C\C/C=C\CCC(=O)NCC(C)(C)SSCCNC(=O)c1cccnc1]

N-(2-((1-((4Z,7Z,10Z,13Z,16Z,19Z)-docosa-4,7,10,13,16,19-hexaenamido)-2-methylpropan-2-yl)disulfanyl)ethyl)nicotinamide (II-5).

In certain embodiments, the compound is:

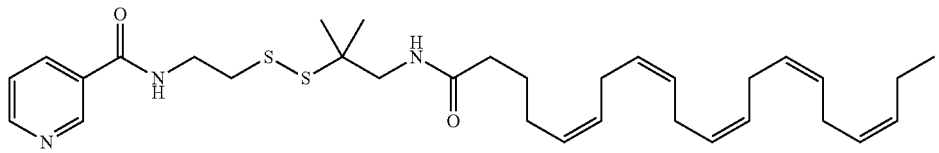 [SMILES: CC/C=C\C/C=C\C/C=C\C/C=C\C/C=C\CCCC(=O)NCC(C)(C)SSCCNC(=O)c1cccnc1]

N-(2-((1-((5Z,8Z,11Z,14Z,17Z)-icosa-5,8,11,14,17-pentaenamido)-2-methylpropan-2-yl)disulfanyl)ethyl)nicotinamide (II-6).

As indicated above, the invention provides a pharmaceutical composition comprising a compound described herein and a pharmaceutically acceptable carrier.

In its understood, that the fatty acid cysteamine conjugates of the invention may be synthesized by general procedures such as those described in the Examples.

III. Therapeutic Applications of Fatty Acid Cysteamine Conjugates

As indicated above, the invention is based in part on the discovery that fatty acid cysteamine conjugates are useful in activating autophagy. The fatty acid cysteamine conjugates of the invention have therapeutic effects that cannot be achieved by administering cysteamine or fatty acids separately or in combination, and offer a superior way of activating autophagy to treat or prevent CF in a way that cannot be replicated by administering the individual components or a combination of the individual components. The covalent linkage of cysteamine and an omega-3 fatty acid allows the simultaneous delivery of both components to a location, whereupon the individual components are released by cleavage, for example, enzymatic cleavage, at the location and at the same time. Exemplary therapeutic methods and additional features of the therapeutic applications are described below.

Exemplary Therapeutic Methods

One aspect of the invention provides a method of treating a disease described herein (e.g., a disease selected from the group consisting of CF, a neurodegenerative disease, inflammatory disease, a liver disease, muscle disease, infection, and an immune disease). The method comprises administering to a subject in need thereof a therapeutically effective amount of a fatty acid cysteamine conjugate described herein, such as a compound of Formula I, IA, IB, II, III, III-A, or IV to treat the disease.

In certain embodiments, the disease is CF. In certain embodiments, the disease is a neurodegenerative disease (e.g., Huntington's disease, Alzheimer's disease, or Parkinson's disease). In certain embodiments, the disease is an inflammatory disease. In certain embodiments, the disease a neurodegenerative disease, liver disease, muscle disease, infection, immunity, or inflammatory disease. Neurodegenerative diseases include Huntington's disease, Parkinson's disease, Alzheimer's disease, and transmissible spongiform encephalopathies. In certain embodiments, the disease is idiopathic pulmonary fibrosis. In certain embodiments, the disease is age-related macular degeneration. In yet other embodiments, the disease is a cardiac disease.

In certain embodiments, in the method of treating the disease, the administration of the compound of Formula I increases autophagy in a subject by at least 5%, 10%, 25%, 50%, or 100%. In certain embodiments, in the method of treating the disease, the administration of the compound of Formula I-A increases autophagy in a subject by at least 5%, 10%, 25%, 50%, or 100%. In certain embodiments, in the method of treating the disease, the administration of the compound of Formula I-B increases autophagy in a subject by at least 5%, 10%, 25%, 50%, or 100%. In certain embodiments, in the method of treating the disease, the administration of the compound of Formula III increases autophagy in a subject by at least 5%, 10%, 25%, 50%, or 100%. In certain embodiments, in the method of treating the disease, the administration of the compound of Formula III-A increases autophagy in a subject by at least 5%, 10%, 25%, 50%, or 100%. In certain embodiments, in the method of treating the disease, the administration of the compound of Formula IV increases autophagy in a subject by at least 5%, 10%, 25%, 50%, or 100%.

Additional diseases contemplated for treatment using methods described herein include, for example, the following diseases that are understood to have defective autophagy, including, without limitation, Danon disease, X-linked myopathy, infantile autophagic vacuolar myopathy, adult onset vacuolar myopathy, Pompe disease, sporadic inclusion body myositis, limb girdle muscular dystrophy type 2B, and Miyoshi myopathy.

The fatty acid cysteamine conjugates described herein may also useful for the treatment of mitochondrial diseases, including, without limitation, Leigh Syndrome, Diabetes Mellitus and Deafness (DAD), Leber's hereditary optic neuropathy, Neuropathy-ataxia-retinis pigmentosa and ptosis (NARP), myoneurogenic gastrointestinal encephalopathy (MNGIE), myoclonic epilepsy with ragged red fibers (MERRF), and mitochondrial myopathy-encephalomyopathy-lactic acidosis-stroke like symptoms (MELAS), Kearn-Sayre syndrome, subacute necrotizing encephalopathy (Leigh's Syndrome), and mitochondrial cardiomyopathies and other syndromes due to multiple mitochondrial DNA deletions. Additional mitochondrial diseases include, without limitation, neurogenic muscle weakness, progressive external opthalmoplegia (PEO), and Complex I disease, Complex II disease, Complex III disease, Complex IV disease and Complex V disease, which relates to dysfunction of the OXPHOS complexes, and MEGDEL syndrome (3-methylglutaconic aciduria type IV with sensorineural deafness, encephalopathy and Leigh-like syndrome.

In certain embodiments, the patient is a human.

Another aspect of the invention provides a method of activating autophagy in a subject. The method comprises administering to a subject in need thereof an effective amount of a fatty acid cysteamine conjugate described herein, such as a compound of Formula I-A, Formula III, Formula III-A, or Formula IV to activate autophagy in the subject. In certain embodiments, the subject suffers from CF, a neurodegenerative disease, or an inflammatory disease. In certain embodiments, the subject is a human.

In certain embodiments, in the method of treating the disease, the administration of a compound for example, Formula IA increases autophagy in a subject by at least 5%, 10%, 25%, 50% or at least 100%. In certain embodiments, in the method of treating the disease, the administration of a compound for example, Formula III increases autophagy in a subject by at least 5%, 10%, 25%, 50% or at least 100%. In certain embodiments, in the method of treating the disease, the administration of a compound for example, Formula III-A increases autophagy in a subject by at least 5%, 10%, 25%, 50% or at least 100%. In certain embodiments, in the method of treating the disease, the administration of a compound for example, Formula IV increases autophagy in a subject by at least 5%, 10%, 25%, 50% or at least 100%.

In certain embodiments, activation of autophagy can be characterized according to changes in the amount of certain biomarkers. One exemplary biomarker is microtubule-associated protein 1A/1B-light chain 3 (LC3), which is a soluble protein with a molecular mass of approximately 17 kDa that occurs throughout many mammalian tissues and cultured cells. In cells, a cytosolic form of LC3 (LC3-I) becomes conjugated to phosphatidylethanolamine to form LC3-phosphatidylethanolamine conjugate (LC3-II). See, for example, Tanida et al. (2008) METHODS MOL. BIOL., vol 445, p. 77-88. The amount of LC3-II relative to LC3-I can be used to analyze changes in the amount of autophagy. Accordingly, in certain embodiments, the administration of one or more of the foregoing compounds increases the ratio of LC3-II to LC3-I in the subject, such as at least about 10%, 25%, 50%, 75%, or 100% increase the ratio of LC3-II to LC3-I in the subject.

Another exemplary biomarker is p62 protein, also called sequestosome 1 (SQSTM1), which is a ubiquitin-binding scaffold protein that has been reported to colocalize with ubiquitinated protein aggregates. See, for example, Bjorkoy et al. (2009) METHODS ENZYMOL., vol. 452, p. 181-197. Accordingly, in certain embodiments, the administration of one or more of the foregoing compounds decreases the amount of p62 protein in the subject, such as by at least about 1%, 5%, 10%, 15%, 25%, 50%, 75%, or 90% w/w reduction in the amount of p62 protein in the subject.

In certain embodiments, in the method for increasing autophagy, the subject has been diagnosed as having CF. In certain embodiments, in the method for increasing autophagy, the subject has been diagnosed as having a neurodegenerative disease.

Further, and more generally, another aspect of the invention provides a method of increasing autophagy, wherein the method comprises administering to a subject in need thereof an effective amount of a molecular conjugate comprising a cysteamine covalently linked via a linker to a fatty acid, wherein the fatty acid is selected from the group consisting of omega-3 fatty acids and fatty acids that are metabolized in vivo to omega-3 fatty acids.

In addition, the invention provides a method of treating a disease selected from the group consisting of idiopathic pulmonary fibrosis, mitochondrial diseases, Leigh Syndrome, Diabetes Mellitus and Deafness (DAD), Leber's hereditary optic neuropathy, Neuropathy-ataxia-retinis pigmentosa and ptosis (NARP), myoneurogenic gastrointestinal encephalopathy (MNGIE), myoclonic epilepsy with ragged red fibers (MERRF), and mitochondrial myopathy-encephalomyopathy-lactic acidosis-stroke like symptoms (MELAS) in a patient. The method comprising administering to a patient in need thereof a therapeutically effective amount of:
(i) a compound of

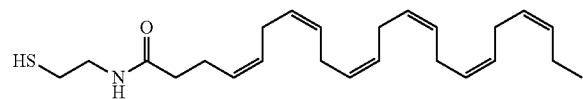 [SMILES: CC/C=C\C/C=C\C/C=C\C/C=C\C/C=C\C/C=C\CCC(=O)NCCS]

(4Z,7Z,10Z,13Z,16Z,19Z)—N-(2-mercaptoethyl)docosa-4,7,10,13,16,19-hexaenamide (I-1);
(ii) a compound of

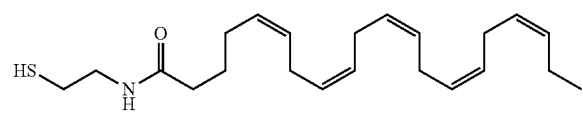 [SMILES: CC/C=C\C/C=C\C/C=C\C/C=C\C/C=C\CCCC(=O)NCCS]

(5Z,8Z,11Z,14Z,17Z)—N-(2-mercaptoethyl)icosa-5,8,11,14,17-pentaenamide (I-2); or
(iii) a combination of compound (i) or (ii), thereby to treat the disease. In one embodiment, the disease is idiopathic pulmonary fibrosis.

Additional Features of Autophagy, Cysteamine, and Conjugates

Autophagy is an evolutionarily conserved lysosomal degradation pathway to essentially self-digest some of the cellular components (see, Levine and Kroemer (2008) CELL, 132, p. 27-42). This self-digestion process serves as a means to help cells remove extraneous or damaged organelles, defective or mis-folded proteins and even invading microorganisms. It is known that autophagy is down-regulated in CF patients (Luciani et al. (2011) AUTOPHAGY, 7, p. 104-106). Autophagy also represents an important cellular mechanism for removing pathogens such as *Pseudomonas aegurinosa* from infected tissues such as lungs. Activation of autophagy can potentially help CF patients clear out *Pseudomonas aegurinosa* from their chronically infected lungs (Junkins et al. (2013) PLOS ONE, 8, e72263).

In CF, the defective CFTR causes an up-regulation of reactive oxygen species, which increases the activity of tissue transglutaminase (TG2), an enzyme that facilitates the cross linking between proteins. The increased TG2 activity induces the cross-linking of Beclin-1, a key protein in regulating autophagy. The cross-linking process of Beclin-1 displaces it from the endoplasmic reticulum, down-regulates autophagy and consequently causes an accumulation of p62 (also referred to SQSTM1). The increased p62 can sequester the mis-folded CFTR into aggresomes, which are then targeted for degradation by proteasomes. It has been observed that when human epithelial cells from CF patients with homozygous ΔF508 mutation were treated with a high concentration of cystamine (250 μM), there was an up-regulation of autophagy and a restoration of the CFTR to the plasma membrane (Luciani et al. (2012) AUTOPHAGY, 8, p. 1657-1672; Luciani et al. (2010) NAT. CELL BIOL., 12, p. 863-875). The rationale was that cystamine can inhibit TG2 activity, which decreases the cross-linking of BECN1. This process causes a reduction in the level of p62, which then allows the mis-folded CFTR to escape sequestration into the aggresomes and to localize in the Golgi for transport to the membrane. Though promising, this method of restoring activity to the defective CFTR has one major drawback, namely the high concentration of cystamine that is needed to induce autophagy in various epithelial cell lines (250 μM). It is contemplated that this high concentration of cystamine would require a human dose that may be impractical as well as potentially non-compliant to the patients since it is known that cystamine/cysteamine can induce a significant level of GI discomfort at high doses (Kan et al. (1984) BRIT. J. EXP. PATHOLOGY, 65, p. 759-765).

The fatty acid cysteamine conjugates have been designed to bring together cysteamine analogs and omega-3 fatty acids into a single molecular conjugate. The activity of the fatty acid cysteamine conjugates is substantially greater than the sum of the individual components of the molecular conjugate, suggesting that the activity induced by the fatty acid cystamine conjugates is synergistic. Another benefit of the fatty acid cysteamine conjugates of the invention is that they demonstrate very low or no peripheral toxicity.

IV. Pharmaceutical Compositions

The invention provides pharmaceutical compositions comprising a fatty acid cysteamine conjugate, such as a compound of Formula I, I-A, I-B, II, III, III-A, or IV. In certain embodiments, the pharmaceutical compositions preferably comprise a therapeutically-effective amount of one or more of the fatty acid cysteamine conjugates described above, formulated together with one or more pharmaceutically acceptable carriers. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets (e.g., those targeted for buccal, sublingual, and/or systemic absorption), boluses, powders, granules, pastes for application to the tongue; (2) parenteral administration by, for example, subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Administration of the fatty acid cysteamine conjugates can be accomplished via any suitable mode of administration for therapeutic agents. These modes include systemic or local administration such as oral, nasal, parenteral, transdermal, subcutaneous, vaginal, buccal, rectal or topical administration modes.

Depending on the intended mode of administration, the compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, all using forms well known to those skilled in the pharmaceutical arts.

Illustrative pharmaceutical compositions are tablets and gelatin capsules comprising a fatty acid cysteamine conjugate and a pharmaceutically acceptable carrier, such as: a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, alginic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropylcyclodextrin, PEG400, PEG200.

Liquid, particularly injectable, compositions can, for example, be prepared by dissolution, dispersion, etc. For example, the fatty acid cysteamine conjugate is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the fatty acid cysteamine conjugates.

The fatty acid cysteamine conjugates can be also formulated as a suppository that can be prepared from fatty emulsions or suspensions; using polyalkylene glycols such as propylene glycol, as the carrier.

The fatty acid cysteamine conjugates can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564.

Parenteral injectable administration is generally used for subcutaneous, intramuscular or intravenous injections and infusions. Injectables can be prepared in conventional forms, either as liquid solutions or suspensions or solid forms suitable for dissolving in liquid prior to injection.

Compositions can be prepared according to conventional mixing, granulating or coating methods, respectively, and the present pharmaceutical compositions can contain from about 0.1% to about 80%, from about 5% to about 60%, or from about 1% to about 20% of the fatty acid cysteamine conjugate by weight or volume.

The dosage regimen utilizing the fatty acid cysteamine conjugate is selected in accordance with a variety of factors including type, species, age, weight, sex and medical condition of the patient; the severity of the condition to be treated; the route of administration; the renal or hepatic function of the patient; and the particular fatty acid cysteamine conjugate employed. A physician or veterinarian of ordinary skill in the art can readily determine and prescribe the effective amount of the drug required to prevent, counter or arrest the progress of the condition.

Effective dosage amounts of the present invention, when used for the indicated effects, range from about 20 mg to about 5,000 mg of the fatty acid cysteamine conjugate per day. Compositions for in vivo or in vitro use can contain about 20, 50, 75, 100, 150, 250, 500, 750, 1,000, 1,250, 2,500, 3,500, or 5,000 mg of the fatty acid cysteamine conjugate. Effective plasma levels of the fatty acid cysteamine conjugate can range from about 5 ng/mL to 5000 ng/mL per day. Appropriate dosages of the fatty acid cysteamine conjugates can be determined as set forth in Goodman, L. S.; Gilman, A. (1975) THE PHARMACOLOGICAL BASIS OF THERAPEUTICS, 5th ed.; MacMillan: New York, pp. 201-226. Fatty acid cysteamine conjugates can be administered in a single daily dose, or the total daily dosage can be administered in divided doses of two, three or four times daily.

Combination Therapies

Fatty acid cysteamine conjugates may also be administered with other therapeutic agents such as CFTR modulators, epithelial sodium channel (ENaC) inhibitors, anti-inflammatory agents, anti-fibrotic agents and antibacterial agents. In some embodiments, the other therapeutic agent is a CFTR modulator. Non-limiting examples of a CFTR modulator include Ivacaftor (VX-770), Lumacaftor (VX-809), VX-661, Orkambi (the combination of VX-770 and VX-809), VX-152, VX-440, the combination of VX-661 and VX-770, the combination of VX-152/VX-809 and VX-770, the combination of VX-440/VX-809 and VX-770, P-1037, Riociguat, N91115, QBW251, QR-010, GLPG1837, GLPG2222, GLP2665, genistein, baicalein, epigallocatechin gallate (EGCG), trimethylangelicin and Ataluren.

In some embodiments, the other therapeutic agent is an anti-inflammatory agent. Non-limiting examples of an anti-inflammatory agent include ibuprofen, prednisolone, dexamethasone, hydrocortisone, methylprednisolone, beclometasone, budesonide, fluticasone, mometasone, Seretide (fluticasone plus salmeterol), Symbicort (budesonide plus formoterol) and N91115.

In some embodiments, the other therapeutic agent is an anti-bacterial agent. Non-limiting examples of an anti-bacterial agent include azithromycin, tobramycin, aztreonam lysine, colistin, aminoglycosides, vancomycin, ciprofloxacin, levofloxacin, and sulfonamides.

In some embodiments, the other therapeutic agent is an epithelial sodium channel (ENaC) inhibitor. Non-limiting examples of ENaC inhibitors include amiloride, BA-39-9437, GS-9411 and P-1037.

In some embodiments, the other therapeutic agent is an anti-fibrotic agent. Non-limiting examples of anti-fibrotic agents include pirfenidone, nintedanib, INT-767, STX-100, AM152, pentoxyphilline, FG-3019, CNTO 888, Tralokinumab, SAR156597, GS-6624, BMS-986020, Lebrikizumab, GSK2126458, ACT-064992, vismodegib, PRM-151, IW001 and Fresolimumab.

V. Kits for Use in Medical Applications

Another aspect of the invention provides a kit for treating a disorder. The kit comprises: i) instructions for treating a medical disorder, such as CF; and ii) a fatty acid cysteamine conjugate described herein. The kit may comprise one or more unit dosage forms containing an amount of a fatty acid cysteamine conjugate described herein.

The description above describes multiple aspects and embodiments of the invention, including fatty acid cysteamine conjugate, compositions comprising a fatty acid cysteamine conjugate, methods of using the fatty acid cysteamine conjugate, and kits. The patent application specifically contemplates all combinations and permutations of the aspects and embodiments.

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby.

Example 1

Preparation of N-(2-((2-((5Z,8Z,11Z,14Z,17Z)-icosa-5,8,11,14,17-pentaenamido)ethyl) disulfanyl) ethyl)nicotinamide (II-2)

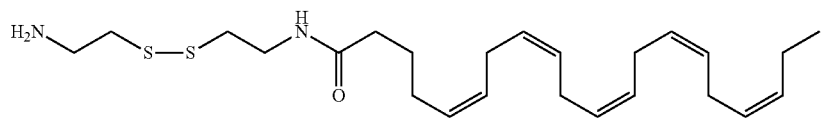

-continued

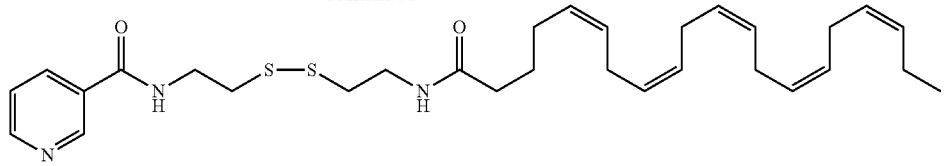

In a typical run, (5Z,8Z,11Z,14Z,17Z)—N-(2-((2-amino-ethyl)disulfanyl)ethyl)icosa-5,8,11,14,17-pentaenamide (1 mmol, prepared according to the procedures outlined in WO2012/115695) was taken up in 25 mL of $CH_2Cl_2$ along with nicotinic acid (1 mmol), HATU (1.1 mmol) and $Et_3N$ (1.5 mmol). The resulting reaction mixture was stirred at room temperature for 8 hours and diluted with saturated aqueous $NH_4Cl$. The two layers were separated and the organic layer was washed with brine, dried ($Na_2SO_4$) and concentrated under reduced pressure. The resulting residue was purified by silica gel chromatography (95% $CH_2Cl_2$, 5% MeOH) to afford N-(2-((245Z,8Z,11Z,14Z,17Z)-icosa-5,8,11,14,17-pentaenamido)ethyl)disulfanyl) ethyl)nicotinamide. MS (EI) calcd for $C_{30}H_{43}N_3O_2S_2$ 541.28; found 542 $[M+H]^+$.

Example 2

Preparation of N-(2-((2-((4Z,7Z,10Z,13Z,16Z,19Z)-docosa-4,7,10,13,16,19-hexaenamido)ethyl)disulfanyl)-2-methylpropyl)nicotinamide (II-3)

inert atmosphere of nitrogen and then concentrated under reduced pressure. The resulting residue was purified by silica gel chromatography ($CH_2Cl_2$/MeOH=10/1) to afford 2-(pyridin-2-yldisulfanyl)ethan-1-amine (39 g, 92% yield). A mixture containing 2-(pyridin-2-yldisulfanyl)ethan-1-amine (5 g, 26.8 mmol), DHA (9.2 g, 26.8 mmol), and HATU (10.2 g, 26.8 mmol) were taken up in $CH_2Cl_2$ (100 mL) and stirred at room temperature. Triethylamine (18 mL, 40.3 mmol) was then added dropwise at room temperature. The resulting reaction mixture was stirred at room temperature for 18 hours, which was then diluted with water and extracted with $CH_2Cl_2$. The combined organic layers were washed with water (3×100 mL), brine (100 mL), dried over anhydrous $Na_2SO_4$, and concentrated under reduced pressure. The resulting residue was purified by silica gel chromatography (pentanes/EtOAc) to afford (4Z,7Z,10Z,13Z,16Z,19Z)—N-(2-(pyridin-2-yldisulfanyl)ethyl)docosa-4,7,10,13,16,19-hexaenamide (10 g, 75% yield) as a light brown oil.

1-Amino-2-methylpropane-2-thiol (1.14 g, 8 mmol) was added dropwise at room temperature to a solution containing

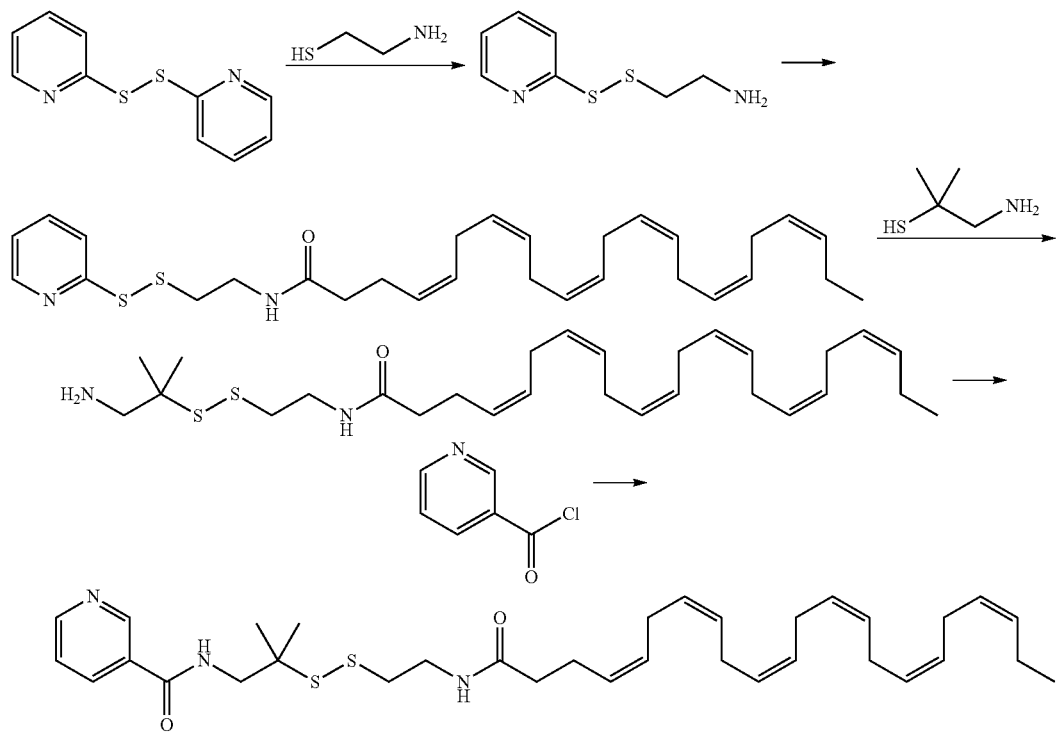

A solution containing 1,2-di(pyridin-2-yl)disulfane (26 g, 0.227 mmol) in MeOH (200 mL) was added dropwise at room temperature to a solution containing cysteamine (50 g, 0.227 mmol) in MeOH (200 mL). The resulting reaction mixture was stirred at room temperature for 2 hours under an (4Z,7Z,10Z,13Z,16Z,19Z)—N-(2-(pyridin-2-yldisulfanyl)ethyl)docosa-4,7,10,13,16,19-hexaenamide (4 g, 8 mmol) in a 1:1 mixture of MeOH/DMF (10 mL). The resulting reaction mixture was stirred at room temperature for 18 hours, which was then diluted with water and extracted with EtOAc. The combined organic layers were washed with water (2×50 mL), brine (50 mL), dried over $Na_2SO_4$, and concentrated under reduced pressure. The resulting residue was purified by silica gel chromatography (pentanes/EtOAc) to afford (4Z,7Z,10Z,13Z,16Z,19Z)—N-(2-((1-amino-2-methylpropan-2-yl)disulfanyl)ethyl)docosa-4,7,10,13,16,19-hexaenamide (3.2 g, 81% yield) as a light brown oil.

(4Z,7Z,10Z,13Z,16Z,19Z)—N-(2-((1-Amino-2-methyl-propan-2-yl)disulfanyl)ethyl)docosa-4,7,10,13,16,19-hexaenamide (3.2 g, 6.5 mmol) and nicotinoyl chloride (1.8 g, 13 mmol) were taken up in $CH_2Cl_2$ (30 mL). Triethylamine (3 mL, 19.5 mmol) was added dropwise at 0° C. The resulting mixture was stirred at room temperature for 18 hours, which was then diluted with water and extracted with $CH_2Cl_2$. The combined organic layers were washed with water (2×50 mL), brine (50 mL), dried over $Na_2SO_4$, and concentrated under reduced pressure. The resulting residue was purified by silica gel chromatography (pentanes/EtOAc) to afford N-(2-((2-((4Z,7Z,10Z,13Z,16Z,19Z)-docosa-4,7,10,13,16,19-hexaenamido)ethyl)disulfanyl)-2-methylpropyl)nicotinamide (2.2 g, 57% yield) as a light brown oil. MS calculated for $C_{34}H_{49}N_3O_2S_2$: 595.3; Found: 596.3 $[M+H]^+$.

Example 3

Preparation of N-(2-((2-((5Z,8Z,11Z,14Z,17Z)-icosa-5,8,11,14,17-pentaenamido)ethyl)disulfanyl)-2-methylpropyl)nicotinamide (II-4)

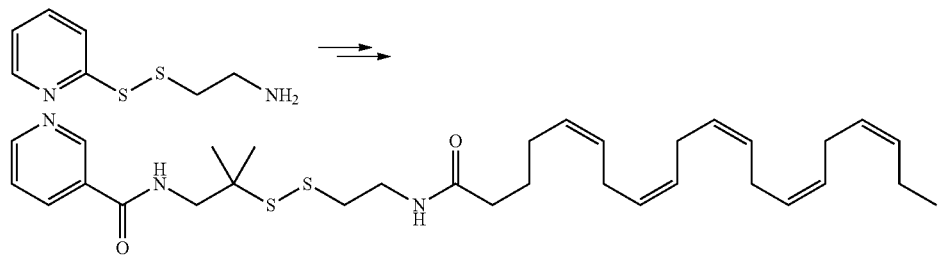

This compound was prepared using the procedures outlined in the preparation of N-(2-((2-((4Z,7Z,10Z,13Z,16Z,19Z)-docosa-4,7,10,13,16,19-hexaenamido)ethyl)disulfanyl)-2-methylpropyl)nicotinamide in Example 2, substituting DHA for EPA. MS calculated for $C_{32}H_{47}N_3O_2S_2$: 569.3; Found: 570 $[M+H]^+$.

Example 4

Preparation of N-(2-((1-((5Z,8Z,11Z,14Z,17Z)-icosa-5,8,11,14,17-pentaenamido)-2-methylpropan-2-yl)disulfanyl)ethyl)nicotinamide (II-6)

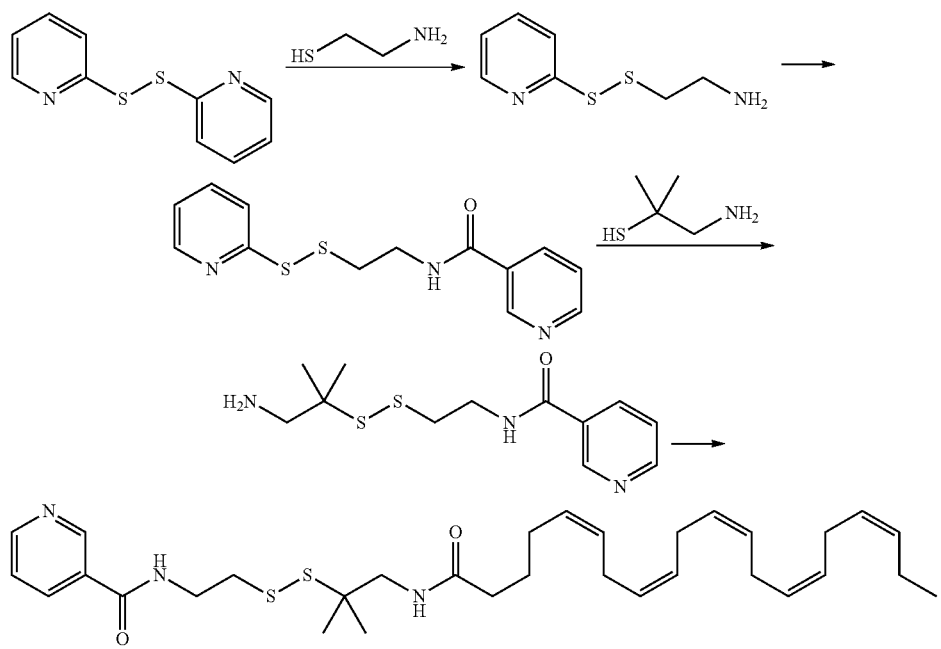

A mixture containing 2-(pyridin-2-yldisulfanyl)ethan-1-amine (8 g, 40 mmol, 1 eq) and nicotinic acid (5.3 g, 40 mmol) in DMF (100 mL) was stirred at room temperature. HATU (18.3 g, 48 mmol, 1.2 eq) and Et$_3$N (4.58 g, 48 mmol) were then added. The resulting reaction mixture was stirred at room temperature for 18 hours, which was then diluted with EtOAc and washed with water and brine. The organic layer was dried (Na$_2$SO$_4$) and concentrated under reduced pressure. The resulting residue was purified by silica gel chromatography (CH$_2$Cl$_2$/MeOH) to provide N-(2-(pyridin-2-yldisulfanyl)ethyl)nicotinamide (5.5 g, 45% yield) as a yellow oil. A mixture containing N-(2-(pyridin-2-yldisulfanyl)ethyl)nicotinamide (5.5 g, 0.019 mol) in NaOH/H$_2$O (1.5 g/15 mL) was stirred at room temperature until the material was dissolved. 1-Amino-2-methylpropane-2-thiol (2.1 g, 0.019 mol) was then added, followed by another portion of NaOH/H$_2$O (1.5 g/15 mL). The resulting reaction mixture was stirred at room temperature for 2 hours and then diluted with EtOAc. The organic layer was washed with water, brine, dried (Na$_2$SO$_4$) and concentrated under reduced pressure. The resulting crude solid was used directly in the next step without further purification. A mixture containing N-(2-((1-amino-2-methylpropan-2-yl)disulfanyl)ethyl)nicotinamide (2.5 g, 8.77 mmol) and EPA (2.65 g, 8.77 mmol) in DMF (40 mL) was stirred at room temperature. HATU (4 g, 10.5 mmol) and Et$_3$N (1.065 mg, 10.5 mmol) were then added. The resulting reaction mixture was stirred at room temperature for 18 hours and then diluted with EtOAc. The organic layer was washed with water, brine, dried (Na$_2$SO$_4$) and concentrated under reduced pressure. The resulting residue was purified by silica gel chromatography (MeOH/CH$_2$Cl$_2$=15/1) to afford N-(2-((1-((5Z,8Z,11Z,14Z,17Z)-icosa-5,8,11,14,17-pentaenamido)-2-methylpropan-2-yl)disulfanyl)ethyl)nicotinamide (1.6 g, 33% yield) as a yellow oil. MS calculated for C$_{32}$H$_{47}$N$_3$O$_2$S$_2$: 569.3; Found: 570.3 [M+H]$^+$.

Example 5

Preparation of N—((S)-1-(((R)-2,3-dihydroxypropyl)amino)-3-((2-((4Z,7Z,10Z,13Z,16Z,19Z)-docosa-4,7,10,13,16,19-hexaenamido)ethyl)disulfanyl)-3-methyl-1-oxobutan-2-yl)nicotinamide (IV-17)

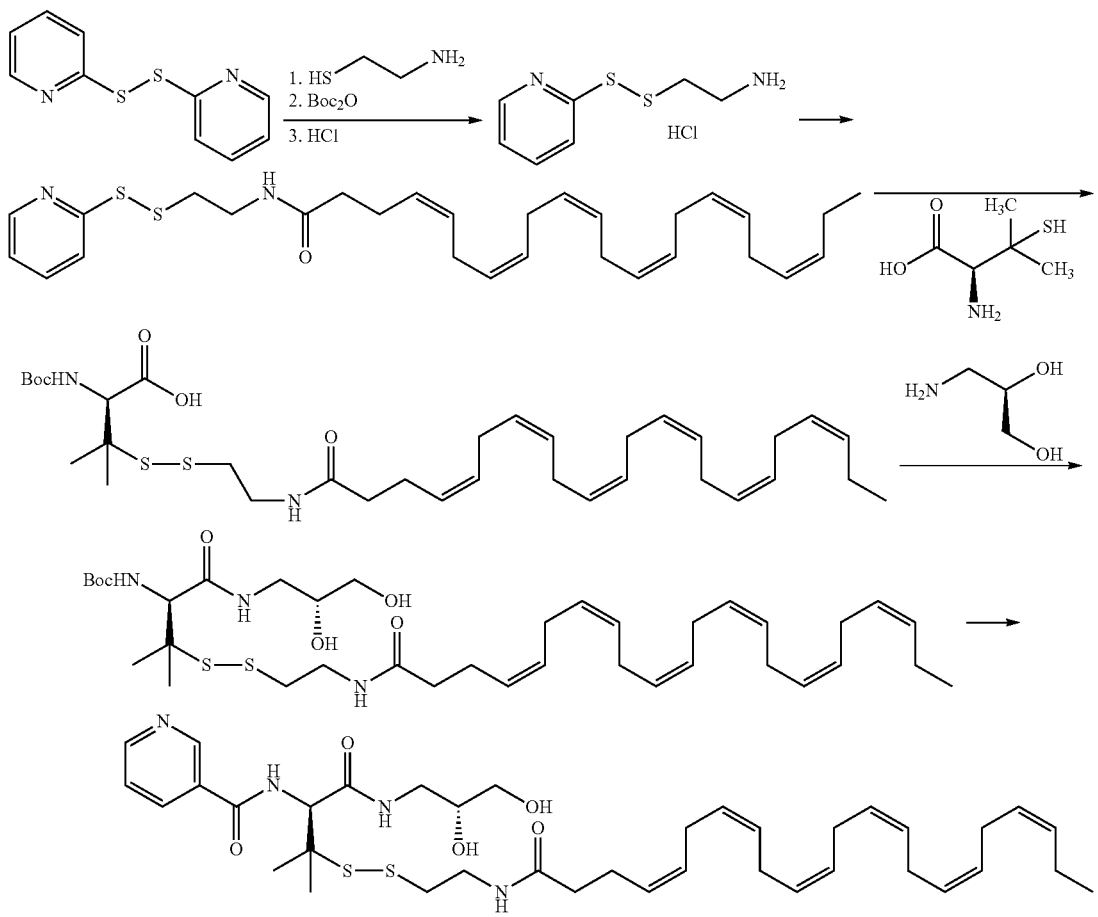

A solution containing cysteamine hydrochloride (7.87 g, 69.3 mmol) in methanol (100 mL) was added dropwise to a solution of 2,2'-dithiopyridine (25.0 g, 113.6 mmol) in methanol (300 mL). The resulting reaction mixture was stirred at room temperature for 18 hours. Di-tert-butyl dicarbonate (15.1 g, 69.3 mmol) and aqueous sodium hydroxide (5M, 30 mL) were added slowly. The reaction mixture was stirred at room temperature for an additional 4 hours. The mixture was then extracted with ethyl acetate (300 mL×2). The combined organic layers were washed with brine (300 mL), dried over Na$_2$SO$_4$ and concentrated under reduced pressure. The resulting residue was purified by silica gel chromatography (hexanes/ethyl acetate=10:1 to 5:1) to afford tert-butyl 2-(pyridin-2-yldisulfanyl)ethylcarbamate (8.3 g, 42.3% yield) as a yellow oil.

tert-Butyl 2-(pyridin-2-yldisulfanyl)ethylcarbamate (5.8 g, 25.6 mmol) was dissolved in 1,4-dioxane (30 mL) and the solution was cooled to 0° C. A solution of HCl in 1,4-dioxane (5M, 20 mL) was then added dropwise. The resulting reaction mixture was stirred for 2 hours and then concentrated under reduced pressure to afford 2-(pyridin-2-yldisulfanyl)ethanamine (5.6 g, 100% yield, HCl salt).

A mixture of 2-(pyridin-2-yldisulfanyl)ethanamine (12.0 g, 64.5 mmol), DHA (51.6 mmol) and HATU (29.3 g, 77 mmol) in DCM (150 mL) was cooled to 0° C. and Hunig's base (25 g, 190 mmol) was added. The resulting reaction mixture was allowed to warm to room temperature and stirred for 18 hours. Saturated aqueous NH$_4$Cl (200 mL) was added to quench the reaction and the resulting mixture was extracted with CH$_2$Cl$_2$ (300 mL×2). The combined organic layers were washed with brine, dried over Na$_2$SO$_4$ and concentrated under reduced pressure. The resulting residue was purified by silica gel chromatography (methanol/CH$_2$Cl$_2$=0.5% to 2.0%) to afford (4Z,7Z,10Z,13Z,16Z,19Z)—N-(2-(pyridin-2-yldisulfanyl)ethyl)docosa-4,7,10,13,16,19-hexaenamide as a yellow oil.

A mixture of (4Z,7Z,10Z,13Z,16Z,19Z)—N-(2-(pyridin-2-yldisulfanyl)ethyl)docosa-4,7,10,13,16,19-hexaenamide (4.8 g, 9.6 mmol) and (S)-2-amino-3-mercapto-3-methyl butanoic acid (1.44 g, 9.6 mol) in MeOH (100 mL) were stirred at room temperature for 18 hours. Di-tert-butyl dicarbonate (2.1 g, 9.6 mmol) was then added, followed by the slow addition of 3 M aqueous sodium hydroxide solution (30 mL). The resulting reaction mixture was stirred at room temperature for 4 hours and then extracted with EtOAc (100 mL×2). The combined organic layers were washed with brine, dried over Na$_2$SO$_4$ and concentrated under reduced pressure. The resulting residue was purified by silica gel chromatography (methanol/CH$_2$Cl$_2$=0% to 1.5%) to afford (R)-2-((tert-butoxycarbonyl)amino)-3-((2-((4Z,7Z,10Z,13Z,16Z,19Z)-docosa-4,7,10,13,16,19-hexaenamido)ethyl)disulfanyl)-3-methylbutanoic acid (5.4 g, 88.2% yield) as a yellow oil.

A mixture of (R)-3-aminopropane-1,2-diol (0.17 g, 1.9 mmol), (R)-2-((tert-butoxycarbonyl)amino)-3-((2-((4Z,7Z,10Z,13Z,16Z,19Z)-docosa-4,7,10,13,16,19-hexaenamido)ethyl)disulfanyl)-3-methylbutanoic acid (1.2 g, 1.9 mmol) and HATU (0.86 g, 2.2 mmol) in CH$_2$Cl$_2$ (20 mL) was cooled to 0° C. and Hunig's base (0.73 g, 5.6 mmol) was added. The reaction mixture was allowed to warm to room temperature and stirred for 18 hours. Saturated aqueous NH$_4$Cl (20 mL) was added and the resulting mixture was extracted with CH$_2$Cl$_2$ (50 mL×2). The combined organic layers were washed with brine, dried over Na$_2$SO$_4$ and concentrated under reduced pressure. The resulting residue was purified by silica gel chromatography (methanol/DCM=0.5% to 2.5%) to afford tert-butyl ((R)-1-(((R)-2,3-dihydroxypropyl)amino)-3-((2-((4Z,7Z,10Z,13 Z,16Z,19Z)-docosa-4,7,10,13,16,19-hexaenamido)ethyl)disulfanyl)-3-methyl-1-oxobutan-2-yl)carbamate (0.9 g, 67.7% yield) as a yellow oil.

A mixture containing tert-Butyl ((R)-1-(((R)-2,3-dihydroxypropyl)amino)-3-((2-((4Z,7Z,10Z,13Z,16Z,19Z)-docosa-4,7,10,13,16,19-hexaenamido)ethyl)disulfanyl)-3-methyl-1-oxobutan-2-yl)carbamate (1.05 g, 1.48 mmol) in 1,4-dioxane (5 mL) was cooled to 0° C. and a solution containing 5M HCl in 1,4-dioxane (8 mL) was added dropwise. The resulting reaction was stirred for 2 hours then concentrated under reduced pressure to afford the HCl salt of (4Z,7Z,10Z,13Z,16Z,19Z)—N-(2-(((R)-3-amino-4-(((R)-2,3-dihydroxypropyl)amino)-2-methyl-4-oxobutan-2-yl)disulfanyl)ethyl)docosa-4,7,10,13,16,19-hexaenamide.

A mixture of (4Z,7Z,10Z,13Z,16Z,19Z)—N-(2-(((R)-3-amino-4-(((R)-2,3-dihydroxypropyl)amino)-2-methyl-4-oxobutan-2-yl)disulfanyl)ethyl)docosa-4,7,10,13,16,19-hexaenamide (HCl salt, 0.95 g, 1.47 mmol), niacin (0.18 g, 1.5 mmol) and HATU (0.67 g, 1.76 mmol) in CH$_2$Cl$_2$ (20 mL) was cooled to 0° C. and Hunig's base (0.76 g, 5.9 mmol) was added. The reaction mixture was allowed to warm to room temperature and stirred for 18 hours. Saturated aqueous NH$_4$Cl (30 mL) was added and the resulting mixture was extracted with CH$_2$Cl$_2$ (80 mL×2). The combined organic layers were washed with brine, dried over Na$_2$SO$_4$ and concentrated under reduced pressure. The resulting residue was purified by silica gel chromatography (methanol/CH$_2$Cl$_2$=1.0% to 3.5%) to afford N—((S)-1-(((R)-2,3-dihydroxypropyl)amino)-3-((2-((4Z,7Z,10Z,13Z,16Z,19Z)-docosa-4,7,10,13,16,19-hexaenamido)ethyl)disulfanyl)-3-methyl-1-oxobutan-2-yl)nicotinamide (0.28 g, 26.9% yield) as a yellow solid. MS (EI) calcd for C$_{38}$H$_{56}$N$_4$O$_5$S$_2$ 712.37; found 713.15 [M+H]+.

Example 6

Preparation of N—((S)-1-((1,3-dihydroxypropan-2-yl)amino)-3-((2-((4Z,7Z,10Z,13Z,16Z,19Z)-docosa-4,7,10,13,16,19-hexaenamido)ethyl)disulfanyl)-3-methyl-1-oxobutan-2-yl)nicotinamide (IV-18)

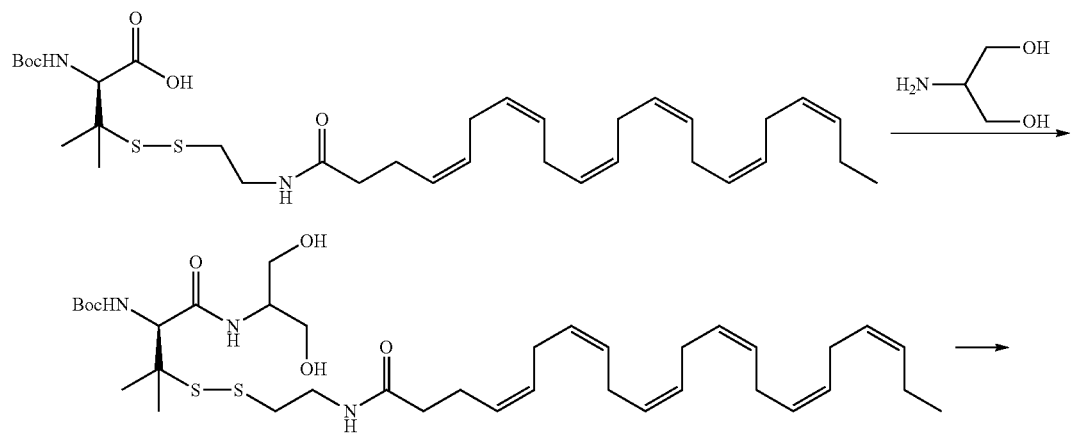

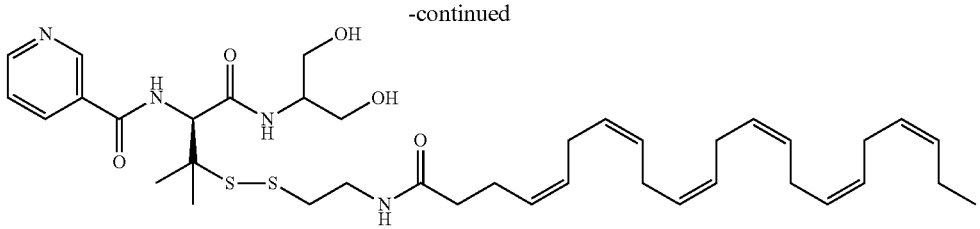

The same experimental procedure outlined in the preparation of compound IV-17 (Example 5) was used, except that (R)-3-aminopropane-1,2-diol was substituted with 2-aminopropane-1,3-diol. MS (EI) calcd for $C_{38}H_{56}N_4O_5S_2$ 712.37; found 713.15 [M+H]$^+$.

Example 7

Preparation of (R)-3-((2-((4Z,7Z,10Z,13Z,16Z, 19Z)-docosa-4,7,10,13,16,19-hexaenamido)ethyl) disulfanyl)-3-methyl-2-(nicotinamido)butyl (1,3-dihydroxypropan-2-yl)carbamate (IV-6)

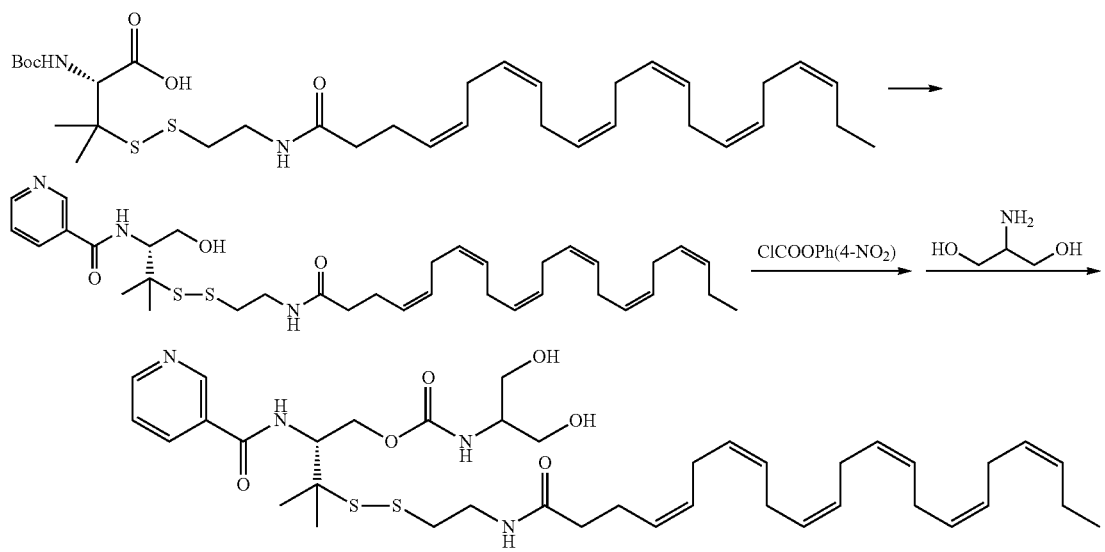

(R)-2-((tert-Butoxycarbonyl)amino)-34244Z,7Z,10Z, 13Z,16Z,19Z)-docosa-4,7,10,13,16,19-hexaenamido)ethyl) disulfanyl)-3-methylbutanoic acid was prepared according to the procedures outlined in Example 5 using (R)-2-amino-3-mercapto-3-methylbutanoic acid as the appropriate starting material. (R)-2-((tert-Butoxycarbonyl)amino)-3-((2-((4Z,7Z,10Z,13Z,16Z,19Z)-docosa-4,7,10,13,16,19-hexaenamido)ethyl)disulfanyl)-3-methylbutanoic acid (8.0 g, 12.6 mmol) was dissolved in THF (100 ml) and the solution was then cooled to −15° C. while N-methylmorpholine (1.3 g, 13 mmol) was added followed by isobutyl carbonochloridate (1.8 g, 13 mmol). The resulting reaction mixture was stirred for 30 min. It was then warmed to room temperature and filtered. The filtrate was cooled to −20° C., a suspension of sodium borohydride (0.96 g, 25 mmol) in water (2 mL) was added carefully. The resulting reaction mixture was stirred for 2 h and then quenched with water (200 mL). The resulting mixture was extracted with $CH_2Cl_2$ (200 mL×4). The combined organic layers were washed with brine, dried over $Na_2SO_4$ and concentrated under reduced pressure. The resulting residue was purified by silica gel chromatography (methanol/$CH_2Cl_2$=0.5% to 1.2%) to afford tert-butyl ((R)-3-((2-((4Z,7Z,10Z,13Z,16Z,19Z)-docosa-4,7,10,13,16,19-hexaenamido)ethyl)disulfanyl)-1-hydroxy-3-methylbutan-2-yl)carbamate (5.6 g, 71.8% yield) as a yellow oil. This material (5.6 g, 9.03 mmol) was dissolved in 1,4-dioxane (10 mL) and the solution was cooled to 0° C. while 5M HCl/1,4-dioxane (15 mL) was added dropwise. The resulting reaction mixture was stirred at room temperature for 30 minutes and then concentrated under reduced pressure to afford the HCl salt of (4Z,7Z,10Z,13Z,16Z,19Z)—N-(2-(((R)-3-amino-4-hydroxy-2-methylbutan-2-yl)disulfanyl) ethyl)docosa-4,7,10,13,16,19-hexaenamide.

The HCl salt of (4Z,7Z,10Z,13Z,16Z,19Z)—N-(2-(((R)-3-amino-4-hydroxy-2-methylbutan-2-yl)disulfanyl)ethyl) docosa-4,7,10,13,16,19-hexaenamide (1 mmol) is taken up on $CH_2Cl_2$ (10 mL) along with nicotinic acid (1 mmol), HATU (1.1 mmol) and Hunig's base (1.5 mmol). The resulting reaction mixture is stirred at room temperature for 4 hours and diluted with saturated aqueous $NH_4Cl$. The two layers are separated and the organic layer is washed with brine, dried ($Na_2SO_4$) and concentrated under reduced pressure. Purification by chromatography ($CH_2Cl_2$/MeOH 9:1) affords N—((R)-3-((2-((4Z,7Z,10Z,13Z,16Z,19Z)-docosa-4,7,10,13,16,19-hexaenamido)ethyl)disulfanyl)-1-hydroxy-3-methylbutan-2-yl)nicotinamide. This material (0.5 mmol) is taken up in THF (5 mL) and the solution is then cooled to 0° C. while pyridine (1.5 mmol, 3 eq) and 4-nitrophenyl carbon chloridate (0.6 mmol) are added. The resulting reaction mixture is allowed to warm to room temperature and stirred for 18 hours. It is then diluted with aqueous saturated NH₄Cl and extracted with CH₂Cl₂. The combined organic layers are washed with brine, dried (Na₂SO₄) and concentrated under reduced pressure. The resulting residue is purified by silica gel chromatography (MeOH/CH₂Cl₂=0.5% to 1.2%) to afford (R)-34244Z,7Z,10Z,13Z,16Z,19Z)-docosa-4,7,10,13,16,19-hexaenamido)ethyl)disulfanyl)-3-methyl-2-(nicotinamido)butyl (1,3-dihydroxypropan-2-yl)carbamate. A mixture of 2-aminopropane-1,3-diol (0.5 mmol), (R)-3-((2-((4Z,7Z,10Z,13Z,16Z,19Z)-docosa-4,7,10,13,16,19-hexaenamido)ethyl)disulfanyl)-3-methyl-2-(nicotinamido)butyl (1,3-dihydroxypropan-2-yl)carbamate (0.5 mmol) in DMF (5 mL) is cooled to 0° C. and Hunig's base (1 mmol) is added. The reaction mixture is allowed to warm to room temperature and stirred for 18 hours. Saturated aqueous NH₄Cl (20 mL) is added and the resulting mixture is extracted with CH₂Cl₂. The combined organic layers are washed with brine, dried (Na₂SO₄) and concentrated under reduced pressure. The resulting residue is purified by silica gel chromatography MeOH/CH₂Cl₂=1.0% to 3.5%) to afford (R)-3-((2-((4Z,7Z,10Z,13Z,16Z,19Z)-docosa-4,7,10,13,16,19-hexaenamido)ethyl)disulfanyl)-3-methyl-2-(nicotinamido)butyl (1,3-dihydroxypropan-2-yl)carbamate.

Example 8

Preparation of N—((R)-1-((1,3-dihydroxypropan-2-yl)amino)-3-((2-((4Z,7Z,10Z,13Z,16Z,19Z)-docosa-4,7,10,13,16,19-hexaenamido)ethyl)disulfanyl)-3-methylbutan-2-yl)nicotinamide (IV-8)

N—((R)-3-((2-((4Z,7Z,10Z,13Z,16Z,19Z)-docosa-4,7,10,13,16,19-hexaenamido)ethyl)disulfanyl)-1-hydroxy-3-methylbutan-2-yl)nicotinamide (3.0 mmol; can be prepared as described in Example 7) is dissolved in CH₂Cl₂ (50 mL) and then the solution is cooled to 0° C. while the Dess-Martin periodinane (1.9 g, 4.5 mmol) is added. The resulting reaction mixture is allowed to warm to room temperature and stirred for 2 hours. It is then diluted with brine and extracted with CH₂Cl₂ (2×80 mL). The combined organic layers are washed with brine, dried (Na₂SO₄) and concentrated under reduced pressure to afford N—((R)-3-((2-((4Z,7Z,10Z,13Z,16Z,19Z)-docosa-4,7,10,13,16,19-hexaenamido)ethyl)disulfanyl)-3-methyl-1-oxobutan-2-yl)nicotinamide. The resulting material (1 mmol) is taken up in 10 mL of CH₂Cl₂ along with 2-aminopropane-1,3-diol (1.2 mmol), and then sodium cyanoborohydride (1.5 mmol) is added. The resulting reaction mixture is stirred at room temperature for 18 hours and then concentrated under reduced pressure. N—((R)-1-((1,3-dihydroxypropan-2-yl)amino)-3-((2-((4Z,7Z,10Z,13Z,16Z,19Z)-docosa-4,7,10,13,16,19-hexaenamido)ethyl)disulfanyl)-3-methylbutan-2-yl)nicotinamide can be purified by silica gel chromatography.

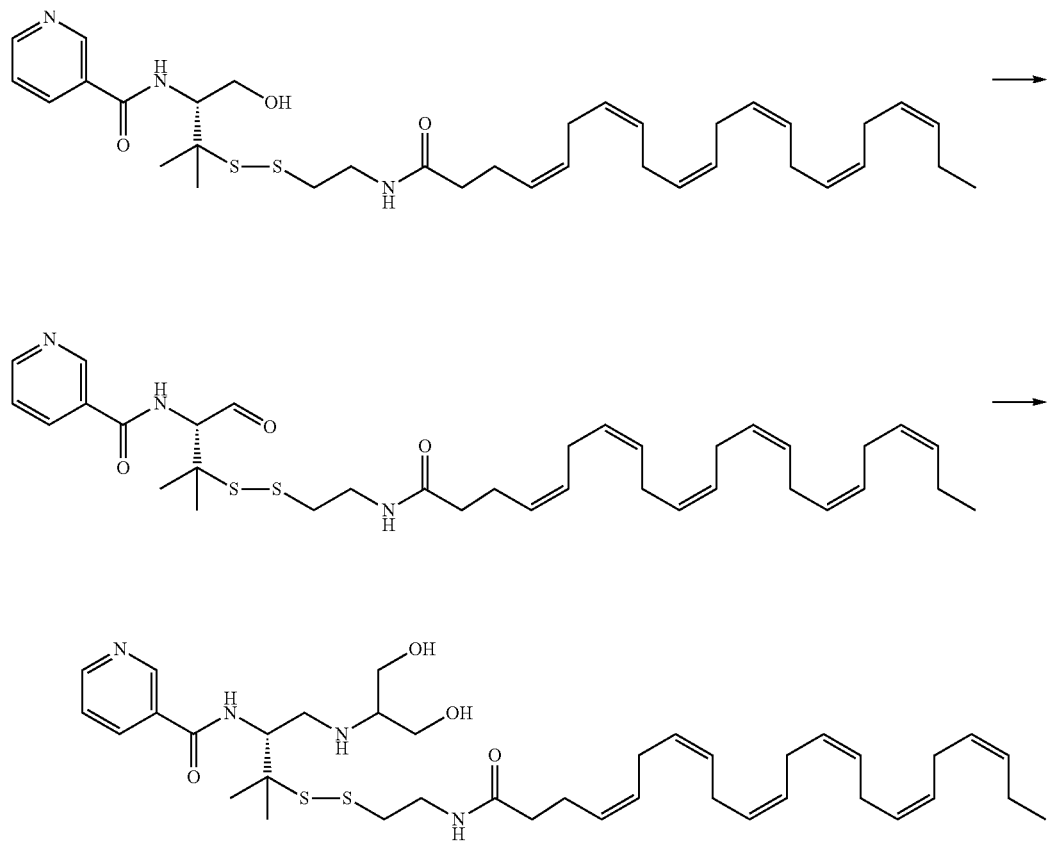

Example 9

Preparation of 1,3-dihydroxypropan-2-yl ((R)-3-((2-((4Z,7Z,10Z,13Z,16Z,19Z)-docosa-4,7,10,13,16,19-hexaenamido)ethyl)disulfanyl)-3-methyl-2-(nicotinamido)butyl)carbamate (IV-14)

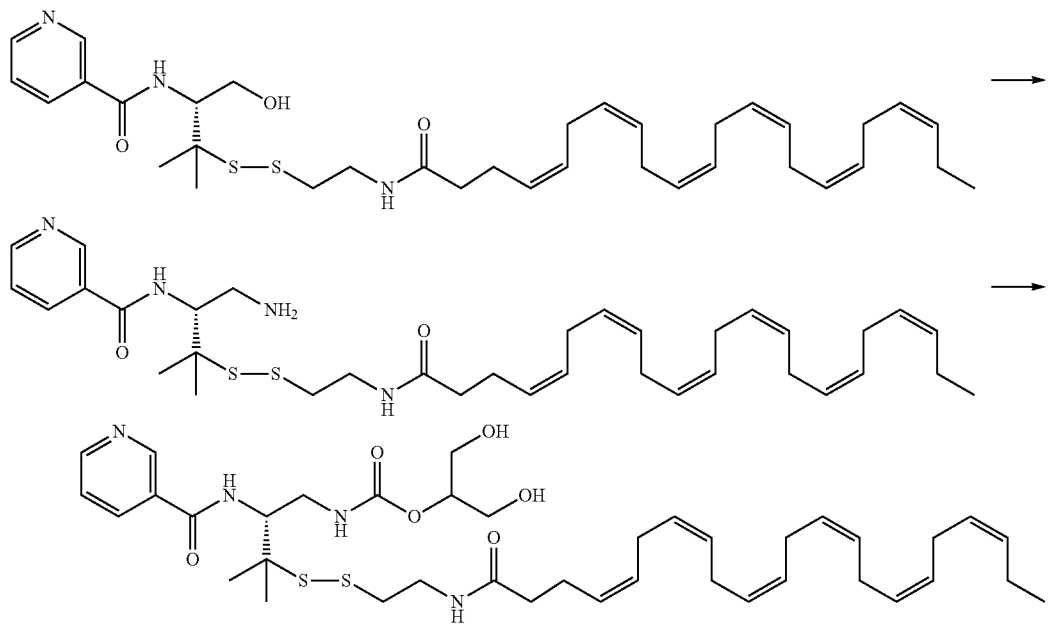

A mixture containing N—((R)-3-((2-((4Z,7Z,10Z,13Z,16Z,19Z)-docosa-4,7,10,13,16,19-hexaenamido)ethyl)disulfanyl)-1-hydroxy-3-methylbutan-2-yl)nicotinamide (3.6 mmol; can be prepared as described in Example 7), phthalimide (5.3 mmol) and triphenylphoshpine (5.3 mmol) in THF (50 mL) is cooled to 0° C. and diisopropylazodicarboxylate (DIAD, 17 mmol) is added. The reaction mixture is allowed to warm to room temperature and stirred for 2 hours. Saturated NH$_4$Cl (20 mL) is added and the resulting mixture is extracted with CH$_2$Cl$_2$ (2×50 mL). The combined organic layers are washed with brine, dried (Na$_2$SO$_4$) and concentrated under reduced pressure. The resulting residue is purified by silica gel chromatography (CH$_2$Cl$_2$/MeOH) to afford the corresponding phthalimide.

This phthalimide (2.5 mmol) is dissolved in ethanol (20 mL) and NH$_2$—NH$_2$.H$_2$O (85%, 6 mL) is added. The resulting reaction mixture is stirred for 30 minutes. The resulting reaction mixture is quenched with water (60 mL) and extracted with CH$_2$Cl$_2$ (2×50 mL). The combined organic layers are washed with brine, dried (Na$_2$SO$_4$) and concentrated under reduced pressure. The resulting residue is purified by silica gel (methanol/CH$_2$Cl$_2$) to afford N—((R)-1-amino-34244Z,7Z,10Z,13Z,16Z,19Z)-docosa-4,7,10,13,16,19-hexaenamido)ethyl)disulfanyl)-3-methylbutan-2-yl)nicotinamide.

2-Phenyl-1, 3-dioxan-5-ol (0.5 g, 2.7 mmol) is dissolved in THF (50 mL) and cooled to 0° C. while pyridine (0.44 g, 5.4 mmol) and 4-nitrophenyl chloroformate (0.84 g, 4.1 mmol) are added. The resulting reaction mixture is allowed to warm to room temperature and stirred for 2 hours. The resulting mixture is extracted with EtOAc (2×30 mL). The combined organic layers are washed with brine, dried (Na$_2$SO$_4$) and concentrated under reduced pressure. The resulting residue is purified by silica gel chromatography (hexanes/EtOAc) to afford 4-nitrophenyl (2-phenyl-1,3-dioxan-5-yl) carbonate. This material (1.0 mmol) and N—((R)-1-amino-34244Z,7Z,10Z,13Z,16Z,19Z)-docosa-4,7,10,13,16,19-hexaenamido)ethyl)disulfanyl)-3-methylbutan-2-yl)nicotinamide) (1.0 mmol) are taken up in DMF (20 mL). The mixture is cooled to 0° C. and Hunig's base (2.0 mmol) is added. The resulting reaction mixture is allowed to warm to room temperature and stirred for 18 h. Saturated aqueous NH$_4$Cl (20 mL) is added and the resulting mixture is extracted with CH$_2$Cl$_2$ (2×50 mL). The combined organic layers are washed with brine, dried (Na$_2$SO$_4$) and concentrated under reduced pressure. The resulting residue is treated with 3N HCl-dioxane (5 mL) and MeOH (1 mL) at room temperature for 2 hours and then concentrated under reduced pressure. The resulting residue is purified by silica gel chromatography (MeOH/CH$_2$Cl$_2$) to afford 1,3-dihydroxypropan-2-yl ((R)-3-((2-((4Z,7Z,10Z,13Z,16Z,19Z)-docosa-4,7,10,13,16,19-hexaenamido)ethyl)disulfanyl)-3-methyl-2-(nicotinamido)butyl)carbamate.

Example 10

Preparation of (4Z,7Z,10Z,13Z,16Z,19Z)—N-(2-mercaptoethyl)docosa-4,7,10,13,16,19-hexaenamide (I-1)

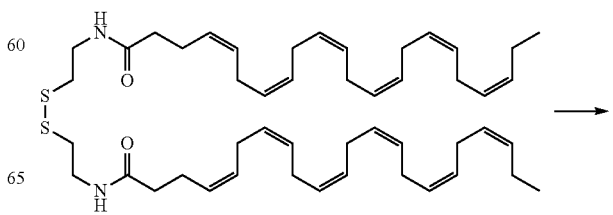

-continued

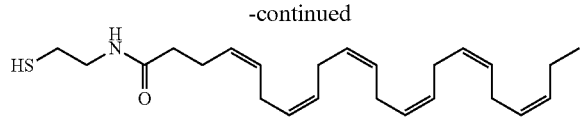

(4Z,7Z,10Z,13Z,16Z,19Z)—N-(2-Mercaptoethyl)do-cosa-4,7,10,13,16,19-hexaenamide was susceptible to oxidation to the corresponding disulfide form and was prepared freshly for assay purposes. 4Z,4'Z,7Z,7'Z,10Z,10'Z,13Z,13'Z,16Z,16'Z,19Z,19'Z)—N,N'-(disulfanediylbis(ethane-2,1-diyl))bis(docosa-4,7,10,13,16,19-hexaenamide was prepared according to the procedures outlined in WO 2012/115695. This material (125 mg, 0.162 mmol) was dissolved in EtOH (1.75 mL). Racemic-dithiothreitol (30 mg, 0.194 mmol) was subsequently added to this ethanolic solution, followed by 250 µL of 1N NaOH to bring the pH of the reaction mixture to approximately 8.5-9.0. The resulting reaction mixture was stirred at room temperature for 40 min. At this point, LC/MS analysis showed complete reduction to the desired product, namely (4Z,7Z,10Z,13Z,16Z,19Z)—N-(2-mercaptoethyl)docosa-4,7,10,13,16,19-hexaenamide. Thereafter 4.5 mL of DMSO was added to the solution to form a 50 mM DMSO stock solution of (4Z,7Z,10Z,13Z,16Z,19Z)—N-(2-mercaptoethyl)docosa-4,7,10,13,16,19-hexaenamide. This 50 mM DMSO stock solution was stored at −20° C. for use within 24 hours. Longer term storage up to 5 days requires storage of the stock solution at −80° C.

Example 11

Effect of Fatty Acid Cysteamine Conjugates on Autophagy and Cell Surface CFTR in Huh-7 or HT-29 Cells.

Compound Preparation:

The test compound was first solubilized in 100% DMSO as a 50 mM solution, and then diluted 1 to 100 in FBS as a 10× stock solution of 500 µM.

Immunoblotting:

Huh-7 cells were seeded in 10% FBS DMEM overnight. The cells media were replaced with drug diluted 1 to 10 in DMEM (final concentration 50 µm in 10% FBS DMEM). Four hours after the drug addition, cells were lysed in RIPA buffer. Cell lysates were analyzed by immunoblotting with anti-LC3A/B antibodies (Cell signaling 12741). Data were presented as LC3-II/LC3-I ratio compared to vehicle treated samples.

Confocal Microscopy:

Huh-7 cells were seeded on cover slips overnight. Cells were infected with GFP-LC3 BacMan (Life Technology) for 24 hours and treated with compound II-2. Four hours later, cells were fixed in 2% paraformaldehyde and mounted with anti-Fade with DAPI (Life Technology). Images were taken with Zeiss LSM 510, with 40× lens. To those familiar in the art, an enhancement in GFP-LC3 (green fluorescence) punctate staining is characteristic of autophagy activation.

Cell Surface Biotinylation:

HT-29 cells were seeded at 2.0×10⁶ cells in 10 mm² plates in 10% FBS DMEM overnight. The cell media was replaced with drug diluted 1 to 10 in DMEM (final concentration 50 µm in 10% FBS DMEM). 24 hours after drug addition, the cells were processed for cell surface biotinyaltion using Pierce Cell Surface Protein Isolation Kit (Thermo Scientific 89881). Briefly, cells were washed once with cold PBS and incubated with Sulfo-NHS-SS-Biotin for 30 minutes at 4° C. and reaction was stopped by adding Quenching solution. Cells were scraped and lysed and centrifuged at 10,000×g. Cell suspension were incubated with NeutrAvidin Agarose for 60 minutes at room temperature. Cell pellet (intracellular) were lysed in RIPA buffer. Protein bound to NeutrAvidin Agarose (cell surface) were eluted by SDS-PAGE sample buffer containing 50 mM DTT. Both cell surface and intracellular parts were analyzed by immunoblotting with anti-CFTR antibodies.

Results

Figure 1B:
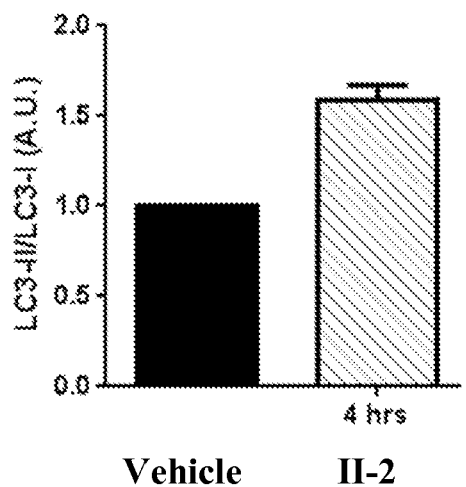
FIG. 1B is a bar graph showing the ratio of LC3-II/LC3-I when Huh-7 cells were treated with compound II-2 at a concentration of 25 µM.
Figure 2A:
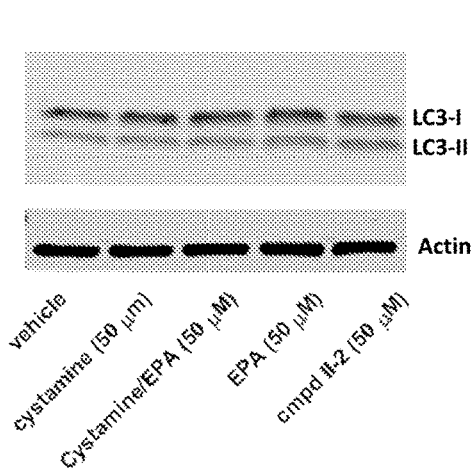
FIG. 2A is an Immunoblot of Huh-7 cells following a 2 hour exposure to cystamine, eicosapentaenoic acid ("EPA"), a combination of cystamine and EPA, or compound II-2.
Figure 2B:
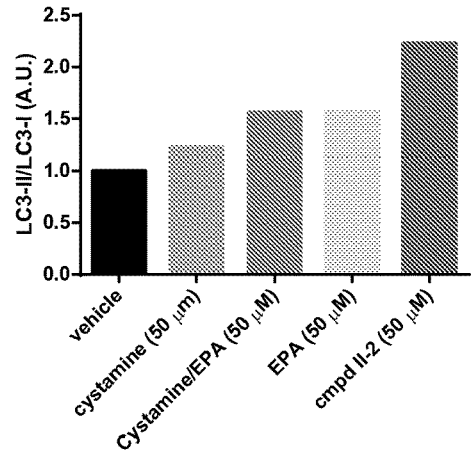
FIG. 2B is a bar chart showing the ratio of LC3-II/LC3-I when Huh-7 cells were treated with cystamine, EPA, a combination of cystamine and EPA, or compound II-2.
Figure 2C:
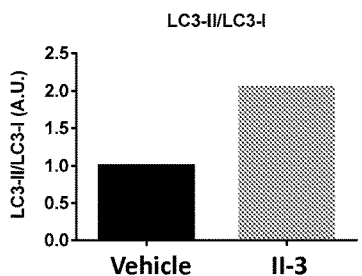
FIG. 2C is a bar chart showing the increase in autophagy, from the ratio of LC3-II/LC3-I, when HT-29 cells were incubated for 24 hours with either vehicle or compound II-3.
Figure 2D:
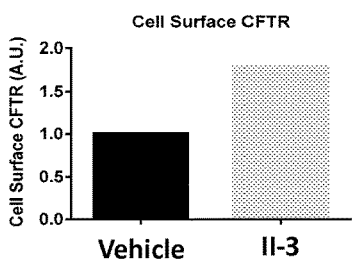
FIG. 2D is a bar chart showing the corresponding increase in cell surface CFTR when HT-29 cells were incubated for 24 hours with either vehicle or compound II-3.
Figure 2E:
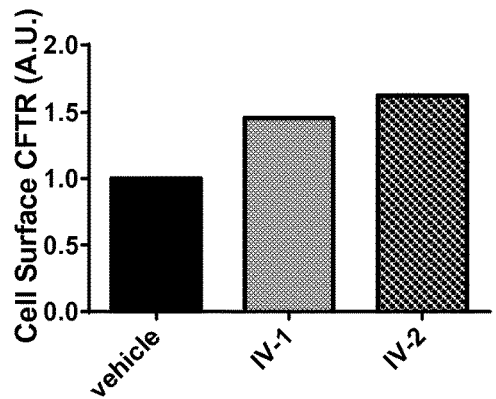
FIG. 2E is a bar chart showing the corresponding increase in cell surface CFTR when HT-29 cells were incubated for 24 hours with vehicle, IV-1 or IV-1.

In Huh cells, treatment with compound II-2 resulted in an increase in the autophagy marker LC3-II (lower band) levels (see, FIG. 1A) at both concentrations tested, namely 25 and 50 µM of the fatty acid cysteamine derivative II-2. Quantitative analysis at the lower concentration of 25 µM revealed that treatment with compound II-2 increased the ratio of LC3-II to LC3-I (FIG. 1B), indicating an increased conversion of LC3-I to LC3-II, a molecular marker for autophagy formation. As noted in Levine and Kroemer (2008) CELL, 132, p. 27-42, an increased ratio of LC3-II/LC3-I indicates that autophagy has been activated. The same incubation experiment was carried out in HT-29 cells with compound II-3. As shown in FIG. 2C, autophagy was activated when HT-29 cells was incubated with compound II-3 (50 µM), as reflected by the increase in the ratio of LC3-II to LC3-I, when compared to the vehicle control group. As autophagy was being activated in these HT-29 cells, there was a corresponding increase in the cell surface CFTR, when compared to the vehicle control group (FIG. 2D). FIG. 2E summarizes the results when HT-29 cells were incubated with 50 µM of compounds IV-11 and IV-12. Since autophagy was activated, there was a corresponding increase in the cell surface CFTR for the treatment groups containing either compound IV-11 or IV-12.

Example 12

Synergistic Properties of Fatty Acid Cysteamine Conjugates in Huh-7 or HT-29 Cells The same experimental procedure detailed in Example 11 was used, except that 2 hours after the drug addition, cells were lysed in RIPA buffer, instead of the previously described 4 hours. Cell lysates were again analyzed by immunoblotting with anti-LC3A/B antibodies (Cell Signaling Technology 12741). Data were presented as LC3-II/LC3-I ratio compared to vehicle treated samples. As shown in FIG. 2A, treatment with compound II-2 at 50 µM resulted in a synergistic increase in the autophagy marker LC3-II (lower band) when compared with similar treatment with either cystamine (50 µM), EPA (50 µM) or a combination of cystamine (50 µM) and EPA (50 µM). Quantitative analysis revealed a two-fold increase in the ratio of LC3-II to LC3-I when compared to the vehicle control (FIG. 2B). This demonstrated an increase in the conversion of LC3-I to LC3-II, a known molecular marker for activation of autophagy. Compound II-2 showed a synergistic activation of autophagy; an effect that was achieved when the individual components or a combination of the individual components (i.e. cystamine and EPA) were used.

Figure 3A:
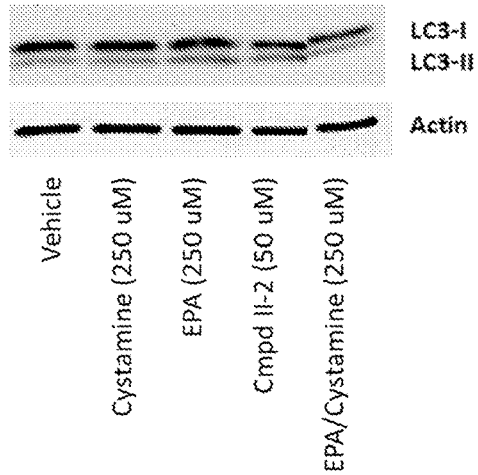
FIG. 3A is an Immunoblot.
Figure 3B:
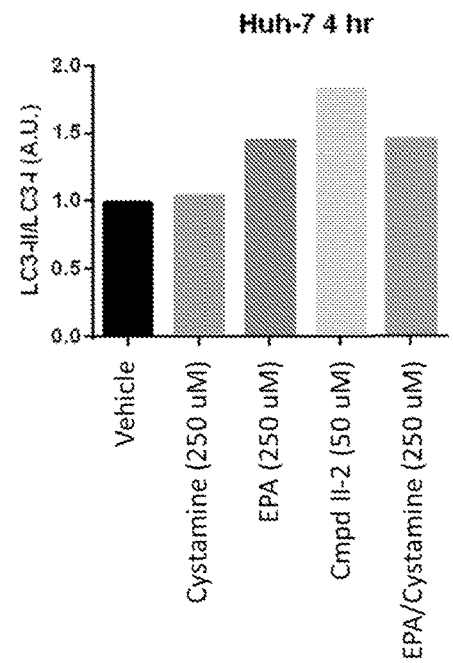
FIG. 3B is a bar chart showing the ratio of LC3-II/LC3-I when Huh-7 cells were treated with cystamine (250 µM), EPA (250 µM), a combination of cystamine and EPA (250 µM each) or compound II-2 (50 µM).

This same synergy experiment was repeated in Huh-7 cells after a 4 hour treatment with compound II-2 along with a higher concentration of the individual components (250 µM each of cystamine, EPA or a combination of cystamine and EPA). The results are summarized in FIGS. 3A and 3B. Again, treating cells with 50 µM of compound II-2 resulted in a synergistic and higher degree of activation of autophagy, as indicated by the greater ratio of LC3-II to LC3-I. This degree of activation of autophagy was not achieved even with much higher concentrations of cystamine (250 µM), EPA (250 µM) or a combination of cystamine and EPA (250 µM each).

Figure 4:
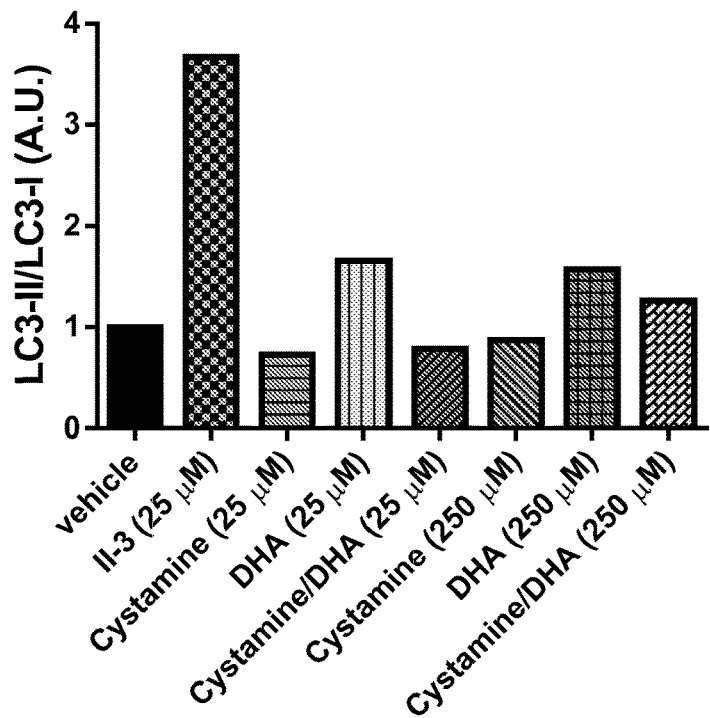
FIG. 4 is a bar chart showing the ratio of LC3-II/LC3-I when HT-29 cells were treated for 24 hours with: (1) vehicle control group; (2) compound II-3 (25 µM); (3) cystamine (25 µM); (4) DHA (25 µM); (5) a combination of cystamine (25 µM) and DHA; (6) cystamine (250 µM); (7) DHA (250 µM); and (8) a combination of cystamine (250 µM) and DHA (250 µM).

This same synergy experiment was repeated with compound II-3 using HT-29 cells. In this experiment, HT-29 cells were incubated for 24 hours with each of the following treatment groups: 1) vehicle control group; 2) cystamine (25 µM); 3) DHA (25 µM); 4) a combination of cystamine (25 µM) and DHA; 5) cystamine (250 µM); 6) DHA (250 µM); 7) a combination of cystamine (250 µM) and DHA (250 µM); 8) compound II-3 (25 µM). The results are summarized in FIG. 4. The result shown represented the average of three separate measurements. HT-29 cells treated with 25 µM of compound II-3 showed a synergistic and higher degree of activation of autophagy, as indicated by the greater ratio of LC3-II to LC3-I, when compared to the vehicle control group. This degree of activation of autophagy was not achieved with any of the following treatment groups: 1) vehicle control group; 2) cystamine (25 µM); 3) DHA (25 µM); 4) a combination of cystamine (25 µM) and DHA; 5) cystamine (250 µM); 6) DHA (250 µM); 7) a combination of cystamine (250 µM) and DHA (250 µM). As shown in FIG. 4, the autophagy activation activity that was associated with compound II-3 could not be replicated treating these primary CF cells with the individual components (i.e. cystamine and DHA, 25 µM or 250 µM) or a combination of the individual components.

Example 13

Effect of Fatty Acid Cysteamine Conjugates on Primary CF Human Bronchial Epithelial Cells, Homozygous for ΔF508 CFTR Deletion Mutation: Immunoblot Analysis and Immunoprecipitation It is contemplated that compounds of the invention may be useful in the treatment of CF because of their ability to activate autophagy. The compounds of the invention were evaluated in the following cellular assay to determine their ability to rescue the defective, mutant CFTR to the cell membrane.

Primary cells from homozygous ΔF508 CF patients were obtained from either Asterand Bioscience (Detroit, Mich.) or ChanTest, a Charles River Company (Cleveland, Ohio). Cells then were treated at various concentrations to determine the compound's ability to restore the defective CFTR. As reviewed in Derichs (2013) EUR. RESP. REV., 22, p. 58-65, a successful detection of the mutant CFTR band C by immunoblot indicates that the defective CFTR can be rescued to the cell membrane.

Compound Preparation

Compounds of the invention were first solubilized in 100% DMSO as 50 mM solution, and then diluted 1 to 100 in FBS as a 10× stock solution of 500 µM.

Immunoblotting

Primary CF cells (homozygous ΔF508, source: ChanTest, KKCFFT004I) were prepared and grown on Snapwell™ filter inserts according to the procedures outlined in Amaral, M. D. and Kunzelmann, K. (Eds) CYSTIC FIBROSIS, METHODS IN MOLECULAR BIOLOGY, 741, DOI 10.1007/978-1-61779-117-8_4 Springer Science+Business Media, LLC 2011). Primary CF cells were kept in differentiation media consisting of Dulbecco's MEM (DMEM)/F12, Ultroser-G (2.0%; Pall, Catalog #15950-017), fetal clone II (2%), insulin (2.5 µg/ml), bovine brain extract (0.25%; Lonza, Kit #CC-4133, component # CC-4092C), hydrocortisone (20 nM), triiodothyronine (500 nM), transferrin (2.5 µg/ml: Invitrogen, Catalog #0030124SA), ethanolamine (250 nM), epinephrine (1.5 µM), phosphoethanolamine (250 nM), and retinoic acid (10 nM). The test compounds, solubilized in FBS according to the procedure outlined above and diluted to the desired concentration, were then added to the individual Snapwell™ filter inserts in the differentiation media at 37° C. Twenty-four hours after the drug addition, cells were snap frozen and later lysed in RIPA buffer. The amounts of proteins were determined by Bio-Rad protein assay. Fifty µg of total cell lysates were analyzed by immunoblotting with anti-CFTR, anti-Beclin-1, anti-p62 and anti-LC3 antibodies. The immuno-activity was normalized with actin as the loading control. Data were presented as CFTR-band-C/actin, Beclin-1/actin, p62/actin and LC3-II/LC3-I ratio compared to vehicle treated samples. Antibodies against CFTR clone M3A7 (Cell Signaling Technology, 2269), LC3A/B antibodies (Cell signaling, 12741), Beclin-1 (Cell Signaling Technology, 3495), p62 (Cell Signaling Technology, 5114) and β-actin (Cell Signaling Technology, 4970) were used as primary antibodies.

Figure 5A:
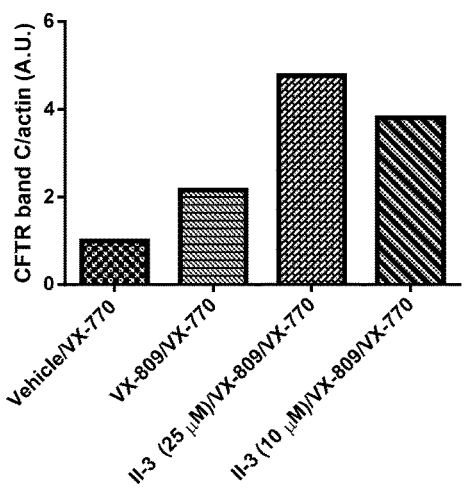
FIG. 5A is a bar chart showing the CFTR band C data of primary CF cells (homozygous for ΔF508) after a 24 hr incubation with: 1) vehicle+VX-770 (100 nM); 2) a combination of VX-809 (3 µM)+VX-770 (100 nM); 3) a combination of compound II-3 (25 µM)+VX-809 (3 µM)+VX-770 (100 nM); 4) a combination of compound II-3 (10 µM)+VX-809 (3 µM)+VX-770 (100 nM).

Compound II-3 was incubated in these primary CF cells for 24 hours and the amount of CFTR band C that was functionally rescued was quantitated by immunoblotting. FIG. 5A summarizes the results when these primary CF cells (homozygous for ΔF508, ChanTest, KKCFFT004I) were incubated for 24 hours with the following treatment groups: 1) vehicle+VX-770 (100 nM); 2) a combination of VX-809 (3 µM)+VX-770 (100 nM); 3) a combination of compound II-3 (25 µM)+VX-809 (3 µM)+VX-770 (100 nM); 4) a combination of compound II-3 (10 µM)+VX-809 (3 µM)+VX-770 (100 nM). Treatment of primary CF cells with a combination VX-809+VX-770 resulted in an increase in the amount of the CFTR band C. As shown in FIG. 5A, a combination of compound II-3 with VX-809 and VX-770 produced a more significant increase in the amount of the CFTR band C. The effect was also dose-dependent. The result shown represented the average of three separate measurements.

Figure 5B:
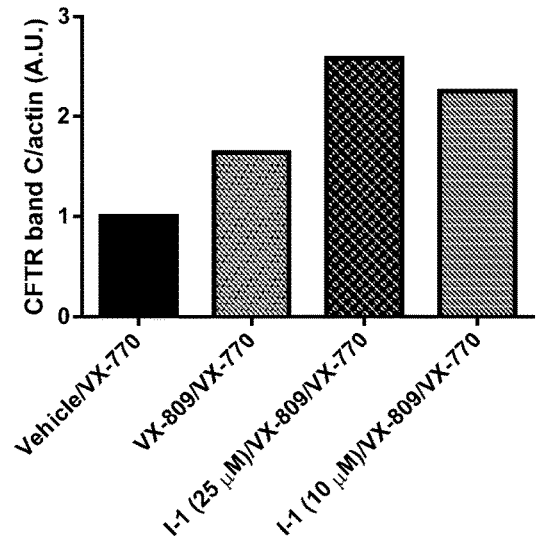
FIG. 5B is a bar chart showing the CFTR band C data of primary CF cells (homozygous for ΔF508) after a 24 hour incubation with (1) vehicle+VX-770 (100 nM); (2) a combination of VX-809 (3 µM)+VX-770 (100 nM); (3) a combination of compound I-1 (25 µM)+VX-809 (3 µM)+VX-770 (100 nM); and (4) a combination of compound I-1 (10 µM)+VX-809 (3 µM)+VX-770 (100 nM).

Compound I-1 was also incubated in these primary CF cells for 24 hours and the amount of CFTR band C that was functionally rescued was quantitated by immunoblotting. FIG. 5B summarizes the results when these primary CF cells (homozygous for ΔF508, ChanTest, KKCFFT004I) were incubated for 24 hours with the following treatment groups: 1) vehicle+VX-770 (100 nM); 2) a combination of VX-809 (3 µM)+VX-770 (100 nM); 3) a combination of compound I-1 (25 µM)+VX-809 (3 µM)+VX-770 (100 nM); 4) a combination of compound I-1 (10 µM)+VX-809 (3 µM)+VX-770 (100 nM). As shown in FIG. 5B, a combination of compound I-1 with VX-809 and VX-770 produced a more significant increase in the amount of the CFTR band C. The effect was also dose-dependent. The result shown represented the average of three separate measurements.

Figure 5C:
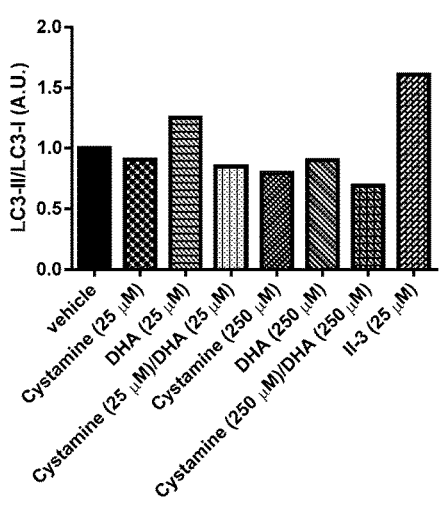
FIG. 5C is a bar chart showing the ratio of LC3-II/LC3-I when primary CF cells (homozygous ΔF508) after a 24 hour incubation with: (1) vehicle control group; (2) cystamine (25 µM); (3) DHA (25 µM); (4) a combination of cystamine (25 µM) and DHA (25 µM); (5) cystamine (250 µM); (6) DHA (250 µM); (7) a combination of cystamine (250 µM) and DHA (250 µM); and (8) compound II-3 (25 µM).

The same type of synergy experiment was carried out as in Example 12 using these primary CF cells. FIG. 5C summarizes the results when primary CF cells (homozygous ΔF508, source, ChanTest, KKCFFT004I) were incubated for 24 hours with the following treatment groups: 1) vehicle control group; 2) cystamine (25 µM); 3) DHA (25 µM); 4) a combination of cystamine (25 µM) and DHA (25 µM); 5) cystamine (250 µM); 6) DHA (250 µM); 7) a combination of cystamine (250 µM) and DHA (250 µM); 8) compound II-3 (25 µM). As shown in FIG. 5C, compound II-3 (at 25 µM) activated autophagy in primary CF cells, as indicated by the increase in the ratio of LC3-II to LC3-I, compared to the vehicle control group. This level of autophagy activation could not be replicated by treating these primary CF cells with the individual components (i.e. cystamine and DHA, 25

µM or 250 µM) or a combination of the individual components. The result shown represented the average of three separate measurements.

Figure 5D:
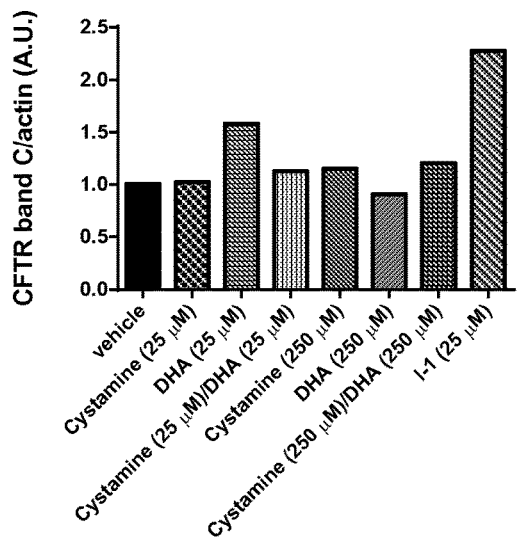
FIG. 5D is a bar chart showing the ratio of CFTR Band C/actin when primary CF cells (homozygous ΔF508) after the 24 hour incubation with: (1) vehicle control group; (2) cystamine (25 µM); (3) DHA (25 µM); (4) a combination of cystamine (25 µM) and DHA (25 µM); (5) cystamine (250 µM); (6) DHA (250 µM); (7) a combination of cystamine (250 µM) and DHA (250 µM); and (8) compound I-1 (25 µM).

The synergy experiment in primary CF cells could also be used to assess the level of the CFTR band C that could be functionally rescued. FIG. 5D summarizes the results when primary CF cells (homozygous ΔF508, source, ChanTest, KKCFFT004I) were incubated for 24 hours with the following treatment groups: 1) vehicle control group; 2) cystamine (25 µM); 3) DHA (25 µM); 4) a combination of cystamine (25 µM) and DHA (25 µM); 5) cystamine (250 µM); 6) DHA (250 µM); 7) a combination of cystamine (250 µM) and DHA (250 µAA); 8) compound I-1 (25 µM). As shown in FIG. 5D, there was a significant increase in the amount of the CFTR band C when primary CF cells were treated with 25 µM of compound I-1. This effect could not be replicated by these primary CF cells with the individual components (i.e. cystamine and DHA, 25 µM or 250 µM) or a combination of the individual components. The result shown represented the average of three separate measurements.

Figure 5E:
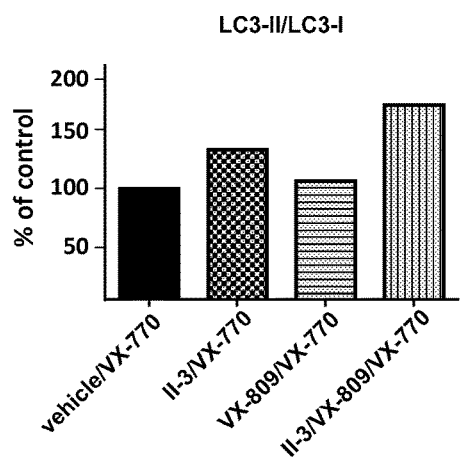
FIG. 5E is a bar chart showing the ratio of LC3-II/LC3-I when primary CF cells (homozygous ΔF508) were treated with: (1) vehicle+VX-770 (100 nM); (2) compound II-3 (25 µM)+VX-770 (100 nM); (3) VX-809 (3 µM)+VX-770 (100 nM); and (4) compound II-3 (25 µM)+VX-809 (3 µM)+VX-770 (100 nM).
Figure 5F:
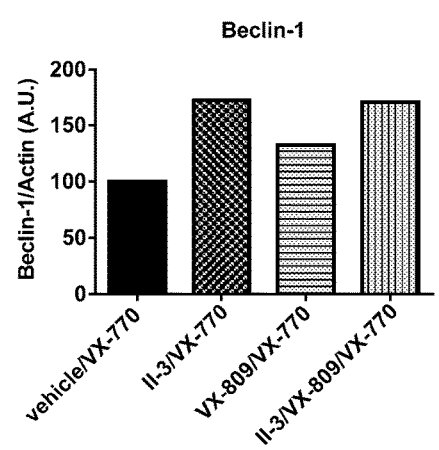
FIG. 5F is a bar chart showing the ratio of Beclin-1/actin when primary CF cells (homozygous ΔF508) were treated with: (1) vehicle+VX-770 (100 nM); (2) compound II-3 (25 µM)+VX-770 (100 nM); (3) VX-809 (3 µM)+VX-770 (100 nM); and (4) compound II-3 (25 µM)+VX-809 (3 µM)+VX-770 (100 nM).
Figure 5G:
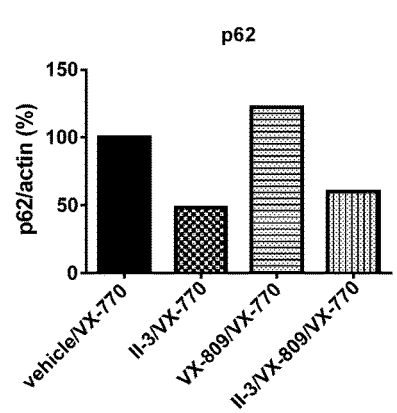
FIG. 5G is a bar chart showing the ratio of p62/actin when primary CF cells (homozygous ΔF508) were treated with: (1) vehicle+VX-770 (100 nM); (2) compound II-3 (25 µM)+VX-770 (100 nM); (3) VX-809 (3 µM)+VX-770 (100 nM); and (4) compound II-3 (25 µM)+VX-809 (3 µM)+VX-770 (100 nM).
Figure 5H:
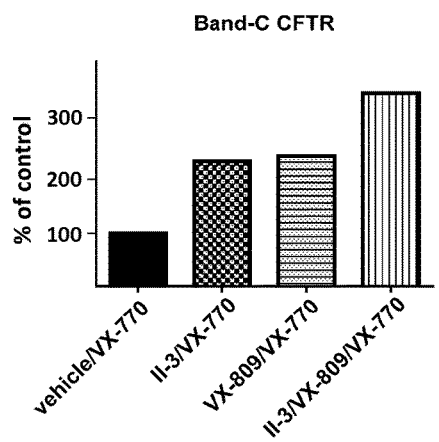
FIG. 5H is a bar chart showing the CFTR band C data when primary CF cells (homozygous ΔF508) were treated with: (1) vehicle+VX-770 (100 nM); (2) compound II-3 (25 µM)+VX-770 (100 nM); (3) VX-809 (3 µM)+VX-770 (100 nM); and (4) compound II-3 (25 µM)+VX-809 (3 µM)+VX-770 (100 nM).

FIGS. 5E, 5F, 5G and 5H summarize the results from a mechanism of action study on compound II-3 using primary CF cells (homozygous ΔF508). The result shown represented the average of three separate measurements. In CF, autophagy is depressed. As autophagy is being restored with compound II-3, an autophagy activator, one should observe a corresponding increase in Beclin-1, a decrease in the amount of p62, and finally an increase in the amount of the CFTR band C. Primary CF cells (homozygous ΔF508) were treated with the following treatment groups for 24 hr: 1) vehicle+VX-770 (100 nM); 2) compound II-3 (25 µM)+VX-770 (100 nM); 3) VX-809 (3 µM)+VX-770 (100 nM); 4) compound II-3 (25 µM)+VX-809 (3 µM)+VX-770 (100 nM). FIG. 5E showed that as autophagy was being restored, the 2 treatment groups that included compound II-3 showed the expected increase in the ratio of LC3-II to LC3-I. Since autophagy was increased, there was a corresponding increase in the level of Beclin-1 (FIG. 5F) and a decrease in the level of p62 (FIG. 5G) with the 2 treatment groups that included compound II-3. A decrease in the level of p62 allowed some of the misfolded ΔF508 CFTR to escape sequestration in the endoplasmic reticulum and be transported to the cell surface. This was reflected in the increase in the CFTR band C. As shown in FIG. 5H, the combination of compound II-3 (25 µM)+VX-809 (3 µM)+VX-770 (100 nM) showed a significant additive effect when compared with the VX-809 (3 µM)+VX-770 (100 nM) combination.

Example 14

Evaluation of Compounds in Fisher Rat Thyroid Epithelial Cells Via Ussing Chamber for Functional Rescue of CFTR Ion Channel Activity.

The most prevalent disease causing mutation of the CF transmembrane conductance regulator (CFTR) chloride channel is the deletion of phenylalanine at position 508 in the primary sequence of CFTR (ΔF508-CFTR). This mutation causes a trafficking defect resulting in a severe reduction of ΔF508-CFTR protein at the cell surface. The trafficking defect can be corrected by incubation at low temperature (27° C. overnight) or pharmacologically by small molecules and CFTR correctors. Chloride transport function of Fisher Rat Thyroid (FRT) epithelial cells overexpressing ΔF508-CFTR in monolayers grown on Snapwell™ filter inserts will be monitored as the CFTR agonist evoked short circuit ($I_{SC}$) current output of an Ussing epithelial voltage clamp apparatus. An objective of this study is to measure the ability of test compounds to restore function to defective ΔF508-CFTR in FRT epithelial cell monolayers.

Measurement of corrector efficacy is divided into two phases. The initial phase is incubation of epithelia with the test compounds for a period of time (that can range from 2 hours to one or two days) in a 37° C. incubator and the second phase is measurement of epithelial ΔF508-CFTR chloride channel current with an epithelial voltage clamp (Ussing assay). The short circuit current ($I_{SC}$) is measured under short circuit conditions (0 mV transepithelial potential). The $I_{SC}$ magnitude is an index of corrector efficacy and is compared to vehicle and positive control.

Cryopreserved FRT cells stably transfected with ΔF508-CFTR cDNA (Pedemonte et al. (2005) J. CLIN. INVEST., 115, p. 2564-2571) were expanded and plated on Snapwell™ filters for measurement of short circuit current in an Ussing apparatus (Physiologic Instruments, Inc., Sand Diego, Calif.). Cells were grown in Coon's modification of Ham's F-12 media supplemented with zeocin and G-418.

To conduct the assay, a compound of the invention was solubilized as follows:
 1) Prepare 25 mM stock solution in 100% DMSO.
 2) Dilute 12 µL of 25 mM stock solution in 1.20 mL of FBS to make 250 µM intermediate dilution 10× stock (1% DMSO, 99% FBS). Gently vortex all solutions until the solution becomes clear.
 3) Prepare final dilution of 10 µM in 10 mL of Coon's media per well (4 wells×2 mL per well bottom+0.2 mL per insert top=8.8 mL and 1.2 mL reserve for handling losses) by addition of 400 µL of 10× stock and 600 µL of 10× carrier (1% DMSO, 99% FBS) to 9000 µL of Coon's media.

For this example, the test compound was solubilized and added to the appropriate inserts of Ussing chambers (n=4 for each test compound, final test concentration of 10 µM). A DMSO vehicle control and a positive control (VX-809 at 3 µM) were also used. For this particular example, all the test articles, including the positive control, were incubated with the cells for a period of 4 hours. The FRT cell monolayers grown on Snapwell™ filter inserts were transferred to Physiologic Instruments Ussing recording chambers (Physiologic Instruments, Inc., San Diego, Calif.) and superfused with HB-PS on the basolateral side and 78CF-PS on the apical side. One or more 6-channel or 8-channel Physiologic Instruments VCC MC6 or VCC MC8 epithelial voltage clamps were then used in combination to record the short circuit current ($I_{SC}$) during the entire run. To initiate the $I_{SC}$ measurement, amphotericin (100 µM) was added to the basolateral side of the Snapwell™ filter insert to permeabilize the epithelial cells for 15 min. Forskolin (10 µM), IBMX (100 µM), Genistein (20 µM) and the $CFTR_{inh}$-172 (20 µM) were added sequentially after the following incubation periods (15 min, 20 min, 10 min, 15 min and 15 min respectively). Data acquisition and analyses were performed using iWorx data acquisition hardware and Labscribe 2 software (iWorx, Dover, N.H.). Comparison of agonist evoked $I_{SC}$ among both corrector positive control, negative control and test article treated epithelia was obtained with one-way ANOVA followed by Dunnett's multiple comparison test and Student's t-test when appropriate. Significant correction was defined at the level of P<0.05.

Figure 6:
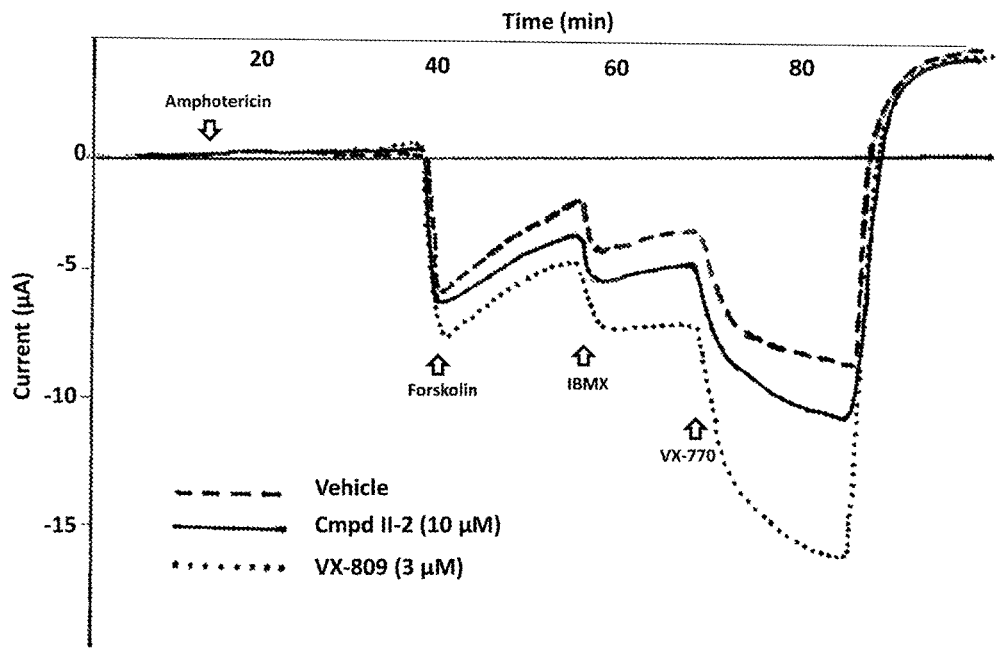
FIG. 6 is a graph showing the Fisher Rat Thyroid (FRT)/ΔF508 CFTR epithelia response when cells were treated with 10 µM of compound II-2 for 4 hours (with 3 µM of VX-809 as the positive control).

In this assay, the positive control VX-809 was able to functionally rescue the defective CFTR under the test conditions when the cells were treated sequentially with Forskolin, IBMX and then with the CFTR potentiator Genistein. To test for CFTR specificity, the commercially available inhibitor CFTR$_{inh}$-172 (which has chemical name (E)-4-((4-oxo-2-thioxo-3-(3-(trifluoromethyl)phenyl)thiazolidin-5-ylidene)methyl)benzoic acid (CAS no. 307510-92-5)) was added near the completion of the run to bring the short circuit current down to the baseline. Compound II-2 (10 μM) was evaluated in the FRT cells Ussing chamber using this assay protocol. Traces of the short circuit currents (I$_{SC}$) over time (min) were then obtained from this type of experiment and this is shown in FIG. 6. Compound II-2 was able to functionally rescue CFTR function because there was an increase in the short circuit current, when compared to the vehicle control group.

Figure 7A:
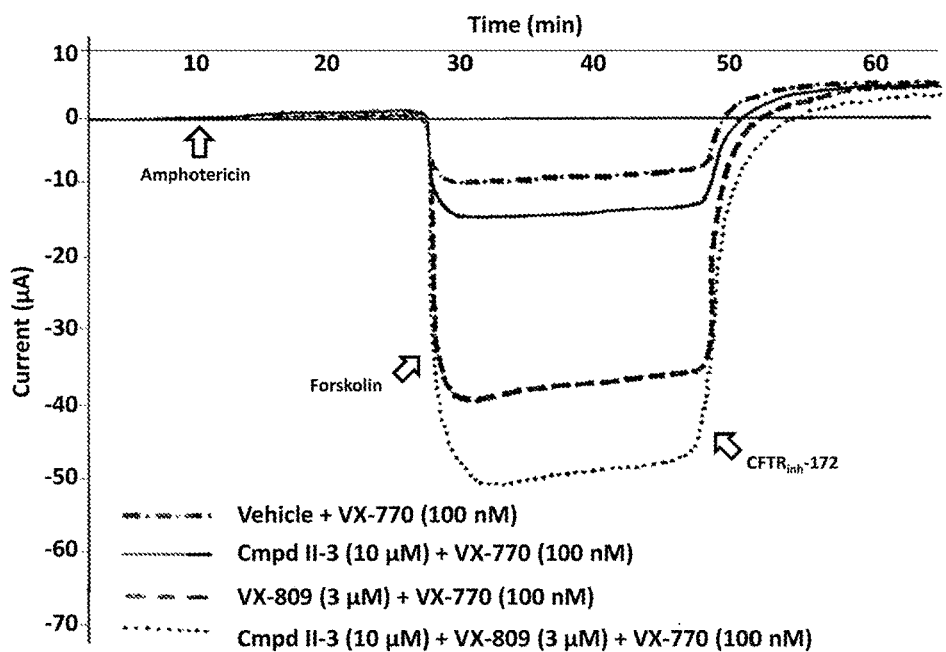
FIG. 7A is a graph showing a short circuit current ($I_{SC}$) trace generated when FRT cells were treated for 24 hours with: (1) vehicle+VX-770 (100 nM); (2) compound II-3 (10 µM)+VX-770 (100 nM); (3) the positive control group, VX-809 (3 µM)+VX-770 (100 nM); and (4) compound II-3 (10 µM)+VX-809 (3 µM)+VX-770 (100 nM). Short circuit currents were generated in an Ussing chamber assay.
Figure 7B:
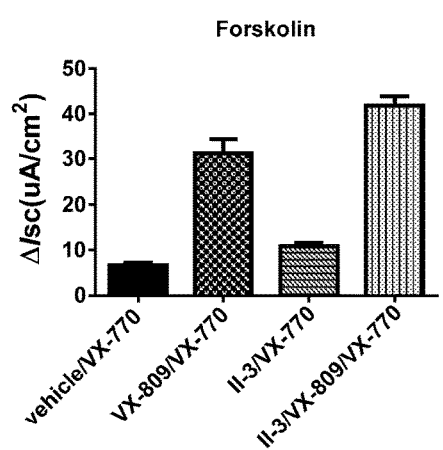
FIG. 7B is a bar chart showing the quantification of the steady state response of the traces shown in FIG. 7A upon the addition of Forskolin, as measured by $\Delta I_{SC}$ (µA/cm$^2$)
Figure 7C:
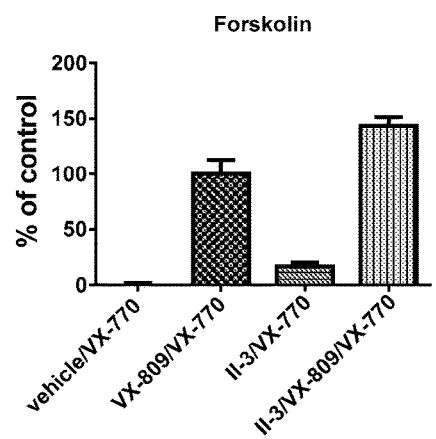
FIG. 7C is a bar chart showing the quantification of the steady state response of the traces shown in FIG. 7A upon the addition of Forskolin, expressed as % of control.
Figure 7D:
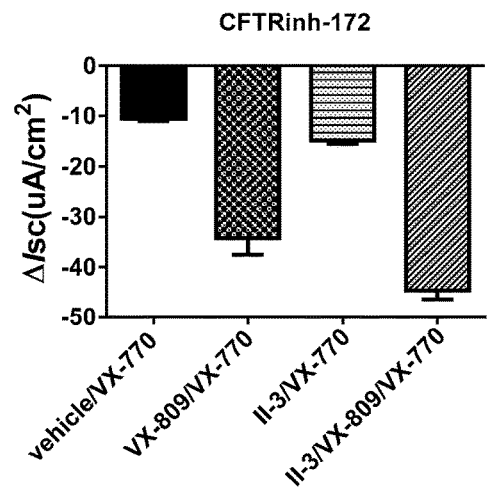
FIG. 7D is a bar chart showing the quantification of steady state response of the traces shown in FIG. 7A upon the addition of the CFTR$_{inh}$-172, as measured by $\Delta I_{SC}$ (µA/cm$^2$)
Figure 7E:
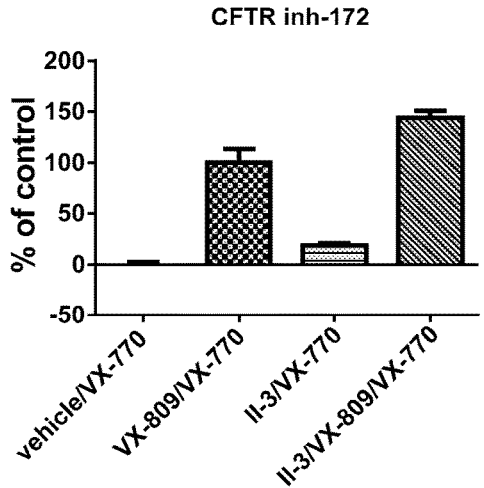
FIG. 7E is a bar chart showing the quantification of steady state response of the traces shown in FIG. 7A upon the addition of the CFTR$_{inh}$-172, expressed as % of control.

An alternative protocol to this assay involved the chronic pre-incubation of compounds of the invention along with VX-770 or the combination of VX-809 and VX-770. With this protocol, the compounds of the invention were pre-incubated with either VX-770 or a combination of VX-770 and VX-809 for 24 hours using the same protocols outlined above. Amphotericin (100 μM) was first added to permeabilize the cell membrane. Fifteen minutes after the addition of amphotericin, Forskolin (20 μM) was added. Twenty minutes after the addition of Forskolin, the commercially available inhibitor CFTR$_{inh}$-172 was added. The reaction was then terminated 15 minutes after the addition of the CFTR$_{inh}$-172. A representative trace of the short circuit currents was then obtained from this type of experiment. The functional activity of the compounds of the invention was assessed when comparison was made between the vehicle group and the positive control group. For all the Ussing chamber experiments, the positive control was a combination of the CFTR corrector VX-809 (3 μM) and the CFTR potentiator VX-770 (100 nM). Quantification of the short circuit currents was carried out to determine the ΔI$_{SC}$ at two different time points, first upon the addition of Forskolin and later upon the addition of the CFTR$_{inh}$-172 (For a more comprehensive description of the assay, please refer to Van Goor et al. (2011) PNAS, 108, no. 46, p. 18843-18848). FIGS. 7A, 7B, 7C, 7D and 7E summarize the data when the FRT cells were incubated for 24 hours with the following treatment groups: 1) vehicle+VX-770 (100 nM); 2) compound II-3 (10 μM)+VX-770 (100 nM); 3) the positive control group, VX-809 (3 μM)+VX-770 (100 nM); 4) compound II-3 (10 μM)+VX-809 (3 μM)+VX-770 (100 nM). Each treatment group was evaluated with 4 separate inserts. As shown in FIG. 7A, compound II-3 was functionally active in this assay, as noted by the increase in the short circuit current; the effect was most pronounced with the combination of II-3 (10 μM)+VX-809+VX-770. FIG. 7B shows the quantification of the steady state response upon the addition of Forskolin, as measured by ΔI$_{SC}$ (μA/cm$^2$); whereas FIG. 7C shows the same response, expressed as % of control (the positive control VX-809+VX-770 was expressed as 100%). The combination of II-3 (10 μM)+VX-770 produced a modest response, when compared with the vehicle+VX-770 group. The combination consisting of II-3 (10 μM)+VX-809+VX-770 produced a significant 143.6% increase over the positive control. FIG. 7D shows the quantification of steady state response upon the addition of the CFTR$_{inh}$-172, as measured by ΔI$_{SC}$ (μA/cm$^2$); whereas FIG. 7E shows the same response, expressed as % of control (the positive control VX-809+VX-770 was expressed as 100%). Again, at this time point, the combination consisting of II-3 (10 μM)+VX-809+VX-770 produced a significant 144.0% increase over the positive control group.

Example 15

Evaluation of Compounds in Primary CF Bronchial Epithelial Cells (Homozygous ΔF508) Via Ussing Chamber for Functional Rescue of CFTR Ion Channel Activity.

Primary CF cells (homozygous ΔF508, source: ChanTest, KKCFFT004I) were prepared and grown on Snapwell™ filter inserts according to the procedures outlined in Amaral, M. D. and Kunzelmann, K. (Eds) Cystic Fibrosis, Methods in Molecular Biology 741, DOI 10.1007/978-1-61779-117-8_4 Springer Science+Business Media, LLC 2011). Primary CF cells were kept in differentiation media consisting of Dulbecco's MEM (DMEM)/F12, Ultroser-G (2.0%; Pall, Catalog #15950-017), fetal clone II (2%), insulin (2.5 μg/ml), bovine brain extract (0.25%; Lonza, Kit #CC-4133, component # CC-4092C), hydrocortisone (20 nM), triiodothyronine (500 nM), transferrin (2.5 μg/ml: Invitrogen, Catalog #0030124SA), ethanolamine (250 nM), epinephrine (1.5 μM), phosphoethanolamine (250 nM), and retinoic acid (10 nM).

The test compounds were solubilized in FBS as follows: 100 μL of a 25 mM DMSO stock solution of the test compound was diluted in 10.0 mL of FBS in a centrifuge tube to prepare an intermediate 250 μM intermediate dilution 10× stock (1% DMSO, 99% FBS). This solution was allowed to sit in the centrifuge tube at room temperature for 1 hour and then discarded; a new 250 μM 10× stock was then prepared in the conditioned centrifuge tube. This 10× stock solution was used to prepare the subsequent test article concentrations. For instance, the 25 μM concentration in 10 mL of differentiation media was prepared by adding 1000 μL of the 10× stock solution to 9000 μL of differentiation media. This 25 μM solution was allowed to sit in the centrifuge tube at room temperature for 1 hour and then discarded; and a new 25 μM solution was then prepared in the conditioned centrifuge tube. The 10 μM concentration in 10 mL of differentiation media was prepared by adding 400 μL of the 10× stock solution to 9000 μL of differentiation media and 600 μL of 1% DMSO, 99% FBS solution. The subsequent 3 and 1 μM concentrations in 10 mL of differentiation media were prepared in the same manner by adding the appropriate volume of the 10× stock solution to the differentiation media and 1% DMSO, 99% FBS solution. The same conditioning step described above was used in all the dilution steps.

To carry out the Ussing chamber assay, the test compounds, solubilized in FBS according to the procedure outlined above and diluted to the desired concentration, were then added to the individual Snapwell™ filter inserts in the differentiation media at 37° C. Twenty-four hours after the drug addition, the inserts were transferred to Physiologic Instruments Ussing recording chambers (Physiologic Instruments, Inc.; San Diego, Calif.) and maintained in both the apical and basolateral chambers with a HEPES buffered physiological saline (HB-PS) with composition (in mM): NaCl, 137; KCl, 4.0; CaCl$_2$, 1.8; MgCl$_2$, 1; HEPES, 10; Glucose, 10; pH adjusted to 7.4 with NaOH. One or more 6-channel or 8-channel Physiologic Instruments VCC MC6 or VCC MC8 epithelial voltage clamps were then used in combination to record the short circuit current (I$_{SC}$) during the entire run. The short circuit I$_{SC}$ measurements were conducted at 27° C. To initiate the run, amiloride (30 μM) was added to the apical side of the Snapwell™ filter inserts to block epithelial Na channels (ENaC). Fifteen minutes later, Forskolin (10 μM) was added to activate the CFTR. Sixty minutes later, the experiment was terminated by the addition of the CFTR$_{inh}$-172 (20 μM). Data acquisition and analyses were performed using iWorx data acquisition hardware and Labscribe 2 software (iWorx, Dover, N.H.). Comparison of agonist evoked I$_{SC}$ among both corrector positive control, negative control and test article treated epithelia was obtained with one-way ANOVA followed by Dunnett's multiple comparison test and Student's t-test when appropriate. Significant correction was defined at the level of P<0.05.

Figure 8A:
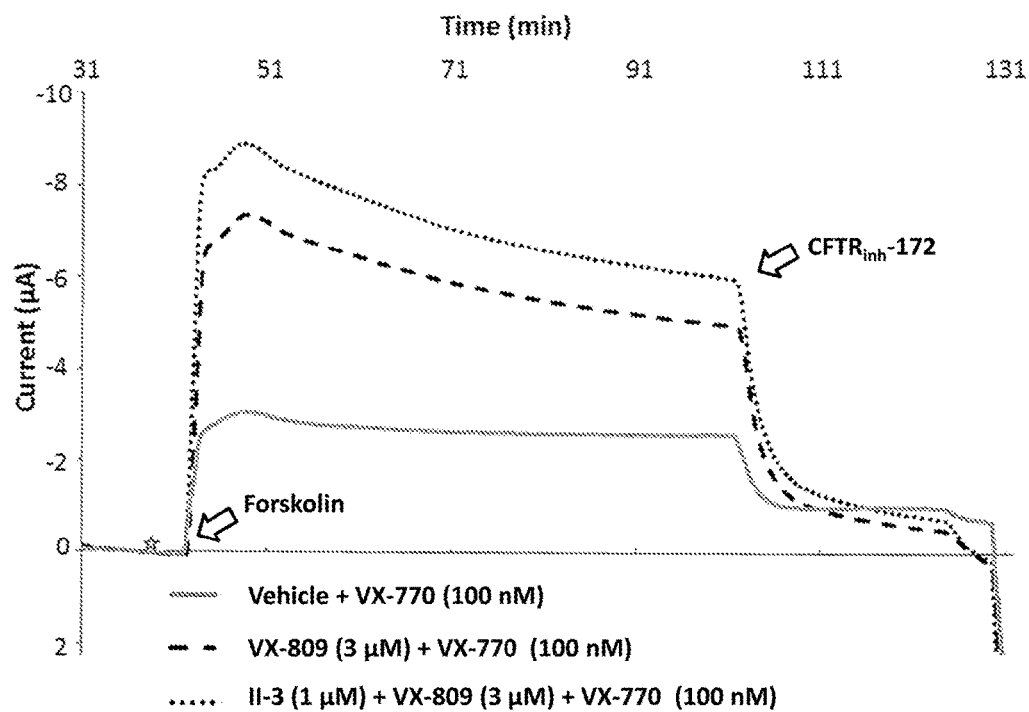
FIG. 8A is a graph showing a short circuit current ($I_{SC}$) trace generated when primary CF cells (homozygous ΔF508) were incubated for 24 hours with: (1) vehicle+VX-770 (100 nM); (2) positive control group, VX-809 (3 µM)+VX-770 (100 nM); and (3) compound II-3 (1 µM)+VX-809 (3 µM)+VX-770 (100 nM). Short circuit currents were generated in an Ussing chamber assay.
Figure 8B:
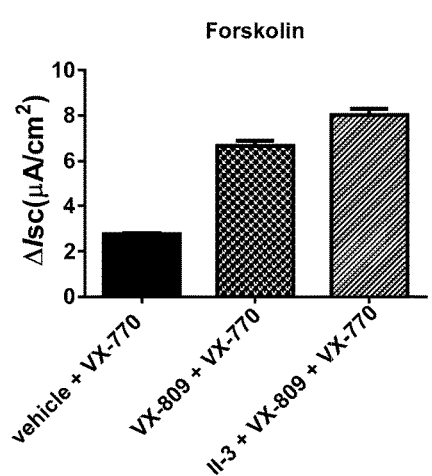
FIG. 8B is a bar chart showing the quantification of the steady state response of the traces shown in FIG. 8A upon Forskolin addition, as measured by $\Delta I_{SC}$ (µA/cm$^2$)
Figure 8C:
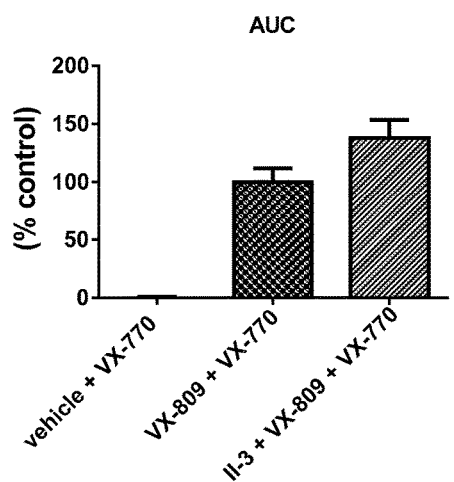
FIG. 8C is a bar chart showing the quantification of the overall response of the traces shown in FIG. 8A, as measured by the area under the curve (AUC), expressed as % of control.

FIGS. 8A, 8B and 8C summarize the data when primary CF cells were incubated for 24 hours with the following treatment groups: 1) vehicle+VX-770 (100 nM); 2) positive control group, VX-809 (3 μM)+VX-770 (100 nM); 3) compound II-3 (1 μM)+VX-809 (3 μM)+VX-770 (100 nM). FIG. 8A shows the traces of the short circuit current ($I_{SC}$) measured during the assay. To those familiar in the art, the traces shown in FIG. 8A indicated that the combination consisting of compound II-3 (1 μM)+VX-809+VX-770 was functionally more active than the positive control, the combination consisting of VX-809+VX-770. FIG. 8B shows the quantification of the steady state response upon Forskolin addition, as measured by $\Delta I_{SC}$ (μA/cm$^2$). The combination consisting of II-3 (1 μM)+VX-809+VX-770 was functionally more active than the positive control group (i.e. VX-809+VX-770), as noted by the larger increase in the $\Delta I_{SC}$. FIG. 8C shows the quantification of the overall response, as measured by the area under the curve (AUC) and expressed as % of control (wherein the positive control was expressed as 100%). As shown in FIG. 8C, the combination consisting of II-3 (1 μM)+VX-809+VX-770 showed a 137.8% increase in the AUC, when compared with the positive control (i.e. VX-809+VX-770).

Figure 9A:
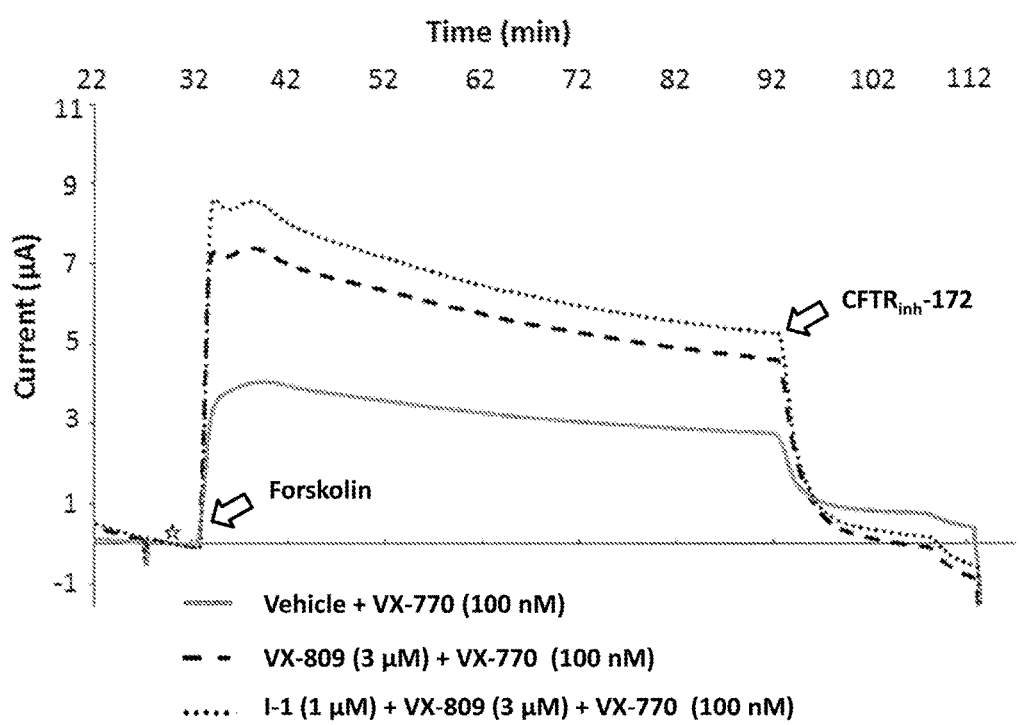
FIG. 9A is a graph showing a short circuit current ($I_{SC}$) trace generated when primary CF cells (homozygous ΔF508) were incubated for 24 hours with: (1) vehicle+VX-770 (100 nM); (2) positive control group, VX-809 (3 μM)+VX-770 (100 nM); (3) compound I-1 (1 μM)+VX-809 (3 μM)+VX-770 (100 nM). Short circuit currents were generated in an Ussing chamber assay.
Figure 9B:
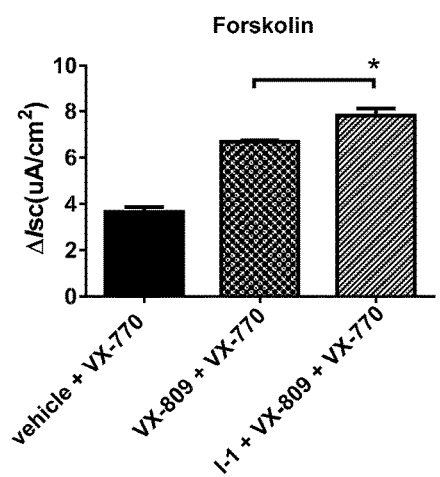
FIG. 9B is a bar chart showing the quantification of the steady state response of the traces shown in FIG. 9A upon Forskolin addition, as measured by $\Delta I_{SC}$ (μA/cm$^2$)
Figure 9C:
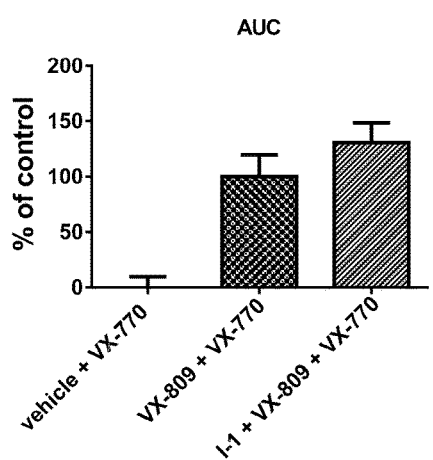
FIG. 9C is a bar chart showing the quantification of the overall response of the traces shown in FIG. 9A, as measured by the area under the curve (AUC), expressed as % of control.

FIGS. 9A, 9B and 9C summarize the data when primary CF cells were incubated for 24 hours with the following treatment groups: 1) vehicle+VX-770 (100 nM); 2) positive control group, VX-809 (3 μM)+VX-770 (100 nM); 3) compound I-1 (1 μM)+VX-809 (3 μM)+VX-770 (100 nM). FIG. 9A shows the traces of the short circuit current ($I_{SC}$) measured during the assay. To those familiar in the art, the traces shown in FIG. 9A indicated that the combination consisting of compound I-1 (1 μM)+VX-809+VX-770 was functionally more active than the positive control, the combination consisting of VX-809+VX-770. FIG. 9B shows the quantification of the steady state response upon Forskolin addition, as measured by $\Delta I_{SC}$ (μA/cm$^2$). The combination consisting of I-1 (1 μM)+VX-809+VX-770 was functionally more active than the positive control group (i.e. VX-809+VX-770), as noted by the larger increase in the $\Delta I_{SC}$. FIG. 9C shows the quantification of the overall response, as measured by the area under the curve (AUC) and expressed as % of control (wherein the positive control was expressed as 100%). As shown in FIG. 9C, the combination consisting of I-1 (1 μM)+VX-809+VX-770 showed a 130.8% increase in the AUC, when compared with the positive control (i.e. VX-809+VX-770).

Example 16

In Vitro Bacterial Clearance Assay Using Human Bronchial Epithelial Cells.

Figure 10:
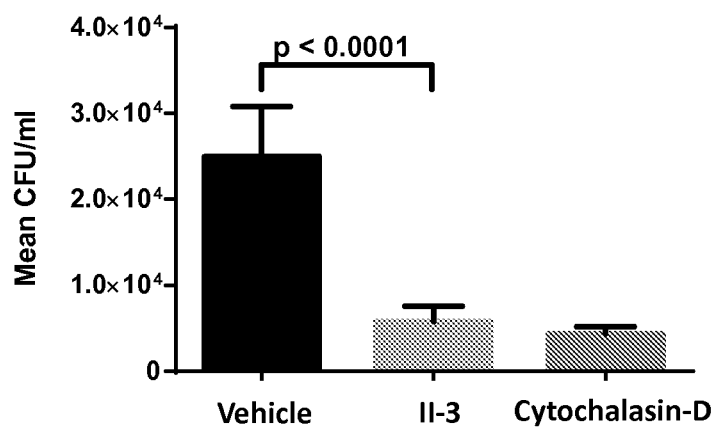
FIG. 10 is a bar chart showing the reduction in the intracellular level of bacteria (in colony forming units ("CFU")/mL) when human bronchial epithelial cells were pre-treated with compound II-3 (25 μM) prior to infection with Pseudomona aeruginosa. The positive control was the intracellular antibiotic Cytochalasin-D.

In this assay, normal 16HBE cells were cultured and seeded at 2×10$^5$ cells per well using a 48-well plate. The resulting plates were incubated at 37° C. with 5% CO$_2$ until 90% confluency. Cells were then treated with compound II-3 for 24 hours and then infected with *Pseudomona aeruginosa* strain Xen05 at a multiplicity of infection (MOI) of 1:50 (i.e. ratio of cells:bacteria) for 2 hours. Cells were then incubated with 500 μL of a mixture consisting non-permeable antibiotic (50 U/mL each of penicillin and streptomycin, mixed with 200 μg/mL gentamicin) for 3 hours to remove the extracellular bacteria. Afterwards, cells were lysed and a bacteria count was carried out to determine the remaining intracellular bacteria load. As shown in FIG. 10, compound II-3 induced an effective intracellular clearance of *Pseudomona aeruginosa* at the tested concentration of 25 μM. The intracellular bacterial killing effect was comparable to that observed by the positive control, Cytochalasin-D, a cell-permeable antibiotic.

Example 17

Assay to Assess Plasma Stability of Fatty Acid Cysteamine Conjugates

The in vitro stability of the test compounds was studied in human, mouse, beagle and rat plasma (plasma was purchased from Bioreclamation). Plasma was diluted to 50% with PBS (pH 7.4). Test compounds were dissolved in DMSO to a final concentration of 10 mM and then diluted to 1 mM in MeOH. Incubations were carried at a test compound concentration of 5 μM with a final DMSO concentration of 2.5%. Plasma (198 μL) was added to 96-well plate and incubated at 37° C. for 30 minutes before the addition of 2 μL of the test compound. The resulting mixture was then incubated at 37° C. for 2 hours. At appropriate time intervals (0, 30, 60 and 120 minutes), aliquots (50 μL) were removed and reactions were terminated by adding 200 μL of acetonitrile with an internal standard. Simultaneously, plasma samples containing Benflourex or Procaine (control compound) were terminated by adding 200 μL of acetonitrile internal standard. The sample plate was centrifuged at 3500 rpm for 45 minutes at 4° C. and the supernatant was transferred to a new plate for analysis by LC/MS-MS (Agilent Model No: HPLC: 1200, MS: 6410). Chromatographic separation was achieved with a Phenomenex C6-phenyl (5u) column. A binary gradient consisting of 0.1% formic acid in water and 0.1% formic acid in methanol was used for analyte elution.

Figure 11A:
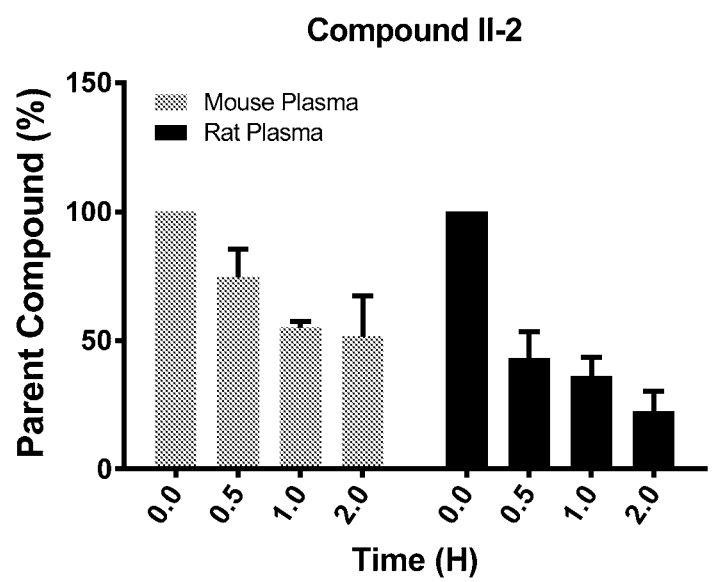
FIG. 11A is a bar chart showing the % of the parent compound II-2 remaining after incubation in either rat or mouse plasma after 0, 0.5, 1 and 2 hours.
Figure 11B:
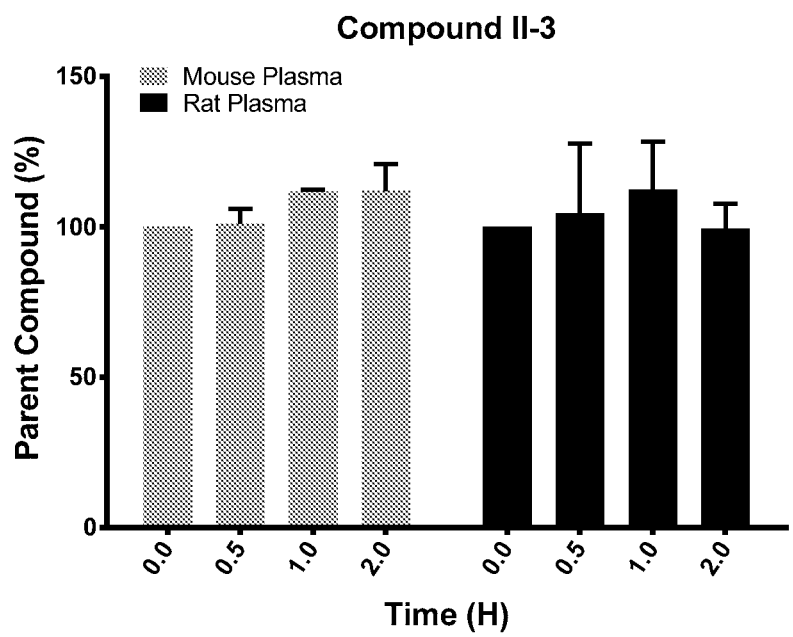
FIG. 11B is a bar chart showing the % of the parent compound II-3 remaining after incubation in either rat or mouse plasma after 0, 0.5, 1 and 2 hours.

Compound II-2 and compound II-3 were evaluated in this assay. FIGS. 11A and 11B summarize the plasma stability of the two compounds in the mouse and rat plasma. Compound II-2 was unstable in both mouse and rat plasma, as indicated by a loss of the parent compound at the 0.5, 1 and 2 hour time points (FIG. 11A). In contrast, and unexpectedly, compound II-3, with the geminal methyl group next to the disulfide linkage, showed complete plasma stability at the 0.5, 1 and 2 hour time points (FIG. 11B).

Example 18

Evaluation of a Fatty Acid Cysteamine Conjugate in an Oral Cannulated Rat PK Study The compounds of the invention were solubilized in a mixture of excipients consisting 40% Tween, 50% Peceol, 10% PEG400 and diluted with water to form a self-emulsifying aqueous mixture for oral administration to animals. For this study, Sprague Dawley rats that have been surgically implanted with indwelling jugular vein cannula (JVC) and portal vein cannula (PVC) were used (Agilux, Worcester, Mass.). This approach using double-cannulated rats allowed the measurement of the drug concentration that was delivered in the portal vein as well as the drug concentration that was present in the peripheral. For the PK study, serial blood collection was carried out at both the portal and jugular vein at the following time points: 10, 20, 40 min and 1, 2, 4 and 6 hours post dose. The bioanalytical portion of the PK study was carried out using an LC/MS/MS system (Agilent Model No: HPLC: 1200, MS: 6410) and analyzed with the appropriate software (WinNonlin Phoenix 64 6.3.0 395).

Compounds II-2 and II-3 were evaluated in this oral cannulated rat PK experiment. For compound II-2, since it was not stable in the rat plasma, a significant amount of the parent compound was degraded upon oral dosing. The portal $C_{max}$ for compound II-2 was 20.8±9.45 ng/mL, along with an $AUC_{last}$ of 12.5±6.5 Hr*ng/mL. In the systemic circulation, the peripheral $C_{max}$ of compound II-2 was 0.889±0.33 ng/mL, along with an AUClast of 0.443±0.221 Hr*ng/mL. For compound II-3, the portal $C_{max}$ was 331±120 ng/mL, along with an $AUC_{last}$ of 679±226 Hr*ng/mL. The geminal methyl group present in compound II-3 also rendered it more resistant to first pass metabolism. Compared to compound II-2, a significantly higher proportion of the parent compound II-3 was orally bioavailable in the systemic circulation. The corresponding peripheral $C_{max}$ for compound II-3 was 102±16.9 ng/mL, along with an $AUC_{last}$ of 300±103 Hr*ng/mL. The peripheral $C_{max}$ of the parent compound II-3 was 100-fold higher than the corresponding peripheral $C_{max}$ of the parent compound II-2.

Example 19

In Vivo Determination of Autophagy Activation

Figure 12:
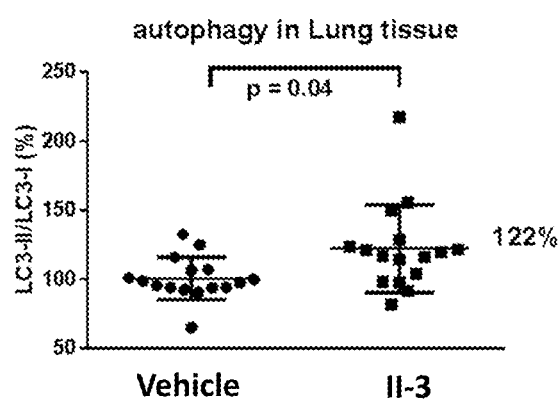
FIG. 12 is a bar chart showing the level of autophagy activation (an increase of 22%) in lung tissues when naive BALB/c mice were treated with compound II-3 for 3.5 days (100 mg/kg, BID, po).

In order to evaluate for in vivo autophagy activation, nave male C57BL/6 mice were dosed orally with compound II-3 (100 mg/kg, BID, 3.5 days). One hour after the last dose, lung tissues and plasma were collected to analyze for drug concentration and autophagy biomarkers. As discussed in earlier examples, the ratio of LC3-II to LC3-I was used as autophagy biomarker. When compound II-3 was dosed orally, the parent compound (i.e. II-3) and a major metabolite (i.e. compound I-1) was detected both in the plasma and lung tissues. One hour after the last dose, the plasma concentration of the parent compound II-3 was 143.0±52.35 ng/mL and the corresponding metabolite I-1 was 741.37±170.2 ng/mL. At this time point, the mouse lung tissue concentration of the parent compound II-3 was 536.48±24.01 ng/g. The metabolite I-1 was also detected in the lung tissues, at a concentration of 411.48±164.0 ng/g. Compound II-3 was able to induce autophagy at the given dose of 100 mg/kg and the 22% increase in the ratio of LC3-II to LC3-I in the isolated lung tissues was statistically significant (p=0.04, FIG. 12).

Example 20

Assessment of a Fatty Acid Cysteamine Conjugate in a Model of Murine Lung Infection with *Pseudomoma Aeruginosa*

In this model of murine lung infection with *Pseudomona aeruginosa*, female BALB/c mice, aged 6-7 weeks, were allowed to acclimate for one week in five groups of 10 animals per cage. From 3.5 days prior to the infection, animals were treated with compound II-3 (formulated as described above) at 100 mg/kg po, BID; animals are then kept on the same II-3 treatment for the duration of the study. Four other treatment groups were used in this study, including the vehicle control and the positive control groups: Group 1) vehicle, po (BID from day −3.5) and s.c. (BID from 8 hours post infection); Group 2) compound II-3 po (BID, 100 mg/kg from day −3.5) plus vehicle s.c. (BID from 8 hours post infection); Group 3) Ciprofloxacin, positive control, sub-efficacious dose, 1 mg/kg s.c. (BID from 8 hours post infection), plus vehicle p.o. (BID from day −3.5); Group 4) Ciprofloxacin, 1 mg/kg s.c. (BID from 8 hours post infection), plus compound II-3 po (BID, 100 mg/kg, from day −3.5); Group 5) Ciprofloxacin, positive control, 20 mg/kg s.c. (BID from 8 hours post infection).

Animals were weighed prior to treatment and daily thereafter until the termination of the study. Once infected with *Pseudomona aeruginosa*, animals were observed regularly for signs of ill-health and body temperatures were monitored. Animals reaching humane endpoints were terminated and time of death recorded. At termination, 24/48 hours post infection, lungs were removed and signs of gross pathology scored and photographed. Lung, spleen, and kidney were removed, weighed and transferred into PBS, homogenized and serial dilutions plated out to determine the bacterial load.

Example 21

Evaluation for Anti-Fibrotic and Anti-Inflammatory Activity in Cell-Based Assays Cell Preparation Normal human lung fibroblasts (ScienCell Research Laboratory 3420), lung fibroblasts from idiopathic pulmonary fibrosis (IPF) patients LL29 (AnHa) (ATCC) and LL97A (ALMy) (ATCC) were maintained in DMEM F12 (Gibco 10565) supplemented with 15% fetal bovine serum (FBS) (Gibco 10437-028) plus Pen-Strep (1%) (Gibco 15140-122). Cells were split every 3 to 4 days at 1:2/1:3 dilution each time. The day before the experiment, cells were trypsinized using Trypsin-EDTA (0.05%) (Gibco 25300-054) and plated on 24-well fish at 1×10$^5$ cells per well.

THP-1 cells were obtained from ATCC® TIB202. THP-1 cells were maintained in RPMI1640 (Gibco® RPMI 1640) supplemented with 10% fetal bovine serum. DMEM (#11095) and fetal bovine serum (low endotoxin grade) (#10437) was obtained from Invitrogen.

Drug Treatment

Compounds II-3 and I-1 were first solubilized in 100% DMSO as 50 mM solution, and then diluted 1 to 200 in 1% BSA as a 10× stock solution of 250 nm, and series stock dilution (1 to 2 dilution) were carried out as needed. The 10× stock solution were added to the cell media and cells were incubated for 24 hours at 37° C. For LPS stimulation in THP-1 cells, compounds were added to the cell media for 6 hours at and at the end of 4 hours, 50 µg/ml final concentration of LPS (Sigma L3024) was added and cells were incubated for 2 hours. Normal human lung fibroblasts (NLF) or idiopathic pulmonary fibrosis cells (LL29 and LL79A cells, ATCC) were incubated with compound II-3 (25 µM) and I-1 (25 µM) for 24 hours in the presence of TGFβ (Abcam ab50036, 50 ng/mL) or in the absence of TGFβ (referred to as PBS treatment group). The test compounds were added to cells 30 minutes prior to TGFβ addition. The total RNA was harvested, and the relative mRNA expression levels were assessed via RT-PCR with HPRT as the internal control. Data are represented as the mean AmRNA/HPRT, error bars represent the standard error of the mean (SEM). Significance was determined by student's t-test in comparison to control.

ELISA

Conditioned media were collected at the end of the experiment. The levels of Matrix Metalloproteinase 2 (MMP-2) (R&D System MMP200) and human Tissue Inhibitor of Metalloproteinase 2 (TIMP-2) (R&D System DTM200) were measured according to the manufacturer's instruction. A 100-fold dilution of conditioned media was used in these assays. The ELISA was measured on a Victor×5 multilabel plate reader (PerkinElmer) at an absorbance of 450 nm with background correction at 550 nm. Standard curve were generated and levels of TIMP-2 and MMP-2 were calculated according the standard curve. Conditioned media were collected and the levels of Matrix Metalloproteinase 2 (MMP-2) and human Tissue Inhibitor of Metalloproteinase 2 (TIMP-2) were determined. Data are represented as the mean fold change over the control and error bars represent the standard error of the mean (SEM). Significance was determined by student's t-test in comparison to control.

RT-PCR

Total RNA was collected using RNeasy Plus Mini Kit (Qiagen #74136) and cDNA generated using SuperScriptIII (Invitrogen #18080-044) with random hexamers following the manufacturer's protocol. Relative mRNA expression levels were determined using TaqMan probes (Applied Biosystems, using the recommended best primer pairs) with HPRT (hypoxanthine phosphoryltransferase) as the internal control. All PCR probes were purchased from Invitrogen. TNFα (HS 01113624), IL1β (HS 01555410), CCL2 (HS 00234140), Collagen 1a1 (HS 00164004), FN1 (Fibronectin 1, HS 00365052), TIMP-2 (HS 00234278), MMP-2 (HS 01548727). Collagen 1a1 (COL1a1), FN1, TIMP-2, and MMP-2 are well-known markers for fibrosis (see, Selman et al. (2000) AM. J. PHYS. LUNG CELL MOL. PHYSIOL., 279, L562-L574).

Figure 13A:
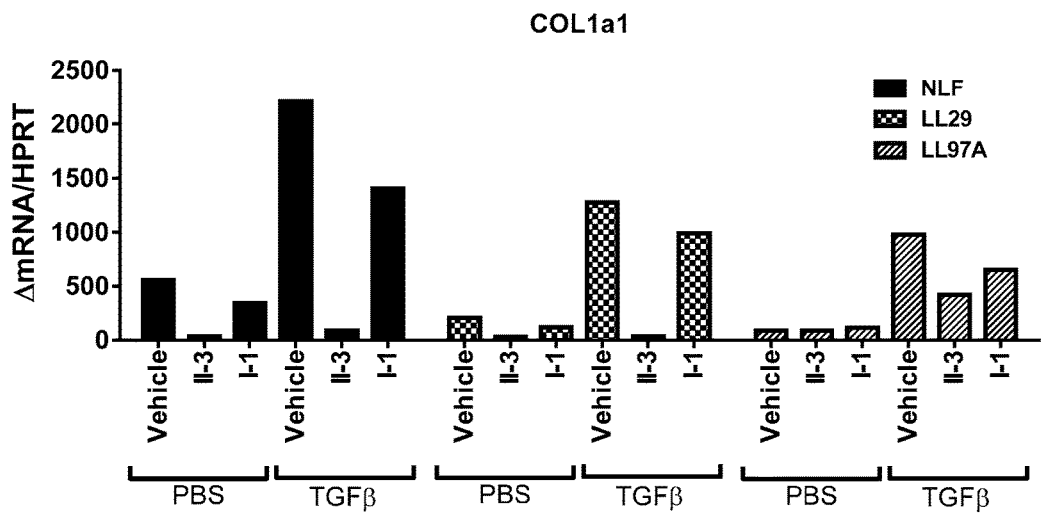
FIG. 13A is a bar chart showing the mRNA level of Collagen 1a1 (COL1a1) when normal human lung fibroblasts (NLF) or idiopathic pulmonary fibrosis cells (LL29 and LL79A) were treated with compound II-3 (25 μM) or I-1 (25 μM) under either PBS or TGFβ stimulation.
Figure 13B:
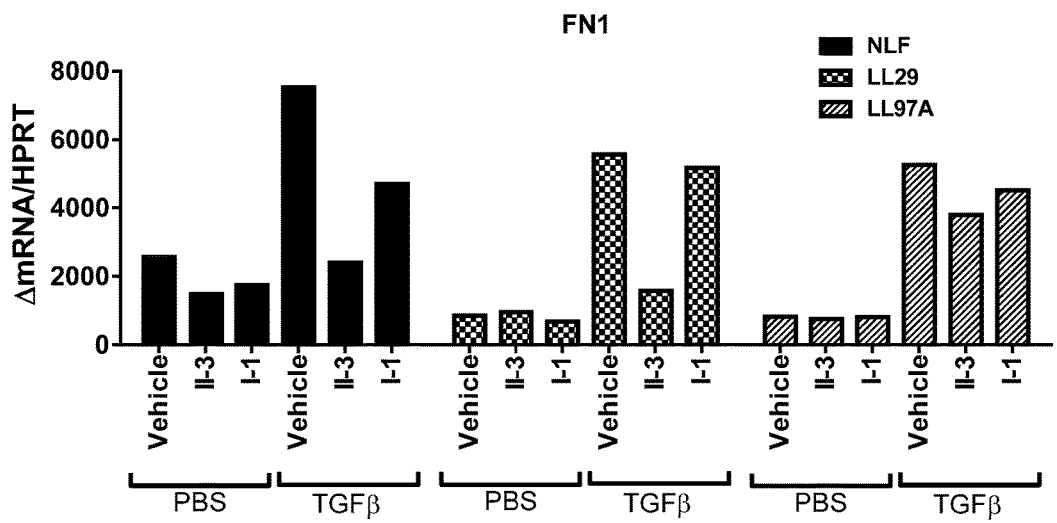
FIG. 13B is a bar chart showing the mRNA level of Fibronectin 1 (FN1) when normal human lung fibroblasts (NLF) or idiopathic pulmonary fibrosis cells (LL29 and LL79A) were treated with compound II-3 (25 μM) or I-1 (25 μM) under either PBS or TGFβ stimulation.
Figure 13C:
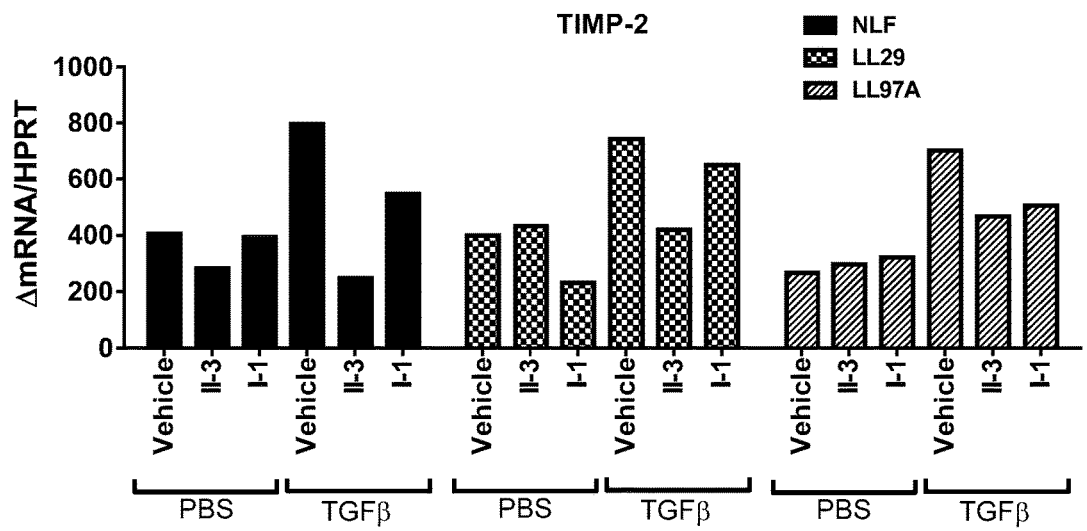
FIG. 13C is a bar chart showing the mRNA level of TIMP-2 when normal human lung fibroblasts (NLF) or idiopathic pulmonary fibrosis cells (LL29 and LL79A) were treated with compound II-3 (25 μM) or I-1 (25 μM) under either PBS or TGFβ stimulation.

Results:

Compounds II-3 and I-1 were evaluated in both normal human lung fibroblasts (NLF) and lung fibroblasts from idiopathic pulmonary fibrosis (IPF) patients (LL29 and LL97A). The results are summarized in FIGS. 13A-C, 14A-D, and 15A-D. FIG. 13A shows the mRNA level of Collagen 1a1 (COL1a1) when these 3 different types of cells were treated with compound II-3 or I-1 under either PBS or TGFβ stimulation. Cells, either normal lung fibroblasts (NLF) or IPF cells (LL29 or LL97A), that have been treated with TGFβ showed a significantly enhanced level of Collagen 1a1, which was suppressed upon treatment with either compound II-3 (25 µM) or I-1 (25 µM). FIGS. 13B and 13C shows the corresponding mRNA level of Fibronectin 1 (FN1) and TIMP-2 when these 3 different types of cells were treated with compound II-3 (25 µM) or I-1 (25 µM) under either PBS or TGFβ stimulation. NLF, LL29 or LL97A cells that have been treated with TGFβ showed a significantly enhanced level of FN1 and TIMP-2, which were suppressed upon treatment with either compound II-3 (25 µM) or I-1 (25 µM). COL1a1, FN1 and TIMP-2 are well-known markers of fibrosis; and suppression of these markers indicated anti-fibrotic activity for compounds II-3 and I-1.

Figure 14A:
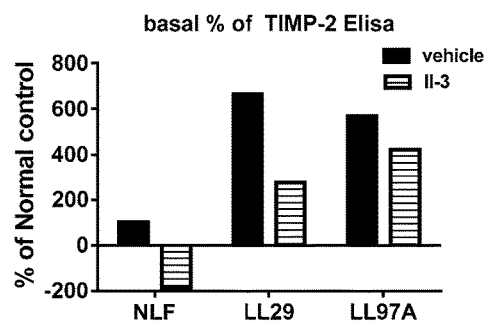
FIG. 14A is a bar chart showing the basal level of TIMP-2 (PBS treatment) when NLF, LL29 or LL97A cells were treated with either the vehicle or compound II-3 (25 μM)
Figure 14B:
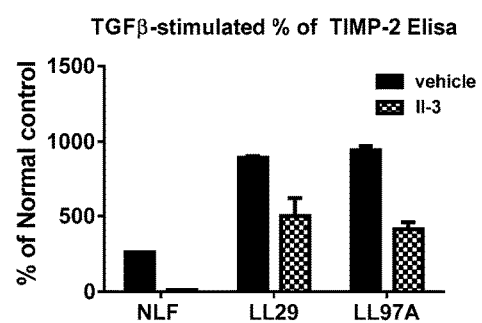
FIG. 14B is a bar chart showing the level of TIMP-2 when NLF, LL29 or LL97A cells were treated with either the vehicle or compound II-3 (25 μM) under TGFβ stimulation.
Figure 15A:
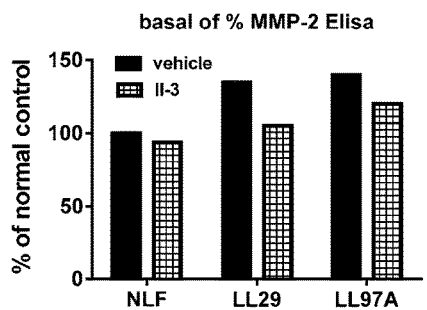
FIG. 15A is a bar chart showing the basal level of MMP-2 (PBS treatment) when NLF, LL29 or LL97A cells were treated with either the vehicle or compound II-3 (25 μM)
Figure 15B:
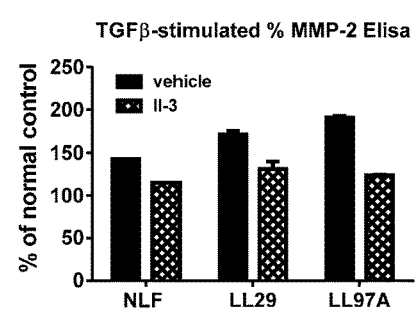
FIG. 15B is a bar chart showing the level of MMP-2 when NLF, LL29 or LL97A cells were treated with either the vehicle or compound II-3 (25 μM) under TGFβ stimulation.

The level of MMP-2, a known mediator of matrix degradation, and its natural inhibitor TIMP-2 were also evaluated in the conditioned media. As shown in FIG. 14A-B and FIG. 15A-B, the level of MMP2 and TIMP-2 was both elevated in the disease lung fibroblasts, when compared to normal lung. This imbalance between MMP-2 and TIMP-2 has been reported to cause the accumulation of the extracellular matrix (ECM) in fibrogenesis (see, Selman et al. (2000) AM. J. PHYS. LUNG CELL MOL. PHYSIOL., 279, L562-L574). Accordingly, a greater increase in the level of TIMP-2 than that of MMP-2 in IPF lung tissues was reported and such an imbalance would favor the enhanced deposition of ECM proteins. FIG. 14A shows the basal level of TIMP-2 (PBS treatment) when NLF, LL29 or LL97A cells were treated with either the vehicle or compound II-3 (25 µM). FIG. 14B shows the level of TIMP-2 when NLF, LL29 or LL97A cells were treated with either the vehicle or compound II-3 (25 µM) under TGFβ stimulation. Treatment with compound II-3 resulted in a marked reduction of TIMP-2 level, in the presence of TGFβ. FIGS. 15A and 15B show the corresponding basal (PBS treatment) and TGFβ-stimulated level of MMP-2 for NLF, LL29 and LL97A cells upon treatment with either the vehicle or compound II-3. Again, treatment with compound II-3 resulted in a marked reduction of MMP-2 level, in the presence of TGFβ.

Figure 16A:
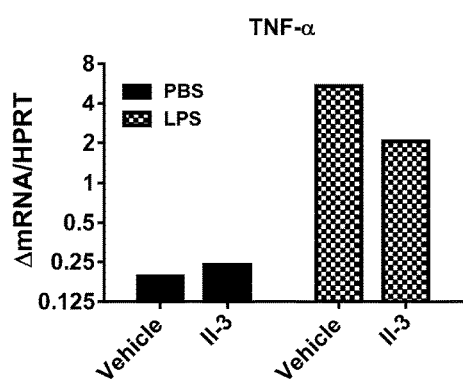
FIG. 16A is a bar chart showing the TNF-α mRNA level when THP-1 cells were treated with either vehicle or compound II-3 (25 μM)
Figure 16B:
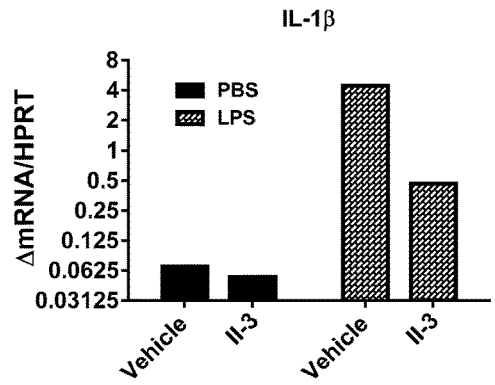
FIG. 16B is a bar chart showing the IL-1β mRNA level when THP-1 cells were treated with either vehicle or compound II-3 (25 μM)
Figure 16C:
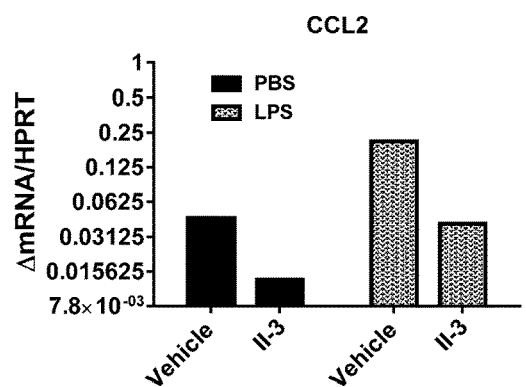
FIG. 16C is a bar chart showing the CCL2 mRNA level when THP-1 cells were treated with either vehicle or compound II-3 (25 μM).

Compound II-3 was evaluated for its anti-inflammatory activity in THP-1 cells. FIGS. 16A, 16B and 16B summarize the data for the commonly used markers of inflammation: and TNF-α, IL-1β, and CCL2. LPS stimulation caused the customary increase in the mRNA expression of CCL2, IL-1β, and TNF-α. As shown in FIGS. 16A-C, treatment with 25 µM of compound II-3 under LPS stimulation resulted in a marked reduction in all three markers of inflammation.

Example 22

Assessment of Fatty Acid Cysteamine Conjugates in the Bleomycin Mouse Model of Fibrosis Specific pathogen-free 7 weeks old female C57BL/6J mice are used for the experiment. On day 0, 40 mice are induced to develop pulmonary fibrosis by a single intratracheal administration of bleomycin sulfate (BLM) in saline at a dose of 3 mg/kg using Microsprayer® (Penn-Century, USA). Animals are then randomized into 4 groups of 10 mice, based on the body weight on the day before the start of the treatment. Individual body weight will be measured daily during the duration of the study. Survival, clinical signs and behavior of mice are monitored daily. The compounds of the invention are administered orally using the formulation described in earlier examples. The 4 treatment groups of the study are consisted of the followings: Group 1) vehicle; Group 2) the test compound, dosed po, BID at 30 mg/kg daily from day 0 to 20; Group 3) the test compound, dosed po, BID at 100 mg/kg daily from day 0 to 20; Group 4) dexamethasone control group, dosed orally at 0.25 mg/kg. On day 21, mice in all groups are terminated. For the biochemical analysis, the lung hydroxyproline can be quantified by a hydrolysis method. For the histological analysis of lung sections, Masson's Trichome staining and estimation of Ashcroft score can be carried out using known protocols (see, Schaefer et al. (2011) EUR. RESP. REV., 20:120, p. 85-97). Statistical tests can be performed using Bonferroni Multiple Comparison Test. P values <0.05 are considered statistically significant.

Example 23

Comparison Between Compounds II-2 and II-3

Figure 17:
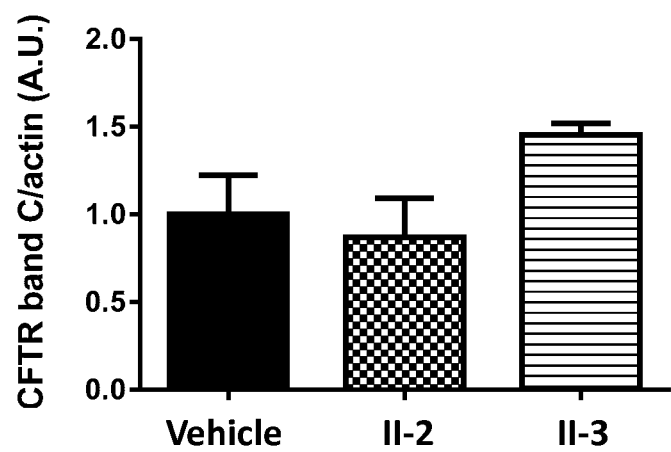
FIG. 17 is a bar chart showing the ratio of CFTR band C/actin when primary CF cells were treated with either vehicle or 25 μM each of compound II-2 and II-3.

The bis-geminal methyl groups present in compound II-3 offers several advantages when compared compound II-2, an analog without the bis-geminal methyl groups. For instance, compound II-3 shows better plasma stability than compound II-2 (see, Example 17). Compound II-3 also has a better oral exposure in the rat, as illustrated in Example 18. The peripheral $AUC_{last}$ for the parent compound II-2 was 0.889 ng/mL. In contrast, the peripheral $AUC_{last}$ for compound II-3 was 102 ng/mL; a 100-fold increase in the AUC when dosed orally to rats. Consistent with the greater stability due to the bis-geminal methyl group, compound II-3 was also more effective than compound II-2 in cellular assays. Previously, in Example 11, compound II-2 was evaluated in HT-29 cells after a short incubation period of 4 hours at 50 µM. For a more direct comparison, the two compounds were evaluated at a lower concentration of 25 µM over a longer incubation period of 24 hours. The 24 hour incubation period was also the time needed to obtain the maximal activity out of CFTR correctors such as VX-809 in the Ussing chamber assays. Primary CF cells (homozygous ΔF508) were treated with the following groups for 24 hours using the same protocols outlined previously in Example 13: 1) vehicle; 2) Compound II-2 (25 μM); 3) Compound II-3 (25 μM). As shown in FIG. 17, compound II-3 was more effective than compound II-2 in trafficking the misfolded ΔF508 CFTR at the lower concentration of 25 μM, under the 24 hour incubation period.

INCORPORATION BY REFERENCE

The entire disclosure of each of the patent and scientific documents referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A compound of Formula I-A

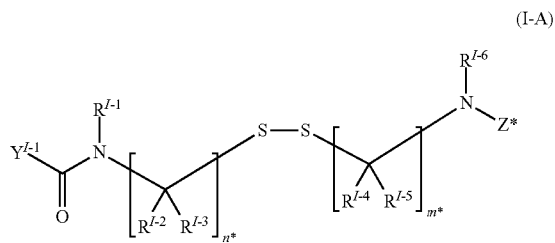

(I-A)

or a pharmaceutically acceptable salt or solvate thereof; wherein:
$R^{I-1}$, $R^{I-2}$, $R^{I-3}$, $R^{I-4}$, $R^{I-5}$, and $R^{I-6}$ each represent independently for each occurrence hydrogen or $C_1$-$C_3$ alkyl;
$Y^{I-1}$ is a 6-membered heteroaryl optionally substituted with 1, 2, or 3 substituents independently selected from the group consisting of alkyl, alkoxyl, halogen, and acyl;
n* and m* are independently 2 or 3;
Z* is

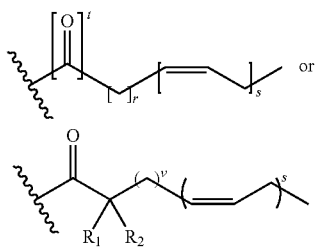

wherein:
$R_1$ and $R_2$ independently are hydrogen, $C_1$-$C_4$ alkyl, or halogen;
r is 2, 3, or 7;
s is 3, 5, or 6;
t is 0 or 1; and
v is 1, 2, or 6;
provided that, when Z is

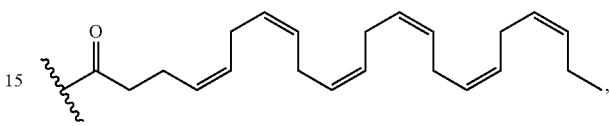

then at least one of $R^{I-1}$, $R^{I-2}$, $R^{I-3}$, $R^{I-4}$, $R^{I-5}$, or $R^{I-6}$ is $C_1$-$C_3$ alkyl, or at least one of n* or m* is 1 or 3, or $Y^{I-1}$ is other than 3-pyridinyl.

2. The compound of claim 1, wherein $R^{I-1}$, $R^{I-2}$, $R^{I-3}$, $R^{I-4}$, $R^{I-5}$, and $R^{I-6}$ each represent independently for each occurrence hydrogen or methyl.

3. The compound of claim 1, wherein $R^{I-1}$, $R^{I-2}$, $R^{I-3}$, $R^{I-4}$, $R^{I-5}$, and $R^{I-6}$ are hydrogen.

4. The compound of claim 1, wherein n* is 2.

5. The compound of claim 1, wherein m* is 2.

6. The compound of claim 1, wherein $Y^{I-1}$ is a 6-membered heteroaryl optionally substituted with 1, 2, or 3 substituents independently selected from the group consisting of alkyl and alkoxyl.

7. The compound of claim 1, wherein $Y^{I-1}$ is pyridinyl or pyrimidinyl, each of which is optionally substituted with 1, 2, or 3 substituents independently selected from the group consisting of alkyl and alkoxyl.

8. The compound of claim 1, wherein $Y^{I-1}$ is pyridinyl optionally substituted with 1, 2, or 3 substituents independently selected from the group consisting of alkyl and alkoxyl.

9. The compound of claim 1, wherein $Y^{I-1}$ is pyridinyl.

10. The compound of claim 1, wherein $Y^{I-1}$ is

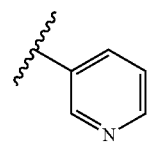

optionally substituted with 1, 2, or 3 substituents independently selected from the group consisting of alkyl and alkoxyl.

11. The compound of claim 1, wherein $Y^{I-1}$ is

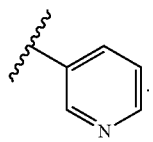 [SMILES: *c1cccnc1]

12. The compound of claim 1, wherein Z* is

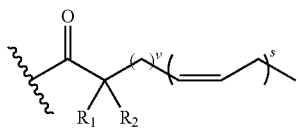

wherein R₁ and R₂ are hydrogen or methyl.

13. The compound of claim 12, wherein R₁ and R₂ are hydrogen.

14. The compound of claim 1, wherein at least one pair of $R^{I-2}$ and $R^{I-3}$ bonded to the same carbon atom independently are $C_1$-$C_3$ alkyl.

15. The compound of claim 14, wherein each $C_1$-$C_3$ alkyl is a methyl.

16. The compound of claim 1, wherein at least one pair of $R^{I-4}$ and $R^{I-5}$ bonded to the same carbon atom independently are $C_1$-$C_3$ alkyl.

17. The compound of claim 16, wherein each $C_1$-$C_3$ alkyl is a methyl.

18. The compound of claim 1, wherein the compound is selected from the group consisting of:

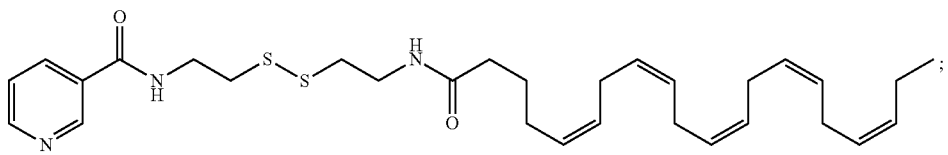
(II-2)

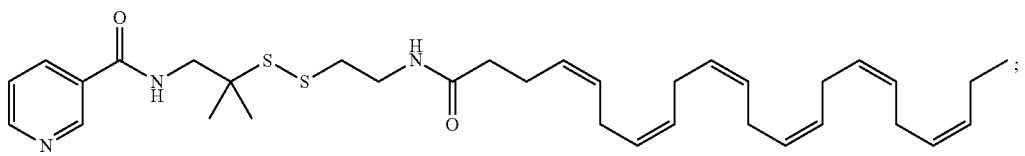
(II-3)

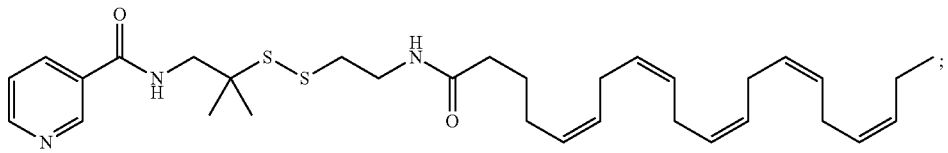
(II-4)

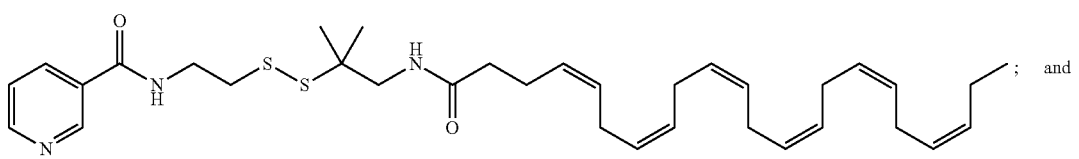
(II-5) ; and

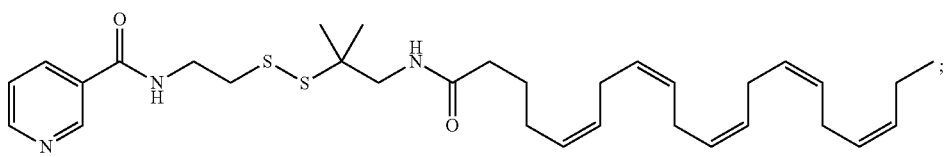
(II-6)

and pharmaceutically acceptable salts thereof.

19. The compound of claim 1, wherein the compound is

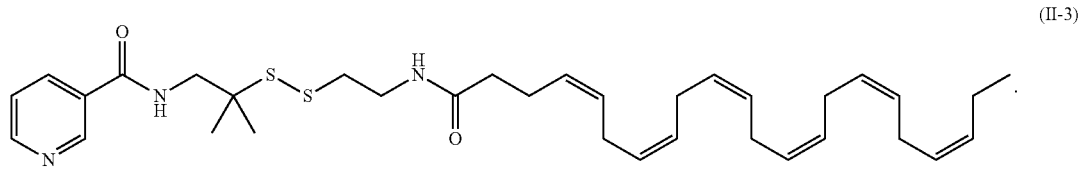 [SMILES: CC/C=C\C/C=C\C/C=C\C/C=C\C/C=C\C/C=C\CCC(=O)NCCSSC(C)(C)CNC(=O)c1cccnc1]
(II-3)

20. The compound of claim 1, wherein the compounds is

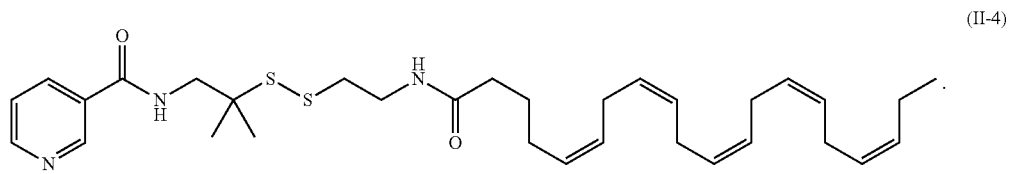 [SMILES: CC/C=C\C/C=C\C/C=C\C/C=C\C/C=C\CCCC(=O)NCCSSC(C)(C)CNC(=O)c1cccnc1]
(II-4)

21. A pharmaceutical composition comprising a compound of claim 1 and a pharmaceutically acceptable carrier.

22. A pharmaceutical composition comprising the compound of claim 18 and a pharmaceutically acceptable carrier.

23. A pharmaceutical composition comprising the compound of claim 19 and a pharmaceutically acceptable carrier.

24. A pharmaceutical composition comprising the compound of claim 20 and a pharmaceutically acceptable carrier.

* * * * *